US008492529B2

(12) United States Patent
Takada et al.

(10) Patent No.: US 8,492,529 B2
(45) Date of Patent: Jul. 23, 2013

(54) MONOCLONAL ANTIBODY CAPABLE OF BINDING TO SPECIFIC DISCONTINUOUS EPITOPE OCCURRING IN AD1 REGION OF HUMAN CYTOMEGALOVIRUS GB GLYCOPROTEIN, AND ANTIGEN-BINDING FRAGMENT THEREOF

(75) Inventors: Kenzo Takada, Hokkaido (JP); Rika Kurino, Hokkaido (JP); Takashi Torashima, Hokkaido (JP)

(73) Assignee: Evec Incorporated, Hokkaido (JP)

( * ) Notice: Subject to any disclaimer, the term of this patent is extended or adjusted under 35 U.S.C. 154(b) by 0 days.

(21) Appl. No.: 13/262,061

(22) PCT Filed: Apr. 1, 2010

(86) PCT No.: PCT/JP2010/056037
§ 371 (c)(1),
(2), (4) Date: Dec. 5, 2011

(87) PCT Pub. No.: WO2010/114106
PCT Pub. Date: Oct. 7, 2010

(65) Prior Publication Data
US 2012/0093810 A1 Apr. 19, 2012

(30) Foreign Application Priority Data
Apr. 1, 2009 (JP) ................................ 2009-089442

(51) Int. Cl.
*C07K 16/00* (2006.01)
*A61K 39/395* (2006.01)
*A61K 39/42* (2006.01)

(52) U.S. Cl.
USPC .................. 530/388.1; 530/388.3; 424/130.1; 424/141.1; 424/147.1

(58) Field of Classification Search
None
See application file for complete search history.

(56) References Cited

U.S. PATENT DOCUMENTS

| 5,043,281 A | 8/1991 | Masuho et al. |
| 5,750,106 A | 5/1998 | Ostberg |
| 2009/0004198 A1 | 1/2009 | Nakajima et al. |

FOREIGN PATENT DOCUMENTS

| JP | 08-502403 A | 3/1996 |
| JP | 08-506325 A | 7/1996 |
| WO | WO 87/03602 A1 | 6/1987 |
| WO | WO 93/21952 A1 | 11/1993 |
| WO | WO 94/09136 A1 | 4/1994 |
| WO | WO 03/000720 A1 | 1/2003 |
| WO | WO 2007/094423 A1 | 8/2007 |
| WO | WO 2008/084410 A2 | 7/2008 |
| WO | WO 2009/003975 A1 | 1/2009 |
| WO | WO 2009/024445 A1 | 2/2009 |

OTHER PUBLICATIONS

Britt et al., "Antigenic Domain 1 is Required for Oligomerization of Human Cytomegalovirus Glycoprotein B," Journal of Virology, Apr. 2005, 79(7):4066-4079.
Davison et al., "The human cytomegalovirus genome revisited: comparison with the chimpanzee cytomegalovirus genome," Journal of General Virology, 2003, 84:17-28.
Demmler, Gail J. MD, "Congenital Cytomegalovirus Infection and Disease," Seminars in Pediatric Infectious Diseases, Jul. 1999, 10(3):195-200.
Dolan et al., "Genetic content of wild-type human cytomegalovirus," Journal of General Virology, 2004, 85:1301-1312.
Freitas et al., "Activity of 9-(1,3-Dihydroxy-2-Propoxymethyl)Guanine Compared with That of Acyclovir Against Human, Monkey, and Rodent Cytomegaloviruses," Antimicrobial Agents and Chemotherapy, Aug. 1985, 28(2):240-245.
Griffiths, Paul D., "The treatment of cytomegalovirus infection," Journal of Antimicrobial Chemotherapy, 2002, 49:243-253.
Isaacson et al., "Human Cytomegalovirus Glycoprotein B is Required for Virus Entry and Cell-to-Cell Spread but Not for Virion Attachment, Assembly, or Egress," Journal of Virology, Apr. 2009, 83(8):3891-3903.
Kimberlin et al., "Effect of Ganciclovir Therapy on Hearing in Symptomatic Congenital Cytomegalovirus Disease Involving the Central Nervous System: A Randomized, Controlled Trial," J. Pediatr., 2003, 143:16-25.
Kniess et al., "Distribution of Linear Antigenic Sites on Clygoprotein gp55 of Human Cytomegalovirus," Journal of Virology, Jan. 1991, 65(1):138-146.
Masuho et al., "Human Monoclonal Antibodies Neutralizing Human Cytomegalovirus," Journal of General Virology, 1987, 68:1457-1461.
Navarro et al., "Glycoprotein B of Human Cytomegalovirus Promotes Virion Penetration into Cells, Transmission of Infection from Cell to Cell, and Fusion of Infected Cells," Virology, 1993, 197:143-158.
Ohizumi et al., "Neutralizing mechanisms of two human monoclonal antibodies against human cytomegalovirus glycoprotein 130/55," Journal of General Virology, 1992, 73:2705-2707.
Ohlin et al., "Fine Specificity of the Human Immune Response to the Major Neutralization Epitopes Expressed on Cytomegalovirus gp58/116 (gB), as Determined with Human Monoclonal Antibodies," Journal of Virology, Feb. 1993, 67(2):703-710.
Qadri et al., "Assembly of conformation-dependent neutralizing domains on glycoprotein B of human cytomegalovirus," Journal of General Virology, 1992, 73:2913-2921.

(Continued)

*Primary Examiner* — Hong Sang
(74) *Attorney, Agent, or Firm* — Foley & Lardner LLP

(57) ABSTRACT

The present invention provides a pharmaceutical composition for human cytomegalovirus HCMV causative of various disease states, the composition comprising a monoclonal antibody and an antigen-binding fragment thereof that specifically binds to the AD1 region of glycoprotein gB and that has excellent neutralizing capacity. The present invention provides: a monoclonal antibody and an antigen-binding fragment thereof having an excellent neutralizing capacity and cell-to-cell infection blocking capacity and specifically binding to a discontinuous sequence occurring in the HCMV AD1 region; a pharmaceutical composition comprising the antibody or the fragment thereof; and the like.

7 Claims, 7 Drawing Sheets

OTHER PUBLICATIONS

Wagner et al., "A Continuous Sequence of More than 70 Amino Acids is Essential for Antibody Binding to the Dominant Antigenic Site of Glycoprotein gp58 of Human Cytomegalovirus," Journal of Virology, Sep. 1992, 66(9):5290-5297.

Chou et al., "Homology of the Envelope Glycoprotein B of Human Herpesvirus-6 and Cytomegalovirus," Virology, Nov. 1, 1992, 191(1):523-528.

Davies et al., "Affinity improvement of single antibody VH domains: residues in all three hypervariable regions affect antigen binding," Immunotechnology, Sep. 1, 1996, 2(3):169-179.

Holt et al., "Domain antibodies: proteins for therapy," Trends in Biotechnology, Nov. 1, 2003, 21(11):484-490.

MacAgno et al., "Isolation of Human Monoclonal Antibodies that Potently Neutralize Human Cytomegalovirus Infection by Targeting Different Epitopes on the gH/gL/UL128-131A Complex," Journal of Virology, Jan. 2010, 84(2):1005-1013.

Navarro et al., "Humoral Immune Response to Functional Regions of Human Cytomegalovirus Glycoprotein B," Journal of Medical Virology, Aug. 1, 1997, 52(4):451-459.

Tugizov et al., "Function of Human Cytomegalovirus Glycoprotein B: Syncytium Formation in Cells Constitutively Expressing gB is Blocked by Virus-Neutralizing Antibodies," Virology, Jun. 1, 1994, 201(2):263-276.

Krauss et al., "Impact of antibody framework residue VH-71 on the stability of a humanized anti-MUCI scFv and derived immunoenzyme," British Journal of Cancer, 2004, 90:1863-1870.

Pakula et al., "Genetic Analysis of Protein Stability and Function," Annu. Rev. Genet., 1989, 23:289-310.

Royt et al., "Binding of antibodies with an antigen," Immunology, Moscow, Mir, 2000, Chapter 9, p. 150.

Fig. 3

| Serial Number | Name of Variant | | OD value (450 nm) |
|---|---|---|---|
| 1 | original | | 1.998 |
| 2 | L121 | I | 1.724 |
| 3 | | V | 1.299 |
| 4 | | A | 0.305 |
| 5 | | F | 0.476 |
| 6 | | P | 0.181 |
| 7 | W123 | Y | 1.043 |
| 8 | | F | 0.506 |
| 9 | | P | 0.044 |
| 10 | | L | 0.076 |
| 11 | | I | 0.075 |
| 12 | I124 | L | 1.419 |
| 13 | | M | 0.516 |
| 14 | | P | 0.044 |
| 15 | | V | 2.032 |
| 16 | | A | 0.071 |
| 17 | G126 | P | 0.063 |
| 18 | | A | 1.781 |
| 19 | | S | 1.855 |
| 20 | | N | 0.060 |
| 21 | | T | 1.194 |

Fig. 4

| Serial Number | Name of Variant | | OD value (450 nm) |
|---|---|---|---|
| 1 | original (P125) | | 2.04 |
| 2 | P125 | G | 0.053 |
| 3 | | I | 0.053 |
| 4 | | A | 0.060 |
| 5 | | L | 0.053 |
| 6 | | V | 0.058 |
| 7 | | S | 0.066 |
| 8 | | T | 0.064 |
| 9 | | N | 0.046 |
| 10 | | Q | 0.152 |
| 11 | | D | 0.050 |
| 12 | | E | 0.088 |
| 13 | | K | 0.048 |
| 14 | | H | 0.052 |
| 15 | | C | 0.050 |
| 16 | | M | 0.047 |
| 17 | | Y | 0.047 |
| 18 | | W | 0.048 |
| 19 | | F | 0.049 |

Fig. 5

| Serial Number | Name of Variant | | OD value (450 nm) |
|---|---|---|---|
| 1 | original | | 2.088 |
| 2 | V117 | L | 1.937 |
| 3 | | I | 1.98 |
| 4 | T118 | S | 2.147 |
| 5 | | K | 2.081 |
| 6 | R119 | K | 2.034 |
| 7 | | T | 1.855 |
| 8 | D120 | E | 1.887 |
| 9 | | A | 1.853 |
| 10 | E122 | D | 2.135 |
| 11 | | A | 1.989 |
| 12 | D127 | E | 2.101 |
| 13 | | A | 1.941 |
| 14 | Y128 | F | 1.948 |
| 15 | | W | 1.844 |
| 16 | Y129 | F | 1.933 |
| 17 | | W | 1.98 |
| 18 | M130 | F | 2.034 |
| 19 | | I | 2.058 |
| 20 | D131 | E | 2.092 |
| 21 | | A | 2.114 |
| 22 | V132 | Y | 2.217 |
| 23 | | S | 2.151 |

Fig. 6

| Serial Number | Name of Variant | OD value (450 nm) |
|---|---|---|
| 1 | original | 2.163 |
| 2 | I124V/G126A | 1.685 |
| 3 | I124V/G126S | 1.723 |
| 4 | L121I/W123Y/I124V/G126A | 1.079 |
| 5 | L121I/W123Y/I124V/G126S | 0.25 |

Fig. 7

| Serial Number | Name of Variant | OD value (450 nm) |
|---|---|---|
| 1 | original | 2.141 |
| 2 | E122del | 0.047 |
| 3 | G126_D127insE | 0.048 |

Fig. 8

| Serial Number | Name of Variant | OD value (450 nm) |
|---|---|---|
| 1 | N79 | 1.996 |
| 2 | N79Q | 1.869 |

Fig. 10

SEQUENCE LISTING

<160> NUMBER OF SEQ ID NOS: 137

<210> SEQ ID NO 1
<211> LENGTH: 1422
<212> TYPE: DNA
<213> ORGANISM: Homo sapiens

<400> SEQUENCE: 1

```
atgaagcatc tgtggttctt cctcctcctg gtggcagctc ccagatgggt cctgtcccag      60
gtgcagctac agcagtgggg cgcaggactg ttgaagcctt cggagaccct gtccctcacc     120
tgcgctgtct atggtgggtc cttcagtggt tactactggg gctggatccg ccagccccca     180
gggaaggggc tggagtggat tggggaaatc aatcatagtg gaagcgccaa ctccaacccg     240
tccctcaaga gtcgagtcac catgtcagta gacacgtcca agaaccagtt ctccctgaag     300
gtgagctctg tgaccgccgc ggacacggct gtgtatttct gtgcgagagt aacacgagat     360
ttggagtgga tacccggaga ctactacatg gacgtctggg gcaaagggac cacggtcacc     420
gtctcctcag cctccaccaa gggcccatcg gtcttccccc tggcaccctc ctccaagagc     480
acctctgggg gcacagcggc cctgggctgc ctggtcaagg actacttccc cgaaccggtg     540
acggtgtcgt ggaactcagg cgccctgacc agcggcgtgc acaccttccc ggctgtccta     600
cagtcctcag gactctattc cctcagcagc gtggtgaccg tgccctccag cagcttgggc     660
acccagacct acatctgcaa cgtgaatcac aagcccagca caccaaggt ggacaagaaa     720 gttgagccca aatcttgtga caaaactcac acatgcccac cgtgcccagc acctgaactc     780 ctgggggac cgtcagtctt cctcttcccc ccaaaaccca aggacaccct catgatctcc     840
cggacccctg aggtcacatg cgtggtggtg gacgtgagcc acgaagaccc tgaggtcaag     900
ttcaactggt acgtggacgg cgtggaggtg cataatgcca agacaaagcc gcgggaggag     960
cagtacaaca gcacgtaccg tgtggtcagc gtcctcaccg tcctgcacca ggactggctg    1020
aatggcaagg agtacaagtg caaggtctcc aacaaagccc tcccagcccc catcgagaaa    1080
accatctcca aagccaaagg gcagccccga gaaccacagg tgtacaccct gcccccatcc    1140
cgggatgagc tgaccaagaa ccaggtcagc ctgacctgcc tggtcaaagg cttctatccc    1200
```

```
agcgacatcg ccgtggagtg ggagagcaat gggcagccgg agaacaacta caagaccacg    1260
cctcccgtgc tggactccga cggctccttc ttcctctaca gcaagctcac cgtggacaag    1320
agcaggtggc agcaggggaa cgtcttctca tgctccgtga tgcatgaggg tctgcacaac    1380
cactacacgc agaagagcct ctccctgtct ccgggtaaat ga                        1422

<210> SEQ ID NO 2
<211> LENGTH: 473
<212> TYPE: PRT
<213> ORGANISM: Homo sapiens

<400> SEQUENCE: 2

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
            100                 105                 110

Phe Cys Ala Arg Val Thr Arg Asp Leu Glu Trp Ile Pro Gly Asp Tyr
        115                 120                 125

Tyr Met Asp Val Trp Gly Lys Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335
```

```
Gln Asp Trp Leu Asn Gly Lys Glu Tyr Lys Cys Lys Val Ser Asn Lys
            340                 345                 350
Ala Leu Pro Ala Pro Ile Glu Thr Ile Ser Lys Ala Lys Gly Gln
        355                 360                 365
Pro Arg Glu Pro Gln Val Tyr Thr Leu Pro Pro Ser Arg Asp Glu Leu
    370                 375                 380
Thr Lys Asn Gln Val Ser Leu Thr Cys Leu Val Lys Gly Phe Tyr Pro
385                 390                 395                 400
Ser Asp Ile Ala Val Glu Trp Glu Ser Asn Gly Gln Pro Glu Asn Asn
                405                 410                 415
Tyr Lys Thr Thr Pro Pro Val Leu Asp Ser Asp Gly Ser Phe Phe Leu
            420                 425                 430
Tyr Ser Lys Leu Thr Val Asp Lys Ser Arg Trp Gln Gln Gly Asn Val
        435                 440                 445
Phe Ser Cys Ser Val Met His Glu Gly Leu His Asn His Tyr Thr Gln
    450                 455                 460
Lys Ser Leu Ser Leu Ser Pro Gly Lys
465                 470
```

<210> SEQ ID NO 3
<211> LENGTH: 708
<212> TYPE: DNA
<213> ORGANISM: Homo sapiens

<400> SEQUENCE: 3

```
atggccggct tccctctcct cctcaccctc ctcactcact gtgcagggtc ctgggcccag    60
tctgtgctga ctcagccacc ctcagcgtct gggaccccg ggcagagggt cagcatctct   120
tgttctggaa gcctgtccaa catcggcact aattatgtat actggtacca gcaactccca   180
ggaacggccc ccaaactcct catctttaag aataatcagc ggccctcagg ggtccctgac   240
cgattctctg ctccaagtc tggcacctca gcctccctgg ccatcagtgg cctcggtcc    300
gaggatgagg ctgattatta ctgtgcagca tgggatgaca gcctgaatgg ttatgtcttc   360
ggaactggga ccaaggtcac cgtcctaggt cagcccaagg ccaacccac tgtcactctg    420
ttcccgccct cctctgagga gctccaagcc aacaaggcca cactagtgtg tctgatcagt   480
gacttctacc cgggagctgt gacagtggcc tggaaggcag atggcagccc cgtcaaggcg   540
ggagtggaga ccaccaaacc ctccaaacag agcaacaaca gtacgcggc cagcagctac    600
ctgagcctga cgcccgagca gtggaagtcc cacagaagct acagctgcca ggtcacacat   660
gaagggagca ccgtggagaa gacagtggcc cctacagaat gttcatag                 708
```

<210> SEQ ID NO 4
<211> LENGTH: 235
<212> TYPE: PRT
<213> ORGANISM: Homo sapiens

<400> SEQUENCE: 4

```
Met Ala Gly Phe Pro Leu Leu Leu Thr Leu Leu Thr His Cys Ala Gly
1               5                  10                  15
Ser Trp Ala Gln Ser Val Leu Thr Gln Pro Pro Ser Ala Ser Gly Thr
            20                  25                  30
Pro Gly Gln Arg Val Ser Ile Ser Cys Ser Gly Ser Leu Ser Asn Ile
        35                  40                  45
Gly Thr Asn Tyr Val Tyr Trp Tyr Gln Gln Leu Pro Gly Thr Ala Pro
    50                  55                  60
Lys Leu Leu Ile Phe Lys Asn Asn Gln Arg Pro Ser Gly Val Pro Asp
```

```
                65                  70                  75                  80
Arg Phe Ser Gly Ser Lys Ser Gly Thr Ser Ala Ser Leu Ala Ile Ser
                    85                  90                  95
Gly Leu Arg Ser Glu Asp Glu Ala Asp Tyr Tyr Cys Ala Ala Trp Asp
                    100                 105                 110
Asp Ser Leu Asn Gly Tyr Val Phe Gly Thr Gly Thr Lys Val Thr Val
                    115                 120                 125
Leu Gly Gln Pro Lys Ala Asn Pro Thr Val Thr Leu Phe Pro Pro Ser
        130                 135                 140
Ser Glu Glu Leu Gln Ala Asn Lys Ala Thr Leu Val Cys Leu Ile Ser
145                 150                 155                 160
Asp Phe Tyr Pro Gly Ala Val Thr Val Ala Trp Lys Ala Asp Gly Ser
                    165                 170                 175
Pro Val Lys Ala Gly Val Glu Thr Thr Lys Pro Ser Lys Gln Ser Asn
                    180                 185                 190
Asn Lys Tyr Ala Ala Ser Ser Tyr Leu Ser Leu Thr Pro Glu Gln Trp
                    195                 200                 205
Lys Ser His Arg Ser Tyr Ser Cys Gln Val Thr His Glu Gly Ser Thr
        210                 215                 220
Val Glu Lys Thr Val Ala Pro Thr Glu Cys Ser
225                 230                 235
```

<210> SEQ ID NO 5
<211> LENGTH: 1365
<212> TYPE: DNA
<213> ORGANISM: Homo sapiens

<400> SEQUENCE: 5

```
caggtgcagc tacagcagtg gggcgcagga ctgttgaagc cttcggagac cctgtccctc      60
acctgcgctg tctatggtgg gtccttcagt ggttactact ggggctggat ccgccagccc     120
ccagggaagg ggctggagtg gattgggaa atcaatcata gtggaagcgc caactccaac      180
ccgtccctca agagtcgagt caccatgtca gtagacacgt ccaagaacca gttctccctg     240
aaggtgagct ctgtgaccgc cgcggacacg gctgtgtatt tctgtgcgag agtaacacga     300
gatttggagt ggatacccgg agactactac atggacgtct ggggcaaagg gaccacggtc     360
accgtctcct cagcctccac caagggccca tcggtcttcc cctggcaccc tcctccaag    420
agcacctctg ggggcacagc ggccctgggc tgcctggtca aggactactt ccccgaaccg     480
gtgacggtgt cgtggaactc aggcgccctg accagcggcg tgcacacctt cccggctgtc     540
ctacagtcct caggactcta ttccctcagc agcgtggtga ccgtgccctc agcagcttg     600
ggcacccaga cctacatctg caacgtgaat cacaagccca gcaacaccaa ggtggacaag     660
aaagttgagc ccaaatcttg tgacaaaact cacacatgcc caccgtgccc agcacctgaa     720
ctcctggggg gaccgtcagt cttcctcttc cccccaaaac ccaaggacac cctcatgatc     780
tcccggaccc ctgaggtcac atgcgtggtg gtggacgtga gccacgaaga ccctgaggtc     840
aagttcaact ggtacgtgga cggcgtggag gtgcataatg ccaagacaaa gccgcgggag     900
gagcagtaca acagcacgta ccgtgtggtc agcgtcctca ccgtcctgca ccaggactgg     960
ctgaatggca aggagtacaa gtgcaaggtc tccaacaaag ccctcccagc ccccatcgag    1020
aaaaccatct ccaaagccaa agggcagccc cgagaaccac aggtgtacac cctgccccca    1080
tcccgggatg agctgaccaa gaaccaggtc agcctgacct gcctggtcaa aggcttctat    1140
cccagcgaca tcgccgtgga gtgggagagc aatgggcagc cggagaacaa ctacaagacc    1200
```

```
acgcctcccg tgctggactc cgacggctcc ttcttcctct acagcaagct caccgtggac       1260
aagagcaggt ggcagcaggg gaacgtcttc tcatgctccg tgatgcatga gggtctgcac       1320
aaccactaca cgcagaagag cctctccctg tctccgggta aatga                      1365

<210> SEQ ID NO 6
<211> LENGTH: 454
<212> TYPE: PRT
<213> ORGANISM: Homo sapiens

<400> SEQUENCE: 6

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Gly Trp Ile Arg Gln Pro Pro Gly Lys Gly Leu Glu Trp Ile
        35                  40                  45

Gly Glu Ile Asn His Ser Gly Ala Asn Ser Asn Pro Ser Leu Lys
    50                  55                  60

Ser Arg Val Thr Met Ser Val Asp Thr Ser Lys Asn Gln Phe Ser Leu
65                  70                  75                  80

Lys Val Ser Ser Val Thr Ala Ala Asp Thr Ala Val Tyr Phe Cys Ala
                85                  90                  95

Arg Val Thr Arg Asp Leu Glu Trp Ile Pro Gly Asp Tyr Tyr Met Asp
            100                 105                 110

Val Trp Gly Lys Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350
```

```
Pro Gln Val Tyr Thr Leu Pro Pro Ser Arg Asp Glu Leu Thr Lys Asn
            355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Gly Leu His Asn His Tyr Thr Gln Lys Ser Leu
            435                 440                 445

Ser Leu Ser Pro Gly Lys
        450

<210> SEQ ID NO 7
<211> LENGTH: 651
<212> TYPE: DNA
<213> ORGANISM: Homo sapiens

<400> SEQUENCE: 7
cagtctgtgc tgactcagcc accctcagcg tctgggaccc ccgggcagag ggtcagcatc      60
tcttgttctg gaagcctgtc caacatcggc actaattatg tatactggta ccagcaactc     120
ccaggaacgg cccccaaact cctcatcttt aagaataatc agcggccctc aggggtccct     180
gaccgattct ctggctccaa gtctggcacc tcagcctccc tggccatcag tggcctccgg     240
tccgaggatg aggctgatta ttactgtgca gcatgggatg acagcctgaa tggttatgtc     300
ttcggaactg ggaccaaggt caccgtccta ggtcagccca aggccaaccc cactgtcact     360
ctgttcccgc cctcctctga ggagctccaa gccaacaagg ccacactagt gtgtctgatc     420
agtgacttct acccgggagc tgtgacagtg gcctggaagg cagatggcag ccccgtcaag     480
gcgggagtgg agaccaccaa accctccaaa cagagcaaca acaagtacgc ggccagcagc     540
tacctgagcc tgacgcccga gcagtggaag tcccacagaa gctacagctg ccaggtcaca     600
catgaaggga gcaccgtgga agacagtgtg cccctacag aatgttcata g               651

<210> SEQ ID NO 8
<211> LENGTH: 216
<212> TYPE: PRT
<213> ORGANISM: Homo sapiens

<400> SEQUENCE: 8

Gln Ser Val Leu Thr Gln Pro Pro Ser Ala Ser Gly Thr Pro Gly Gln
1               5                   10                  15

Arg Val Ser Ile Ser Cys Ser Gly Ser Leu Ser Asn Ile Gly Thr Asn
            20                  25                  30

Tyr Val Tyr Trp Tyr Gln Gln Leu Pro Gly Thr Ala Pro Lys Leu Leu
        35                  40                  45

Ile Phe Lys Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu Gly Gln
            100                 105                 110
```

-continued

```
Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 9
<211> LENGTH: 372
<212> TYPE: DNA
<213> ORGANISM: Homo sapiens

<400> SEQUENCE: 9
caggtgcagc tacagcagtg gggcgcagga ctgttgaagc cttcggagac cctgtccctc      60
acctgcgctg tctatggtgg gtccttcagt ggttactact ggggctggat ccgccagccc     120
ccagggaagg gctggagtg gattgggaa atcaatcata gtggaagcgc caactccaac       180
ccgtccctca gagtcgagt caccatgtca gtagacacgt ccaagaacca gttctccctg      240
aaggtgagct ctgtgaccgc cgcggacacg gctgtgtatt tctgtgcgag agtaacacga     300
gatttggagt ggatacccgg agactactac atggacgtct ggggcaaagg gaccacggtc     360
accgtctcct ca                                                         372

<210> SEQ ID NO 10
<211> LENGTH: 124
<212> TYPE: PRT
<213> ORGANISM: Homo sapiens

<400> SEQUENCE: 10

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Gly Trp Ile Arg Gln Pro Pro Gly Lys Gly Leu Glu Trp Ile
        35                  40                  45

Gly Glu Ile Asn His Ser Gly Ser Ala Asn Ser Asn Pro Ser Leu Lys
    50                  55                  60

Ser Arg Val Thr Met Ser Val Asp Thr Ser Lys Asn Gln Phe Ser Leu
65                  70                  75                  80

Lys Val Ser Ser Val Thr Ala Ala Asp Thr Ala Val Tyr Phe Cys Ala
                85                  90                  95

Arg Val Thr Arg Asp Leu Glu Trp Ile Pro Gly Asp Tyr Tyr Met Asp
            100                 105                 110

Val Trp Gly Lys Gly Thr Thr Val Thr Val Ser Ser
        115                 120

<210> SEQ ID NO 11
<211> LENGTH: 330
<212> TYPE: DNA
<213> ORGANISM: Homo sapiens
```

-continued

<400> SEQUENCE: 11
cagtctgtgc tgactcagcc accctcagcg tctgggaccc ccgggcagag ggtcagcatc    60
tcttgttctg gaagcctgtc caacatcggc actaattatg tatactggta ccagcaactc   120
ccaggaacgg cccccaaact cctcatcttt aagaataatc agcggccctc agggggtccct   180 gaccgattct ctggctccaa gtctggcacc tcagcctccc tggccatcag tggcctccgg   240
tccgaggatg aggctgatta ttactgtgca gcatgggatg acagcctgaa tggttatgtc   300
ttcggaactg ggaccaaggt caccgtccta                                     330

<210> SEQ ID NO 12
<211> LENGTH: 110
<212> TYPE: PRT
<213> ORGANISM: Homo sapiens

<400> SEQUENCE: 12

Gln Ser Val Leu Thr Gln Pro Pro Ser Ala Ser Gly Thr Pro Gly Gln
1               5                   10                  15

Arg Val Ser Ile Ser Cys Ser Gly Ser Leu Ser Asn Ile Gly Thr Asn
            20                  25                  30

Tyr Val Tyr Trp Tyr Gln Gln Leu Pro Gly Thr Ala Pro Lys Leu Leu
        35                  40                  45

Ile Phe Lys Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu
            100                 105                 110

<210> SEQ ID NO 13
<211> LENGTH: 5
<212> TYPE: PRT
<213> ORGANISM: Homo sapiens

<400> SEQUENCE: 13

Gly Tyr Tyr Trp Gly
1               5

<210> SEQ ID NO 14
<211> LENGTH: 16
<212> TYPE: PRT
<213> ORGANISM: Homo sapiens

<400> SEQUENCE: 14

Glu Ile Asn His Ser Gly Ser Ala Asn Ser Asn Pro Ser Leu Lys Ser
1               5                   10                  15

<210> SEQ ID NO 15
<211> LENGTH: 16
<212> TYPE: PRT
<213> ORGANISM: Homo sapiens

<400> SEQUENCE: 15

Val Thr Arg Asp Leu Glu Trp Ile Pro Gly Asp Tyr Tyr Met Asp Val
1               5                   10                  15

<210> SEQ ID NO 16
<211> LENGTH: 13

```
<212> TYPE: PRT
<213> ORGANISM: Homo sapiens

<400> SEQUENCE: 16

Ser Gly Ser Leu Ser Asn Ile Gly Thr Asn Tyr Val Tyr
1               5                   10

<210> SEQ ID NO 17
<211> LENGTH: 7
<212> TYPE: PRT
<213> ORGANISM: Homo sapiens

<400> SEQUENCE: 17

Lys Asn Asn Gln Arg Pro Ser
1               5

<210> SEQ ID NO 18
<211> LENGTH: 11
<212> TYPE: PRT
<213> ORGANISM: Homo sapiens

<400> SEQUENCE: 18

Ala Ala Trp Asp Asp Ser Leu Asn Gly Tyr Val
1               5                   10

<210> SEQ ID NO 19
<211> LENGTH: 31
<212> TYPE: DNA
<213> ORGANISM: Artificial Sequence
<220> FEATURE:
<223> OTHER INFORMATION: 38 Hind-S

<400> SEQUENCE: 19
caccaagctt tgtgcaagaa catgaagcat c                                31

<210> SEQ ID NO 20
<211> LENGTH: 35
<212> TYPE: DNA
<213> ORGANISM: Artificial Sequence
<220> FEATURE:
<223> OTHER INFORMATION: 38 Not-A

<400> SEQUENCE: 20
ataagaatgc ggccgcgccg tcgcactcat ttacc                            35

<210> SEQ ID NO 21
<211> LENGTH: 21
<212> TYPE: DNA
<213> ORGANISM: Artificial Sequence
<220> FEATURE:
<223> OTHER INFORMATION: Primer

<400> SEQUENCE: 21
accagacata atagctgaca g                                           21

<210> SEQ ID NO 22
<211> LENGTH: 16
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (1)..(4)
<223> OTHER INFORMATION: Xaa can be any naturally occurring amino acid
<220> FEATURE:
<221> NAME/KEY: MISC_FEATURE
<222> LOCATION: (5)..(5)
```

```
<223> OTHER INFORMATION: Xaa is Leu, Ile, Val, Phe, or Ala
<220> FEATURE:
<221> NAME/KEY: MISC_FEATURE
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa is Trp, Tyr, or Phe
<220> FEATURE:
<221> NAME/KEY: MISC_FEATURE
<222> LOCATION: (8)..(8)
<223> OTHER INFORMATION: Xaa is Ile, Val, Leu, or Met
<220> FEATURE:
<221> NAME/KEY: MISC_FEATURE
<222> LOCATION: (10)..(10)
<223> OTHER INFORMATION: Xaa is Gly, Ser, Ala, or Thr
<220> FEATURE:
<221> NAME/KEY: MISC_FEATURE
<222> LOCATION: (11)..(16)
<223> OTHER INFORMATION: Xaa can be any naturally occuring amino acid

<400> SEQUENCE: 22

Xaa Xaa Xaa Xaa Xaa Xaa Xaa Xaa Pro Xaa Xaa Xaa Xaa Xaa Xaa
1               5                   10                  15

<210> SEQ ID NO 23
<211> LENGTH: 32
<212> TYPE: PRT
<213> ORGANISM: Human cytomegalovirus

<400> SEQUENCE: 23

Ser Cys Val Thr Ile Asn Gln Thr Ser Val Lys Val Leu Arg Asp Met
1               5                   10                  15

Asn Val Lys Glu Ser Pro Gly Arg Cys Tyr Ser Arg Pro Val Val Ile
            20                  25                  30

<210> SEQ ID NO 24
<211> LENGTH: 45
<212> TYPE: PRT
<213> ORGANISM: Human cytomegalovirus

<400> SEQUENCE: 24

Glu Asp Asn Glu Ile Leu Leu Gly Asn His Arg Thr Glu Glu Cys Gln
1               5                   10                  15

Leu Pro Ser Leu Lys Ile Phe Ile Ala Gly Asn Ser Ala Tyr Glu Tyr
            20                  25                  30

Val Asp Tyr Leu Phe Lys Arg Met Ile Asp Leu Ser Ser
        35                  40                  45

<210> SEQ ID NO 25
<211> LENGTH: 12
<212> TYPE: PRT
<213> ORGANISM: Human cytomegalovirus

<400> SEQUENCE: 25

Ser Cys Val Thr Ile Asn Gln Thr Ser Val Lys Val
1               5                   10

<210> SEQ ID NO 26
<211> LENGTH: 8
<212> TYPE: PRT
<213> ORGANISM: Human cytomegalovirus

<400> SEQUENCE: 26

Ser Pro Gly Arg Cys Tyr Ser Arg
1               5
```

<210> SEQ ID NO 27
<211> LENGTH: 8
<212> TYPE: PRT
<213> ORGANISM: Human cytomegalovirus

<400> SEQUENCE: 27

Tyr Glu Tyr Val Asp Tyr Leu Phe
1               5

<210> SEQ ID NO 28
<211> LENGTH: 473
<212> TYPE: PRT
<213> ORGANISM: Artificial
<220> FEATURE:
<223> OTHER INFORMATION: V117K

<400> SEQUENCE: 28

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
            100                 105                 110

Phe Cys Ala Arg Lys Thr Arg Asp Leu Glu Trp Ile Pro Gly Asp Tyr
        115                 120                 125

Tyr Met Asp Val Trp Gly Lys Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

```
Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Gly Leu His Asn His Tyr Thr Gln
    450                 455                 460

Lys Ser Leu Ser Leu Ser Pro Gly Lys
465                 470

<210> SEQ ID NO 29
<211> LENGTH: 473
<212> TYPE: PRT
<213> ORGANISM: Artificial
<220> FEATURE:
<223> OTHER INFORMATION: T118W

<400> SEQUENCE: 29

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
            100                 105                 110

Phe Cys Ala Arg Val Trp Arg Asp Leu Glu Trp Ile Pro Gly Asp Tyr
        115                 120                 125

Tyr Met Asp Val Trp Gly Lys Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205
```

```
Ser Ser Val Val Thr Val Pro Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Gly Leu His Asn His Tyr Thr Gln
450                 455                 460

Lys Ser Leu Ser Leu Ser Pro Gly Lys
465                 470

<210> SEQ ID NO 30
<211> LENGTH: 473
<212> TYPE: PRT
<213> ORGANISM: Artificial Sequence
<220> FEATURE:
<223> OTHER INFORMATION: R119V

<400> SEQUENCE: 30

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
```

```
            100                 105                 110
Phe Cys Ala Arg Val Thr Val Asp Leu Glu Trp Ile Pro Gly Asp Tyr
            115                 120                 125

Tyr Met Asp Val Trp Gly Lys Gly Thr Thr Val Thr Val Ser Ser Ala
            130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
            195                 200                 205

Ser Ser Val Val Thr Val Pro Ser Ser Ser Leu Gly Thr Gln Thr Tyr
            210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
            275                 280                 285

Val Val Asp Val Ser His Glu Asp Pro Glu Val Lys Phe Asn Trp Tyr
            290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
            355                 360                 365

Pro Arg Glu Pro Gln Val Tyr Thr Leu Pro Pro Ser Arg Asp Glu Leu
            370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
            435                 440                 445

Phe Ser Cys Ser Val Met His Glu Gly Leu His Asn His Tyr Thr Gln
            450                 455                 460

Lys Ser Leu Ser Leu Ser Pro Gly Lys
465                 470
```

<210> SEQ ID NO 31
<211> LENGTH: 473
<212> TYPE: PRT
<213> ORGANISM: Artificial Sequence
<220> FEATURE:
<223> OTHER INFORMATION: D120I

<400> SEQUENCE: 31

```
Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
            35                  40                  45

Ser Gly Tyr Tyr Trp Gly Trp Ile Arg Gln Pro Pro Gly Lys Gly Leu
        50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
            100                 105                 110

Phe Cys Ala Arg Val Thr Arg Ile Leu Glu Trp Ile Pro Gly Asp Tyr
            115                 120                 125

Tyr Met Asp Val Trp Gly Lys Gly Thr Thr Val Thr Val Ser Ser Ala
        130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
            195                 200                 205

Ser Ser Val Val Thr Val Pro Ser Ser Ser Leu Gly Thr Gln Thr Tyr
        210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
            275                 280                 285

Val Val Asp Val Ser His Glu Asp Pro Glu Val Lys Phe Asn Trp Tyr
        290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
            355                 360                 365

Pro Arg Glu Pro Gln Val Tyr Thr Leu Pro Pro Ser Arg Asp Glu Leu
        370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
```

```
                              420                 425                 430
Tyr Ser Lys Leu Thr Val Asp Lys Ser Arg Trp Gln Gln Gly Asn Val
            435                 440                 445
Phe Ser Cys Ser Val Met His Glu Gly Leu His Asn His Tyr Thr Gln
            450                 455                 460
Lys Ser Leu Ser Leu Ser Pro Gly Lys
465                 470

<210> SEQ ID NO 32
<211> LENGTH: 473
<212> TYPE: PRT
<213> ORGANISM: Artificial Sequence
<220> FEATURE:
<223> OTHER INFORMATION: L121E

<400> SEQUENCE: 32

Met Lys His Leu Trp Phe Phe Leu Leu Leu Val Ala Ala Pro Arg Trp
1               5                   10                  15
Val Leu Ser Gln Val Gln Leu Gln Gln Trp Gly Ala Gly Leu Leu Lys
            20                  25                  30
Pro Ser Glu Thr Leu Ser Leu Thr Cys Ala Val Tyr Gly Gly Ser Phe
        35                  40                  45
Ser Gly Tyr Tyr Trp Gly Trp Ile Arg Gln Pro Pro Gly Lys Gly Leu
    50                  55                  60
Glu Trp Ile Gly Glu Ile Asn His Ser Gly Ser Ala Asn Ser Asn Pro
65                  70                  75                  80
Ser Leu Lys Ser Arg Val Thr Met Ser Val Asp Thr Ser Lys Asn Gln
                85                  90                  95
Phe Ser Leu Lys Val Ser Ser Val Thr Ala Ala Asp Thr Ala Val Tyr
            100                 105                 110
Phe Cys Ala Arg Val Thr Arg Asp Glu Glu Trp Ile Pro Gly Asp Tyr
        115                 120                 125
Tyr Met Asp Val Trp Gly Lys Gly Thr Thr Val Thr Val Ser Ser Ala
    130                 135                 140
Ser Thr Lys Gly Pro Ser Val Phe Pro Leu Ala Pro Ser Ser Lys Ser
145                 150                 155                 160
Thr Ser Gly Gly Thr Ala Ala Leu Gly Cys Leu Val Lys Asp Tyr Phe
                165                 170                 175
Pro Glu Pro Val Thr Val Ser Trp Asn Ser Gly Ala Leu Thr Ser Gly
            180                 185                 190
Val His Thr Phe Pro Ala Val Leu Gln Ser Ser Gly Leu Tyr Ser Leu
        195                 200                 205
Ser Ser Val Val Thr Val Pro Ser Ser Ser Leu Gly Thr Gln Thr Tyr
    210                 215                 220
Ile Cys Asn Val Asn His Lys Pro Ser Asn Thr Lys Val Asp Lys Lys
225                 230                 235                 240
Val Glu Pro Lys Ser Cys Asp Lys Thr His Thr Cys Pro Pro Cys Pro
                245                 250                 255
Ala Pro Glu Leu Leu Gly Gly Pro Ser Val Phe Leu Phe Pro Pro Lys
            260                 265                 270
Pro Lys Asp Thr Leu Met Ile Ser Arg Thr Pro Glu Val Thr Cys Val
        275                 280                 285
Val Val Asp Val Ser His Glu Asp Pro Glu Val Lys Phe Asn Trp Tyr
    290                 295                 300
Val Asp Gly Val Glu Val His Asn Ala Lys Thr Lys Pro Arg Glu Glu
305                 310                 315                 320
```

```
Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Gly Leu His Asn His Tyr Thr Gln
    450                 455                 460

Lys Ser Leu Ser Leu Ser Pro Gly Lys
465                 470

<210> SEQ ID NO 33
<211> LENGTH: 473
<212> TYPE: PRT
<213> ORGANISM: Artificial Sequence
<220> FEATURE:
<223> OTHER INFORMATION: E122L

<400> SEQUENCE: 33

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
            100                 105                 110

Phe Cys Ala Arg Val Thr Arg Asp Leu Leu Trp Ile Pro Gly Asp Tyr
        115                 120                 125

Tyr Met Asp Val Trp Gly Lys Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205
```

Ser Ser Val Val Thr Val Pro Ser Ser Leu Gly Thr Gln Thr Tyr
210 215 220

Ile Cys Asn Val Asn His Lys Pro Ser Asn Thr Lys Val Asp Lys Lys
225 230 235 240

Val Glu Pro Lys Ser Cys Asp Lys Thr His Thr Cys Pro Pro Cys Pro
245 250 255

Ala Pro Glu Leu Leu Gly Gly Pro Ser Val Phe Leu Phe Pro Pro Lys
260 265 270

Pro Lys Asp Thr Leu Met Ile Ser Arg Thr Pro Glu Val Thr Cys Val
275 280 285

Val Val Asp Val Ser His Glu Asp Pro Glu Val Lys Phe Asn Trp Tyr
290 295 300

Val Asp Gly Val Glu Val His Asn Ala Lys Thr Lys Pro Arg Glu Glu
305 310 315 320

Gln Tyr Asn Ser Thr Tyr Arg Val Val Ser Val Leu Thr Val Leu His
325 330 335

Gln Asp Trp Leu Asn Gly Lys Glu Tyr Lys Cys Lys Val Ser Asn Lys
340 345 350

Ala Leu Pro Ala Pro Ile Glu Lys Thr Ile Ser Lys Ala Lys Gly Gln
355 360 365

Pro Arg Glu Pro Gln Val Tyr Thr Leu Pro Pro Ser Arg Asp Glu Leu
370 375 380

Thr Lys Asn Gln Val Ser Leu Thr Cys Leu Val Lys Gly Phe Tyr Pro
385 390 395 400

Ser Asp Ile Ala Val Glu Trp Glu Ser Asn Gly Gln Pro Glu Asn Asn
405 410 415

Tyr Lys Thr Thr Pro Pro Val Leu Asp Ser Asp Gly Ser Phe Phe Leu
420 425 430

Tyr Ser Lys Leu Thr Val Asp Lys Ser Arg Trp Gln Gln Gly Asn Val
435 440 445

Phe Ser Cys Ser Val Met His Glu Gly Leu His Asn His Tyr Thr Gln
450 455 460

Lys Ser Leu Ser Leu Ser Pro Gly Lys
465 470

<210> SEQ ID NO 34
<211> LENGTH: 473
<212> TYPE: PRT
<213> ORGANISM: Artificial Sequence
<220> FEATURE:
<223> OTHER INFORMATION: W123T

<400> SEQUENCE: 34

Met Lys His Leu Trp Phe Phe Leu Leu Leu Val Ala Ala Pro Arg Trp
1 5 10 15

Val Leu Ser Gln Val Gln Leu Gln Gln Trp Gly Ala Gly Leu Leu Lys
20 25 30

Pro Ser Glu Thr Leu Ser Leu Thr Cys Ala Val Tyr Gly Gly Ser Phe
35 40 45

Ser Gly Tyr Tyr Trp Gly Trp Ile Arg Gln Pro Pro Gly Lys Gly Leu
50 55 60

Glu Trp Ile Gly Glu Ile Asn His Ser Gly Ser Ala Asn Ser Asn Pro
65 70 75 80

Ser Leu Lys Ser Arg Val Thr Met Ser Val Asp Thr Ser Lys Asn Gln
85 90 95

Phe Ser Leu Lys Val Ser Ser Val Thr Ala Ala Asp Thr Ala Val Tyr

```
                100             105             110
    Phe Cys Ala Arg Val Thr Arg Asp Leu Glu Thr Ile Pro Gly Asp Tyr
                    115                 120                 125
    Tyr Met Asp Val Trp Gly Lys Gly Thr Thr Val Thr Val Ser Ser Ala
            130                 135                 140
    Ser Thr Lys Gly Pro Ser Val Phe Pro Leu Ala Pro Ser Ser Lys Ser
    145                 150                 155                 160
    Thr Ser Gly Gly Thr Ala Ala Leu Gly Cys Leu Val Lys Asp Tyr Phe
                    165                 170                 175
    Pro Glu Pro Val Thr Val Ser Trp Asn Ser Gly Ala Leu Thr Ser Gly
                180                 185                 190
    Val His Thr Phe Pro Ala Val Leu Gln Ser Ser Gly Leu Tyr Ser Leu
                    195                 200                 205
    Ser Ser Val Val Thr Val Pro Ser Ser Ser Leu Gly Thr Gln Thr Tyr
        210                 215                 220
    Ile Cys Asn Val Asn His Lys Pro Ser Asn Thr Lys Val Asp Lys Lys
    225                 230                 235                 240
    Val Glu Pro Lys Ser Cys Asp Lys Thr His Thr Cys Pro Pro Cys Pro
                    245                 250                 255
    Ala Pro Glu Leu Leu Gly Gly Pro Ser Val Phe Leu Phe Pro Pro Lys
                260                 265                 270
    Pro Lys Asp Thr Leu Met Ile Ser Arg Thr Pro Glu Val Thr Cys Val
                    275                 280                 285
    Val Val Asp Val Ser His Glu Asp Pro Glu Val Lys Phe Asn Trp Tyr
        290                 295                 300
    Val Asp Gly Val Glu Val His Asn Ala Lys Thr Lys Pro Arg Glu Glu
    305                 310                 315                 320
    Gln Tyr Asn Ser Thr Tyr Arg Val Val Ser Val Leu Thr Val Leu His
                    325                 330                 335
    Gln Asp Trp Leu Asn Gly Lys Glu Tyr Lys Cys Lys Val Ser Asn Lys
                340                 345                 350
    Ala Leu Pro Ala Pro Ile Glu Lys Thr Ile Ser Lys Ala Lys Gly Gln
                    355                 360                 365
    Pro Arg Glu Pro Gln Val Tyr Thr Leu Pro Pro Ser Arg Asp Glu Leu
        370                 375                 380
    Thr Lys Asn Gln Val Ser Leu Thr Cys Leu Val Lys Gly Phe Tyr Pro
    385                 390                 395                 400
    Ser Asp Ile Ala Val Glu Trp Glu Ser Asn Gly Gln Pro Glu Asn Asn
                    405                 410                 415
    Tyr Lys Thr Thr Pro Pro Val Leu Asp Ser Asp Gly Ser Phe Phe Leu
                420                 425                 430
    Tyr Ser Lys Leu Thr Val Asp Lys Ser Arg Trp Gln Gln Gly Asn Val
                    435                 440                 445
    Phe Ser Cys Ser Val Met His Glu Gly Leu His Asn His Tyr Thr Gln
                450                 455                 460
    Lys Ser Leu Ser Leu Ser Pro Gly Lys
    465                 470

<210> SEQ ID NO 35
<211> LENGTH: 473
<212> TYPE: PRT
<213> ORGANISM: Artificial Sequence
<220> FEATURE:
<223> OTHER INFORMATION: I124D

<400> SEQUENCE: 35
```

```
Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
            35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
            100                 105                 110

Phe Cys Ala Arg Val Thr Arg Asp Leu Glu Trp Asp Pro Gly Asp Tyr
        115                 120                 125

Tyr Met Asp Val Trp Gly Lys Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
```

```
                        420                 425                 430
Tyr Ser Lys Leu Thr Val Asp Lys Ser Arg Trp Gln Gln Gly Asn Val
                435                 440                 445
Phe Ser Cys Ser Val Met His Glu Gly Leu His Asn His Tyr Thr Gln
            450                 455                 460
Lys Ser Leu Ser Leu Ser Pro Gly Lys
465                 470

<210> SEQ ID NO 36
<211> LENGTH: 473
<212> TYPE: PRT
<213> ORGANISM: Artificial Sequence
<220> FEATURE:
<223> OTHER INFORMATION: P125R

<400> SEQUENCE: 36

Met Lys His Leu Trp Phe Phe Leu Leu Leu Val Ala Ala Pro Arg Trp
1               5                   10                  15
Val Leu Ser Gln Val Gln Leu Gln Gln Trp Gly Ala Gly Leu Leu Lys
                20                  25                  30
Pro Ser Glu Thr Leu Ser Leu Thr Cys Ala Val Tyr Gly Gly Ser Phe
            35                  40                  45
Ser Gly Tyr Tyr Trp Gly Trp Ile Arg Gln Pro Pro Gly Lys Gly Leu
        50                  55                  60
Glu Trp Ile Gly Glu Ile Asn His Ser Gly Ser Ala Asn Ser Asn Pro
65                  70                  75                  80
Ser Leu Lys Ser Arg Val Thr Met Ser Val Asp Thr Ser Lys Asn Gln
                85                  90                  95
Phe Ser Leu Lys Val Ser Ser Val Thr Ala Ala Asp Thr Ala Val Tyr
            100                 105                 110
Phe Cys Ala Arg Val Thr Arg Asp Leu Glu Trp Ile Arg Gly Asp Tyr
        115                 120                 125
Tyr Met Asp Val Trp Gly Lys Gly Thr Thr Val Thr Val Ser Ser Ala
130                 135                 140
Ser Thr Lys Gly Pro Ser Val Phe Pro Leu Ala Pro Ser Ser Lys Ser
145                 150                 155                 160
Thr Ser Gly Gly Thr Ala Ala Leu Gly Cys Leu Val Lys Asp Tyr Phe
                165                 170                 175
Pro Glu Pro Val Thr Val Ser Trp Asn Ser Gly Ala Leu Thr Ser Gly
            180                 185                 190
Val His Thr Phe Pro Ala Val Leu Gln Ser Ser Gly Leu Tyr Ser Leu
        195                 200                 205
Ser Ser Val Val Thr Val Pro Ser Ser Ser Leu Gly Thr Gln Thr Tyr
210                 215                 220
Ile Cys Asn Val Asn His Lys Pro Ser Asn Thr Lys Val Asp Lys Lys
225                 230                 235                 240
Val Glu Pro Lys Ser Cys Asp Lys Thr His Thr Cys Pro Pro Cys Pro
                245                 250                 255
Ala Pro Glu Leu Leu Gly Gly Pro Ser Val Phe Leu Phe Pro Pro Lys
            260                 265                 270
Pro Lys Asp Thr Leu Met Ile Ser Arg Thr Pro Glu Val Thr Cys Val
        275                 280                 285
Val Val Asp Val Ser His Glu Asp Pro Glu Val Lys Phe Asn Trp Tyr
        290                 295                 300
Val Asp Gly Val Glu Val His Asn Ala Lys Thr Lys Pro Arg Glu Glu
305                 310                 315                 320
```

```
Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Gly Leu His Asn His Tyr Thr Gln
    450                 455                 460

Lys Ser Leu Ser Leu Ser Pro Gly Lys
465                 470

<210> SEQ ID NO 37
<211> LENGTH: 473
<212> TYPE: PRT
<213> ORGANISM: Artificial Sequence
<220> FEATURE:
<223> OTHER INFORMATION: G126F

<400> SEQUENCE: 37

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
            100                 105                 110

Phe Cys Ala Arg Val Thr Arg Asp Leu Glu Trp Ile Pro Phe Asp Tyr
        115                 120                 125

Tyr Met Asp Val Trp Gly Lys Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205
```

```
Ser Ser Val Val Thr Val Pro Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Gly Leu His Asn His Tyr Thr Gln
    450                 455                 460

Lys Ser Leu Ser Leu Ser Pro Gly Lys
465                 470

<210> SEQ ID NO 38
<211> LENGTH: 473
<212> TYPE: PRT
<213> ORGANISM: Artificial Sequence
<220> FEATURE:
<223> OTHER INFORMATION: D127I

<400> SEQUENCE: 38

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
```

```
            100                 105                 110
Phe Cys Ala Arg Val Thr Arg Asp Leu Glu Trp Ile Pro Gly Ile Tyr
            115                 120                 125

Tyr Met Asp Val Trp Gly Lys Gly Thr Thr Val Thr Val Ser Ser Ala
        130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
        210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
        290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
        370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Gly Leu His Asn His Tyr Thr Gln
        450                 455                 460

Lys Ser Leu Ser Leu Ser Pro Gly Lys
465                 470

<210> SEQ ID NO 39
<211> LENGTH: 473
<212> TYPE: PRT
<213> ORGANISM: Artificial Sequence
<220> FEATURE:
<223> OTHER INFORMATION: Y128N

<400> SEQUENCE: 39
```

```
Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
            35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
            100                 105                 110

Phe Cys Ala Arg Val Thr Arg Asp Leu Glu Trp Ile Pro Gly Asp Asn
        115                 120                 125

Tyr Met Asp Val Trp Gly Lys Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
```

```
                       420                 425                 430
Tyr Ser Lys Leu Thr Val Asp Lys Ser Arg Trp Gln Gln Gly Asn Val
                435                 440                 445
Phe Ser Cys Ser Val Met His Glu Gly Leu His Asn His Tyr Thr Gln
            450                 455                 460
Lys Ser Leu Ser Leu Ser Pro Gly Lys
465                 470

<210> SEQ ID NO 40
<211> LENGTH: 473
<212> TYPE: PRT
<213> ORGANISM: Artificial Sequence
<220> FEATURE:
<223> OTHER INFORMATION: Y129N

<400> SEQUENCE: 40

Met Lys His Leu Trp Phe Phe Leu Leu Leu Val Ala Ala Pro Arg Trp
1               5                   10                  15
Val Leu Ser Gln Val Gln Leu Gln Gln Trp Gly Ala Gly Leu Leu Lys
            20                  25                  30
Pro Ser Glu Thr Leu Ser Leu Thr Cys Ala Val Tyr Gly Gly Ser Phe
        35                  40                  45
Ser Gly Tyr Tyr Trp Gly Trp Ile Arg Gln Pro Pro Gly Lys Gly Leu
    50                  55                  60
Glu Trp Ile Gly Glu Ile Asn His Ser Gly Ser Ala Asn Ser Asn Pro
65                  70                  75                  80
Ser Leu Lys Ser Arg Val Thr Met Ser Val Asp Thr Ser Lys Asn Gln
                85                  90                  95
Phe Ser Leu Lys Val Ser Ser Val Thr Ala Ala Asp Thr Ala Val Tyr
            100                 105                 110
Phe Cys Ala Arg Val Thr Arg Asp Leu Glu Trp Ile Pro Gly Asp Tyr
        115                 120                 125
Asn Met Asp Val Trp Gly Lys Gly Thr Thr Val Thr Val Ser Ser Ala
    130                 135                 140
Ser Thr Lys Gly Pro Ser Val Phe Pro Leu Ala Pro Ser Ser Lys Ser
145                 150                 155                 160
Thr Ser Gly Gly Thr Ala Ala Leu Gly Cys Leu Val Lys Asp Tyr Phe
                165                 170                 175
Pro Glu Pro Val Thr Val Ser Trp Asn Ser Gly Ala Leu Thr Ser Gly
            180                 185                 190
Val His Thr Phe Pro Ala Val Leu Gln Ser Ser Gly Leu Tyr Ser Leu
        195                 200                 205
Ser Ser Val Val Thr Val Pro Ser Ser Ser Leu Gly Thr Gln Thr Tyr
    210                 215                 220
Ile Cys Asn Val Asn His Lys Pro Ser Asn Thr Lys Val Asp Lys Lys
225                 230                 235                 240
Val Glu Pro Lys Ser Cys Asp Lys Thr His Thr Cys Pro Pro Cys Pro
                245                 250                 255
Ala Pro Glu Leu Leu Gly Gly Pro Ser Val Phe Leu Phe Pro Pro Lys
            260                 265                 270
Pro Lys Asp Thr Leu Met Ile Ser Arg Thr Pro Glu Val Thr Cys Val
        275                 280                 285
Val Val Asp Val Ser His Glu Asp Pro Glu Val Lys Phe Asn Trp Tyr
    290                 295                 300
Val Asp Gly Val Glu Val His Asn Ala Lys Thr Lys Pro Arg Glu Glu
305                 310                 315                 320
```

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
                340                 345                 350

Ala Leu Pro Ala Pro Ile Glu Lys Thr Ile Ser Lys Ala Lys Gly Gln
                355                 360                 365

Pro Arg Glu Pro Gln Val Tyr Thr Leu Pro Pro Ser Arg Asp Glu Leu
370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
                420                 425                 430

Tyr Ser Lys Leu Thr Val Asp Lys Ser Arg Trp Gln Gln Gly Asn Val
                435                 440                 445

Phe Ser Cys Ser Val Met His Glu Gly Leu His Asn His Tyr Thr Gln
                450                 455                 460

Lys Ser Leu Ser Leu Ser Pro Gly Lys
465                 470

<210> SEQ ID NO 41
<211> LENGTH: 473
<212> TYPE: PRT
<213> ORGANISM: Artificial Sequence
<220> FEATURE:
<223> OTHER INFORMATION: M130Q

<400> SEQUENCE: 41

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
                20                  25                  30

Pro Ser Glu Thr Leu Ser Leu Thr Cys Ala Val Tyr Gly Gly Ser Phe
                35                  40                  45

Ser Gly Tyr Tyr Trp Gly Trp Ile Arg Gln Pro Pro Gly Lys Gly Leu
            50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
                100                 105                 110

Phe Cys Ala Arg Val Thr Arg Asp Leu Glu Trp Ile Pro Gly Asp Tyr
                115                 120                 125

Tyr Gln Asp Val Trp Gly Lys Gly Thr Thr Val Thr Val Ser Ser Ala
            130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
                180                 185                 190

Val His Thr Phe Pro Ala Val Leu Gln Ser Ser Gly Leu Tyr Ser Leu
                195                 200                 205

Ser Ser Val Val Thr Val Pro Ser Ser Leu Gly Thr Gln Thr Tyr
            210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Gly Leu His Asn His Tyr Thr Gln
450                 455                 460

Lys Ser Leu Ser Leu Ser Pro Gly Lys
465                 470

<210> SEQ ID NO 42
<211> LENGTH: 473
<212> TYPE: PRT
<213> ORGANISM: Artificial Sequence
<220> FEATURE:
<223> OTHER INFORMATION: D131I

<400> SEQUENCE: 42

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr

```
                100             105                 110
        Phe Cys Ala Arg Val Thr Arg Asp Leu Glu Trp Ile Pro Gly Asp Tyr
                    115                 120                 125

Tyr Met Ile Val Trp Gly Lys Gly Thr Thr Val Thr Val Ser Ser Ala
                    130                 135                 140

Ser Thr Lys Gly Pro Ser Val Phe Pro Leu Ala Pro Ser Ser Lys Ser
        145                 150                 155                 160

Thr Ser Gly Gly Thr Ala Ala Leu Gly Cys Leu Val Lys Asp Tyr Phe
                        165                 170                 175

Pro Glu Pro Val Thr Val Ser Trp Asn Ser Gly Ala Leu Thr Ser Gly
                    180                 185                 190

Val His Thr Phe Pro Ala Val Leu Gln Ser Ser Gly Leu Tyr Ser Leu
                    195                 200                 205

Ser Ser Val Val Thr Val Pro Ser Ser Ser Leu Gly Thr Gln Thr Tyr
                    210                 215                 220

Ile Cys Asn Val Asn His Lys Pro Ser Asn Thr Lys Val Asp Lys Lys
        225                 230                 235                 240

Val Glu Pro Lys Ser Cys Asp Lys Thr His Thr Cys Pro Pro Cys Pro
                        245                 250                 255

Ala Pro Glu Leu Leu Gly Gly Pro Ser Val Phe Leu Phe Pro Pro Lys
                        260                 265                 270

Pro Lys Asp Thr Leu Met Ile Ser Arg Thr Pro Glu Val Thr Cys Val
                    275                 280                 285

Val Val Asp Val Ser His Glu Asp Pro Glu Val Lys Phe Asn Trp Tyr
                    290                 295                 300

Val Asp Gly Val Glu Val His Asn Ala Lys Thr Lys Pro Arg Glu Glu
        305                 310                 315                 320

Gln Tyr Asn Ser Thr Tyr Arg Val Val Ser Val Leu Thr Val Leu His
                        325                 330                 335

Gln Asp Trp Leu Asn Gly Lys Glu Tyr Lys Cys Lys Val Ser Asn Lys
                        340                 345                 350

Ala Leu Pro Ala Pro Ile Glu Lys Thr Ile Ser Lys Ala Lys Gly Gln
                    355                 360                 365

Pro Arg Glu Pro Gln Val Tyr Thr Leu Pro Pro Ser Arg Asp Glu Leu
                    370                 375                 380

Thr Lys Asn Gln Val Ser Leu Thr Cys Leu Val Lys Gly Phe Tyr Pro
        385                 390                 395                 400

Ser Asp Ile Ala Val Glu Trp Glu Ser Asn Gly Gln Pro Glu Asn Asn
                        405                 410                 415

Tyr Lys Thr Thr Pro Pro Val Leu Asp Ser Asp Gly Ser Phe Phe Leu
                        420                 425                 430

Tyr Ser Lys Leu Thr Val Asp Lys Ser Arg Trp Gln Gln Gly Asn Val
                    435                 440                 445

Phe Ser Cys Ser Val Met His Glu Gly Leu His Asn His Tyr Thr Gln
                    450                 455                 460

Lys Ser Leu Ser Leu Ser Pro Gly Lys
        465                 470

<210> SEQ ID NO 43
<211> LENGTH: 473
<212> TYPE: PRT
<213> ORGANISM: Artificial Sequence
<220> FEATURE:
<223> OTHER INFORMATION: V132K

<400> SEQUENCE: 43
```

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
            35                  40                  45

Ser Gly Tyr Tyr Trp Gly Trp Ile Arg Gln Pro Pro Gly Lys Gly Leu
50                      55                  60

Glu Trp Ile Gly Glu Ile Asn His Ser Gly Ser Ala Asn Ser Asn Pro
65              70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
            100                 105                 110

Phe Cys Ala Arg Val Thr Arg Asp Leu Glu Trp Ile Pro Gly Asp Tyr
    115                 120                 125

Tyr Met Asp Lys Trp Gly Lys Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
    275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
        370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu

-continued

```
                      420                 425                 430
Tyr Ser Lys Leu Thr Val Asp Lys Ser Arg Trp Gln Gln Gly Asn Val
                435                 440                 445

Phe Ser Cys Ser Val Met His Glu Gly Leu His Asn His Tyr Thr Gln
    450                 455                 460

Lys Ser Leu Ser Leu Ser Pro Gly Lys
465                 470

<210> SEQ ID NO 44
<211> LENGTH: 473
<212> TYPE: PRT
<213> ORGANISM: Artificial Sequence
<220> FEATURE:
<223> OTHER INFORMATION: L121I

<400> SEQUENCE: 44

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
                20                  25                  30

Pro Ser Glu Thr Leu Ser Leu Thr Cys Ala Val Tyr Gly Gly Ser Phe
            35                  40                  45

Ser Gly Tyr Tyr Trp Gly Trp Ile Arg Gln Pro Pro Gly Lys Gly Leu
        50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
            100                 105                 110

Phe Cys Ala Arg Val Thr Arg Asp Ile Glu Trp Ile Pro Gly Asp Tyr
        115                 120                 125

Tyr Met Asp Val Trp Gly Lys Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320
```

```
Gln Tyr Asn Ser Thr Tyr Arg Val Val Ser Val Leu Thr Val Leu His
                325                 330                 335
Gln Asp Trp Leu Asn Gly Lys Glu Tyr Lys Cys Lys Val Ser Asn Lys
            340                 345                 350
Ala Leu Pro Ala Pro Ile Glu Lys Thr Ile Ser Lys Ala Lys Gly Gln
        355                 360                 365
Pro Arg Glu Pro Gln Val Tyr Thr Leu Pro Pro Ser Arg Asp Glu Leu
    370                 375                 380
Thr Lys Asn Gln Val Ser Leu Thr Cys Leu Val Lys Gly Phe Tyr Pro
385                 390                 395                 400
Ser Asp Ile Ala Val Glu Trp Glu Ser Asn Gly Gln Pro Glu Asn Asn
                405                 410                 415
Tyr Lys Thr Thr Pro Pro Val Leu Asp Ser Asp Gly Ser Phe Phe Leu
            420                 425                 430
Tyr Ser Lys Leu Thr Val Asp Lys Ser Arg Trp Gln Gln Gly Asn Val
        435                 440                 445
Phe Ser Cys Ser Val Met His Glu Gly Leu His Asn His Tyr Thr Gln
    450                 455                 460
Lys Ser Leu Ser Leu Ser Pro Gly Lys
465                 470

<210> SEQ ID NO 45
<211> LENGTH: 473
<212> TYPE: PRT
<213> ORGANISM: Artificial Sequence
<220> FEATURE:
<223> OTHER INFORMATION: L121V

<400> SEQUENCE: 45

Met Lys His Leu Trp Phe Phe Leu Leu Leu Val Ala Ala Pro Arg Trp
1               5                   10                  15
Val Leu Ser Gln Val Gln Leu Gln Gln Trp Gly Ala Gly Leu Leu Lys
            20                  25                  30
Pro Ser Glu Thr Leu Ser Leu Thr Cys Ala Val Tyr Gly Gly Ser Phe
        35                  40                  45
Ser Gly Tyr Tyr Trp Gly Trp Ile Arg Gln Pro Pro Gly Lys Gly Leu
    50                  55                  60
Glu Trp Ile Gly Glu Ile Asn His Ser Gly Ser Ala Asn Ser Asn Pro
65                  70                  75                  80
Ser Leu Lys Ser Arg Val Thr Met Ser Val Asp Thr Ser Lys Asn Gln
                85                  90                  95
Phe Ser Leu Lys Val Ser Ser Val Thr Ala Ala Asp Thr Ala Val Tyr
            100                 105                 110
Phe Cys Ala Arg Val Thr Arg Asp Val Glu Trp Ile Pro Gly Asp Tyr
        115                 120                 125
Tyr Met Asp Val Trp Gly Lys Gly Thr Thr Val Thr Val Ser Ser Ala
    130                 135                 140
Ser Thr Lys Gly Pro Ser Val Phe Pro Leu Ala Pro Ser Ser Lys Ser
145                 150                 155                 160
Thr Ser Gly Gly Thr Ala Ala Leu Gly Cys Leu Val Lys Asp Tyr Phe
                165                 170                 175
Pro Glu Pro Val Thr Val Ser Trp Asn Ser Gly Ala Leu Thr Ser Gly
            180                 185                 190
Val His Thr Phe Pro Ala Val Leu Gln Ser Ser Gly Leu Tyr Ser Leu
        195                 200                 205
```

```
Ser Ser Val Val Thr Val Pro Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Gly Leu His Asn His Tyr Thr Gln
    450                 455                 460

Lys Ser Leu Ser Leu Ser Pro Gly Lys
465                 470

<210> SEQ ID NO 46
<211> LENGTH: 473
<212> TYPE: PRT
<213> ORGANISM: Artificial Sequence
<220> FEATURE:
<223> OTHER INFORMATION: L121A

<400> SEQUENCE: 46

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
```

```
                    100                 105                 110
Phe Cys Ala Arg Val Thr Arg Asp Ala Glu Trp Ile Pro Gly Asp Tyr
            115                 120                 125

Tyr Met Asp Val Trp Gly Lys Gly Thr Thr Val Thr Val Ser Ser Ala
        130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
            195                 200                 205

Ser Ser Val Val Thr Val Pro Ser Ser Ser Leu Gly Thr Gln Thr Tyr
        210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
            275                 280                 285

Val Val Asp Val Ser His Glu Asp Pro Glu Val Lys Phe Asn Trp Tyr
        290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
            355                 360                 365

Pro Arg Glu Pro Gln Val Tyr Thr Leu Pro Pro Ser Arg Asp Glu Leu
        370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Gly Leu His Asn His Tyr Thr Gln
        450                 455                 460

Lys Ser Leu Ser Leu Ser Pro Gly Lys
465                 470

<210> SEQ ID NO 47
<211> LENGTH: 473
<212> TYPE: PRT
<213> ORGANISM: Artificial Sequence
<220> FEATURE:
<223> OTHER INFORMATION: L121F

<400> SEQUENCE: 47
```

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
            35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
            100                 105                 110

Phe Cys Ala Arg Val Thr Arg Asp Phe Glu Trp Ile Pro Gly Asp Tyr
            115                 120                 125

Tyr Met Asp Val Trp Gly Lys Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
            195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
            275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
            355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu

```
                                    420                 425                 430
Tyr Ser Lys Leu Thr Val Asp Lys Ser Arg Trp Gln Gln Gly Asn Val
                435                 440                 445

Phe Ser Cys Ser Val Met His Glu Gly Leu His Asn His Tyr Thr Gln
                450                 455                 460

Lys Ser Leu Ser Leu Ser Pro Gly Lys
465                 470

<210> SEQ ID NO 48
<211> LENGTH: 473
<212> TYPE: PRT
<213> ORGANISM: Artificial Sequence
<220> FEATURE:
<223> OTHER INFORMATION: L121P

<400> SEQUENCE: 48

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
                20                  25                  30

Pro Ser Glu Thr Leu Ser Leu Thr Cys Ala Val Tyr Gly Gly Ser Phe
            35                  40                  45

Ser Gly Tyr Tyr Trp Gly Trp Ile Arg Gln Pro Pro Gly Lys Gly Leu
        50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
            100                 105                 110

Phe Cys Ala Arg Val Thr Arg Asp Pro Glu Trp Ile Pro Gly Asp Tyr
        115                 120                 125

Tyr Met Asp Val Trp Gly Lys Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320
```

```
Gln Tyr Asn Ser Thr Tyr Arg Val Val Ser Val Leu Thr Val Leu His
                325                 330                 335
Gln Asp Trp Leu Asn Gly Lys Glu Tyr Lys Cys Lys Val Ser Asn Lys
            340                 345                 350
Ala Leu Pro Ala Pro Ile Glu Lys Thr Ile Ser Lys Ala Lys Gly Gln
        355                 360                 365
Pro Arg Glu Pro Gln Val Tyr Thr Leu Pro Pro Ser Arg Asp Glu Leu
    370                 375                 380
Thr Lys Asn Gln Val Ser Leu Thr Cys Leu Val Lys Gly Phe Tyr Pro
385                 390                 395                 400
Ser Asp Ile Ala Val Glu Trp Glu Ser Asn Gly Gln Pro Glu Asn Asn
                405                 410                 415
Tyr Lys Thr Thr Pro Pro Val Leu Asp Ser Asp Gly Ser Phe Phe Leu
            420                 425                 430
Tyr Ser Lys Leu Thr Val Asp Lys Ser Arg Trp Gln Gln Gly Asn Val
        435                 440                 445
Phe Ser Cys Ser Val Met His Glu Gly Leu His Asn His Tyr Thr Gln
    450                 455                 460
Lys Ser Leu Ser Leu Ser Pro Gly Lys
465                 470

<210> SEQ ID NO 49
<211> LENGTH: 473
<212> TYPE: PRT
<213> ORGANISM: Artificial Sequence
<220> FEATURE:
<223> OTHER INFORMATION: W123Y

<400> SEQUENCE: 49

Met Lys His Leu Trp Phe Phe Leu Leu Leu Val Ala Ala Pro Arg Trp
1               5                   10                  15
Val Leu Ser Gln Val Gln Leu Gln Gln Trp Gly Ala Gly Leu Leu Lys
            20                  25                  30
Pro Ser Glu Thr Leu Ser Leu Thr Cys Ala Val Tyr Gly Gly Ser Phe
        35                  40                  45
Ser Gly Tyr Tyr Trp Gly Trp Ile Arg Gln Pro Pro Gly Lys Gly Leu
    50                  55                  60
Glu Trp Ile Gly Glu Ile Asn His Ser Gly Ser Ala Asn Ser Asn Pro
65                  70                  75                  80
Ser Leu Lys Ser Arg Val Thr Met Ser Val Asp Thr Ser Lys Asn Gln
                85                  90                  95
Phe Ser Leu Lys Val Ser Ser Val Thr Ala Ala Asp Thr Ala Val Tyr
            100                 105                 110
Phe Cys Ala Arg Val Thr Arg Asp Leu Glu Tyr Ile Pro Gly Asp Tyr
        115                 120                 125
Tyr Met Asp Val Trp Gly Lys Gly Thr Thr Val Thr Val Ser Ser Ala
    130                 135                 140
Ser Thr Lys Gly Pro Ser Val Phe Pro Leu Ala Pro Ser Ser Lys Ser
145                 150                 155                 160
Thr Ser Gly Gly Thr Ala Ala Leu Gly Cys Leu Val Lys Asp Tyr Phe
                165                 170                 175
Pro Glu Pro Val Thr Val Ser Trp Asn Ser Gly Ala Leu Thr Ser Gly
            180                 185                 190
Val His Thr Phe Pro Ala Val Leu Gln Ser Ser Gly Leu Tyr Ser Leu
        195                 200                 205
```

Ser Ser Val Val Thr Val Pro Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Gly Leu His Asn His Tyr Thr Gln
    450                 455                 460

Lys Ser Leu Ser Leu Ser Pro Gly Lys
465                 470

<210> SEQ ID NO 50
<211> LENGTH: 473
<212> TYPE: PRT
<213> ORGANISM: Artificial Sequence
<220> FEATURE:
<223> OTHER INFORMATION: W123F

<400> SEQUENCE: 50

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr

```
                    100                 105                 110
Phe Cys Ala Arg Val Thr Arg Asp Leu Glu Phe Ile Pro Gly Asp Tyr
            115                 120                 125
Tyr Met Asp Val Trp Gly Lys Gly Thr Thr Val Thr Val Ser Ser Ala
    130                 135                 140
Ser Thr Lys Gly Pro Ser Val Phe Pro Leu Ala Pro Ser Ser Lys Ser
145                 150                 155                 160
Thr Ser Gly Gly Thr Ala Ala Leu Gly Cys Leu Val Lys Asp Tyr Phe
                165                 170                 175
Pro Glu Pro Val Thr Val Ser Trp Asn Ser Gly Ala Leu Thr Ser Gly
            180                 185                 190
Val His Thr Phe Pro Ala Val Leu Gln Ser Ser Gly Leu Tyr Ser Leu
            195                 200                 205
Ser Ser Val Val Thr Val Pro Ser Ser Ser Leu Gly Thr Gln Thr Tyr
        210                 215                 220
Ile Cys Asn Val Asn His Lys Pro Ser Asn Thr Lys Val Asp Lys Lys
225                 230                 235                 240
Val Glu Pro Lys Ser Cys Asp Lys Thr His Thr Cys Pro Pro Cys Pro
                245                 250                 255
Ala Pro Glu Leu Leu Gly Gly Pro Ser Val Phe Leu Phe Pro Pro Lys
            260                 265                 270
Pro Lys Asp Thr Leu Met Ile Ser Arg Thr Pro Glu Val Thr Cys Val
        275                 280                 285
Val Val Asp Val Ser His Glu Asp Pro Glu Val Lys Phe Asn Trp Tyr
    290                 295                 300
Val Asp Gly Val Glu Val His Asn Ala Lys Thr Lys Pro Arg Glu Glu
305                 310                 315                 320
Gln Tyr Asn Ser Thr Tyr Arg Val Val Ser Val Leu Thr Val Leu His
                325                 330                 335
Gln Asp Trp Leu Asn Gly Lys Glu Tyr Lys Cys Lys Val Ser Asn Lys
            340                 345                 350
Ala Leu Pro Ala Pro Ile Glu Lys Thr Ile Ser Lys Ala Lys Gly Gln
            355                 360                 365
Pro Arg Glu Pro Gln Val Tyr Thr Leu Pro Pro Ser Arg Asp Glu Leu
        370                 375                 380
Thr Lys Asn Gln Val Ser Leu Thr Cys Leu Val Lys Gly Phe Tyr Pro
385                 390                 395                 400
Ser Asp Ile Ala Val Glu Trp Glu Ser Asn Gly Gln Pro Glu Asn Asn
                405                 410                 415
Tyr Lys Thr Thr Pro Pro Val Leu Asp Ser Asp Gly Ser Phe Phe Leu
            420                 425                 430
Tyr Ser Lys Leu Thr Val Asp Lys Ser Arg Trp Gln Gln Gly Asn Val
            435                 440                 445
Phe Ser Cys Ser Val Met His Glu Gly Leu His Asn His Tyr Thr Gln
        450                 455                 460
Lys Ser Leu Ser Leu Ser Pro Gly Lys
465                 470

<210> SEQ ID NO 51
<211> LENGTH: 473
<212> TYPE: PRT
<213> ORGANISM: Artificial Sequence
<220> FEATURE:
<223> OTHER INFORMATION: W123P

<400> SEQUENCE: 51
```

```
Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
            35                  40                  45

Ser Gly Tyr Tyr Trp Gly Trp Ile Arg Gln Pro Pro Gly Lys Gly Leu
50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
            100                 105                 110

Phe Cys Ala Arg Val Thr Arg Asp Leu Glu Pro Ile Pro Gly Asp Tyr
    115                 120                 125

Tyr Met Asp Val Trp Gly Lys Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
    275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
```

-continued

```
                420             425             430
Tyr Ser Lys Leu Thr Val Asp Lys Ser Arg Trp Gln Gln Gly Asn Val
            435             440             445

Phe Ser Cys Ser Val Met His Glu Gly Leu His Asn His Tyr Thr Gln
        450             455             460

Lys Ser Leu Ser Leu Ser Pro Gly Lys
465             470

<210> SEQ ID NO 52
<211> LENGTH: 473
<212> TYPE: PRT
<213> ORGANISM: Artificial Sequence
<220> FEATURE:
<223> OTHER INFORMATION: W123L

<400> SEQUENCE: 52

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
            100                 105                 110

Phe Cys Ala Arg Val Thr Arg Asp Leu Glu Leu Ile Pro Gly Asp Tyr
        115                 120                 125

Tyr Met Asp Val Trp Gly Lys Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320
```

```
Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Gly Leu His Asn His Tyr Thr Gln
    450                 455                 460

Lys Ser Leu Ser Leu Ser Pro Gly Lys
465                 470

<210> SEQ ID NO 53
<211> LENGTH: 473
<212> TYPE: PRT
<213> ORGANISM: Artificial Sequence
<220> FEATURE:
<223> OTHER INFORMATION: W123I

<400> SEQUENCE: 53

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
                20                  25                  30

Pro Ser Glu Thr Leu Ser Leu Thr Cys Ala Val Tyr Gly Gly Ser Phe
            35                  40                  45

Ser Gly Tyr Tyr Trp Gly Trp Ile Arg Gln Pro Pro Gly Lys Gly Leu
        50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
            100                 105                 110

Phe Cys Ala Arg Val Thr Arg Asp Leu Glu Ile Ile Pro Gly Asp Tyr
        115                 120                 125

Tyr Met Asp Val Trp Gly Lys Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205
```

```
Ser Ser Val Val Thr Val Pro Ser Ser Leu Gly Thr Gln Thr Tyr
    210                 215                 220
Ile Cys Asn Val Asn His Lys Pro Ser Asn Thr Lys Val Asp Lys Lys
225                 230                 235                 240
Val Glu Pro Lys Ser Cys Asp Lys Thr His Thr Cys Pro Pro Cys Pro
                245                 250                 255
Ala Pro Glu Leu Leu Gly Gly Pro Ser Val Phe Leu Phe Pro Pro Lys
            260                 265                 270
Pro Lys Asp Thr Leu Met Ile Ser Arg Thr Pro Glu Val Thr Cys Val
        275                 280                 285
Val Val Asp Val Ser His Glu Asp Pro Glu Val Lys Phe Asn Trp Tyr
    290                 295                 300
Val Asp Gly Val Glu Val His Asn Ala Lys Thr Lys Pro Arg Glu Glu
305                 310                 315                 320
Gln Tyr Asn Ser Thr Tyr Arg Val Val Ser Val Leu Thr Val Leu His
                325                 330                 335
Gln Asp Trp Leu Asn Gly Lys Glu Tyr Lys Cys Lys Val Ser Asn Lys
            340                 345                 350
Ala Leu Pro Ala Pro Ile Glu Lys Thr Ile Ser Lys Ala Lys Gly Gln
        355                 360                 365
Pro Arg Glu Pro Gln Val Tyr Thr Leu Pro Pro Ser Arg Asp Glu Leu
    370                 375                 380
Thr Lys Asn Gln Val Ser Leu Thr Cys Leu Val Lys Gly Phe Tyr Pro
385                 390                 395                 400
Ser Asp Ile Ala Val Glu Trp Glu Ser Asn Gly Gln Pro Glu Asn Asn
                405                 410                 415
Tyr Lys Thr Thr Pro Pro Val Leu Asp Ser Asp Gly Ser Phe Phe Leu
            420                 425                 430
Tyr Ser Lys Leu Thr Val Asp Lys Ser Arg Trp Gln Gln Gly Asn Val
        435                 440                 445
Phe Ser Cys Ser Val Met His Glu Gly Leu His Asn His Tyr Thr Gln
    450                 455                 460
Lys Ser Leu Ser Leu Ser Pro Gly Lys
465                 470

<210> SEQ ID NO 54
<211> LENGTH: 473
<212> TYPE: PRT
<213> ORGANISM: Artificial Sequence
<220> FEATURE:
<223> OTHER INFORMATION: I124L

<400> SEQUENCE: 54

Met Lys His Leu Trp Phe Phe Leu Leu Leu Val Ala Ala Pro Arg Trp
1               5                   10                  15
Val Leu Ser Gln Val Gln Leu Gln Gln Trp Gly Ala Gly Leu Leu Lys
            20                  25                  30
Pro Ser Glu Thr Leu Ser Leu Thr Cys Ala Val Tyr Gly Gly Ser Phe
        35                  40                  45
Ser Gly Tyr Tyr Trp Gly Trp Ile Arg Gln Pro Pro Gly Lys Gly Leu
    50                  55                  60
Glu Trp Ile Gly Glu Ile Asn His Ser Gly Ser Ala Asn Ser Asn Pro
65                  70                  75                  80
Ser Leu Lys Ser Arg Val Thr Met Ser Val Asp Thr Ser Lys Asn Gln
                85                  90                  95
Phe Ser Leu Lys Val Ser Ser Val Thr Ala Ala Asp Thr Ala Val Tyr
```

```
            100                 105                 110
Phe Cys Ala Arg Val Thr Arg Asp Leu Glu Trp Leu Pro Gly Asp Tyr
            115                 120                 125

Tyr Met Asp Val Trp Gly Lys Gly Thr Thr Val Thr Val Ser Ser Ala
        130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Gly Leu His Asn His Tyr Thr Gln
    450                 455                 460

Lys Ser Leu Ser Leu Ser Pro Gly Lys
465                 470

<210> SEQ ID NO 55
<211> LENGTH: 473
<212> TYPE: PRT
<213> ORGANISM: Artificial Sequence
<220> FEATURE:
<223> OTHER INFORMATION: I124M

<400> SEQUENCE: 55
```

```
Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
            35                  40                  45

Ser Gly Tyr Tyr Trp Gly Trp Ile Arg Gln Pro Pro Gly Lys Gly Leu
50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
            100                 105                 110

Phe Cys Ala Arg Val Thr Arg Asp Leu Glu Trp Met Pro Gly Asp Tyr
            115                 120                 125

Tyr Met Asp Val Trp Gly Lys Gly Thr Thr Val Thr Val Ser Ser Ala
130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
            195                 200                 205

Ser Ser Val Val Thr Val Pro Ser Ser Ser Leu Gly Thr Gln Thr Tyr
210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
            275                 280                 285

Val Val Asp Val Ser His Glu Asp Pro Glu Val Lys Phe Asn Trp Tyr
290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
            355                 360                 365

Pro Arg Glu Pro Gln Val Tyr Thr Leu Pro Pro Ser Arg Asp Glu Leu
370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
```

-continued

```
                          420                 425                 430
Tyr Ser Lys Leu Thr Val Asp Lys Ser Arg Trp Gln Gln Gly Asn Val
                435                 440                 445

Phe Ser Cys Ser Val Met His Glu Gly Leu His Asn His Tyr Thr Gln
    450                 455                 460

Lys Ser Leu Ser Leu Ser Pro Gly Lys
465                 470

<210> SEQ ID NO 56
<211> LENGTH: 473
<212> TYPE: PRT
<213> ORGANISM: Artificial Sequence
<220> FEATURE:
<223> OTHER INFORMATION: I124P

<400> SEQUENCE: 56

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
            100                 105                 110

Phe Cys Ala Arg Val Thr Arg Asp Leu Glu Trp Pro Pro Gly Asp Tyr
        115                 120                 125

Tyr Met Asp Val Trp Gly Lys Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320
```

```
Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Gly Leu His Asn His Tyr Thr Gln
    450                 455                 460

Lys Ser Leu Ser Leu Ser Pro Gly Lys
465                 470

<210> SEQ ID NO 57
<211> LENGTH: 473
<212> TYPE: PRT
<213> ORGANISM: Artificial Sequence
<220> FEATURE:
<223> OTHER INFORMATION: I124V

<400> SEQUENCE: 57

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
            100                 105                 110

Phe Cys Ala Arg Val Thr Arg Asp Leu Glu Trp Val Pro Gly Asp Tyr
        115                 120                 125

Tyr Met Asp Val Trp Gly Lys Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205
```

```
Ser Ser Val Val Thr Val Pro Ser Ser Leu Gly Thr Gln Thr Tyr
    210             215                 220
Ile Cys Asn Val Asn His Lys Pro Ser Asn Thr Lys Val Asp Lys Lys
225                 230                 235                 240
Val Glu Pro Lys Ser Cys Asp Lys Thr His Thr Cys Pro Pro Cys Pro
                245                 250                 255
Ala Pro Glu Leu Leu Gly Gly Pro Ser Val Phe Leu Phe Pro Pro Lys
            260                 265                 270
Pro Lys Asp Thr Leu Met Ile Ser Arg Thr Pro Glu Val Thr Cys Val
        275                 280                 285
Val Val Asp Val Ser His Glu Asp Pro Glu Val Lys Phe Asn Trp Tyr
    290                 295                 300
Val Asp Gly Val Glu Val His Asn Ala Lys Thr Lys Pro Arg Glu Glu
305                 310                 315                 320
Gln Tyr Asn Ser Thr Tyr Arg Val Val Ser Val Leu Thr Val Leu His
                325                 330                 335
Gln Asp Trp Leu Asn Gly Lys Glu Tyr Lys Cys Lys Val Ser Asn Lys
            340                 345                 350
Ala Leu Pro Ala Pro Ile Glu Lys Thr Ile Ser Lys Ala Lys Gly Gln
        355                 360                 365
Pro Arg Glu Pro Gln Val Tyr Thr Leu Pro Pro Ser Arg Asp Glu Leu
    370                 375                 380
Thr Lys Asn Gln Val Ser Leu Thr Cys Leu Val Lys Gly Phe Tyr Pro
385                 390                 395                 400
Ser Asp Ile Ala Val Glu Trp Glu Ser Asn Gly Gln Pro Glu Asn Asn
                405                 410                 415
Tyr Lys Thr Thr Pro Pro Val Leu Asp Ser Asp Gly Ser Phe Phe Leu
            420                 425                 430
Tyr Ser Lys Leu Thr Val Asp Lys Ser Arg Trp Gln Gln Gly Asn Val
        435                 440                 445
Phe Ser Cys Ser Val Met His Glu Gly Leu His Asn His Tyr Thr Gln
    450                 455                 460
Lys Ser Leu Ser Leu Ser Pro Gly Lys
465                 470

<210> SEQ ID NO 58
<211> LENGTH: 473
<212> TYPE: PRT
<213> ORGANISM: Artificial Sequence
<220> FEATURE:
<223> OTHER INFORMATION: I124A

<400> SEQUENCE: 58

Met Lys His Leu Trp Phe Phe Leu Leu Leu Val Ala Ala Pro Arg Trp
1               5                   10                  15
Val Leu Ser Gln Val Gln Leu Gln Gln Trp Gly Ala Gly Leu Leu Lys
            20                  25                  30
Pro Ser Glu Thr Leu Ser Leu Thr Cys Ala Val Tyr Gly Gly Ser Phe
        35                  40                  45
Ser Gly Tyr Tyr Trp Gly Trp Ile Arg Gln Pro Pro Gly Lys Gly Leu
    50                  55                  60
Glu Trp Ile Gly Glu Ile Asn His Ser Gly Ser Ala Asn Ser Asn Pro
65                  70                  75                  80
Ser Leu Lys Ser Arg Val Thr Met Ser Val Asp Thr Ser Lys Asn Gln
                85                  90                  95
Phe Ser Leu Lys Val Ser Ser Val Thr Ala Ala Asp Thr Ala Val Tyr
```

100                 105                 110
Phe Cys Ala Arg Val Thr Arg Asp Leu Glu Trp Ala Pro Gly Asp Tyr
                115                 120                 125

Tyr Met Asp Val Trp Gly Lys Gly Thr Thr Val Thr Val Ser Ser Ala
130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
                180                 185                 190

Val His Thr Phe Pro Ala Val Leu Gln Ser Ser Gly Leu Tyr Ser Leu
                195                 200                 205

Ser Ser Val Val Thr Val Pro Ser Ser Ser Leu Gly Thr Gln Thr Tyr
                210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
                260                 265                 270

Pro Lys Asp Thr Leu Met Ile Ser Arg Thr Pro Glu Val Thr Cys Val
                275                 280                 285

Val Val Asp Val Ser His Glu Asp Pro Glu Val Lys Phe Asn Trp Tyr
                290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
                340                 345                 350

Ala Leu Pro Ala Pro Ile Glu Lys Thr Ile Ser Lys Ala Lys Gly Gln
                355                 360                 365

Pro Arg Glu Pro Gln Val Tyr Thr Leu Pro Pro Ser Arg Asp Glu Leu
                370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
                420                 425                 430

Tyr Ser Lys Leu Thr Val Asp Lys Ser Arg Trp Gln Gln Gly Asn Val
                435                 440                 445

Phe Ser Cys Ser Val Met His Glu Gly Leu His Asn His Tyr Thr Gln
                450                 455                 460

Lys Ser Leu Ser Leu Ser Pro Gly Lys
465                 470

<210> SEQ ID NO 59
<211> LENGTH: 473
<212> TYPE: PRT
<213> ORGANISM: Artificial Sequence
<220> FEATURE:
<223> OTHER INFORMATION: G126P

<400> SEQUENCE: 59

-continued

```
Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
            35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
                100                 105                 110

Phe Cys Ala Arg Val Thr Arg Asp Leu Glu Trp Ile Pro Pro Asp Tyr
        115                 120                 125

Tyr Met Asp Val Trp Gly Lys Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
                180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
                260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
                340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
```

-continued

```
                        420                 425                 430
Tyr Ser Lys Leu Thr Val Asp Lys Ser Arg Trp Gln Gln Gly Asn Val
                435                 440                 445
Phe Ser Cys Ser Val Met His Glu Gly Leu His Asn His Tyr Thr Gln
            450                 455                 460
Lys Ser Leu Ser Leu Ser Pro Gly Lys
465                 470

<210> SEQ ID NO 60
<211> LENGTH: 473
<212> TYPE: PRT
<213> ORGANISM: Artificial Sequence
<220> FEATURE:
<223> OTHER INFORMATION: G126A

<400> SEQUENCE: 60

Met Lys His Leu Trp Phe Phe Leu Leu Leu Val Ala Ala Pro Arg Trp
1               5                   10                  15
Val Leu Ser Gln Val Gln Leu Gln Gln Trp Gly Ala Gly Leu Leu Lys
                20                  25                  30
Pro Ser Glu Thr Leu Ser Leu Thr Cys Ala Val Tyr Gly Gly Ser Phe
            35                  40                  45
Ser Gly Tyr Tyr Trp Gly Trp Ile Arg Gln Pro Pro Gly Lys Gly Leu
        50                  55                  60
Glu Trp Ile Gly Glu Ile Asn His Ser Gly Ser Ala Asn Ser Asn Pro
65                  70                  75                  80
Ser Leu Lys Ser Arg Val Thr Met Ser Val Asp Thr Ser Lys Asn Gln
                85                  90                  95
Phe Ser Leu Lys Val Ser Ser Val Thr Ala Ala Asp Thr Ala Val Tyr
            100                 105                 110
Phe Cys Ala Arg Val Thr Arg Asp Leu Glu Trp Ile Pro Ala Asp Tyr
        115                 120                 125
Tyr Met Asp Val Trp Gly Lys Gly Thr Thr Val Thr Val Ser Ser Ala
    130                 135                 140
Ser Thr Lys Gly Pro Ser Val Phe Pro Leu Ala Pro Ser Ser Lys Ser
145                 150                 155                 160
Thr Ser Gly Gly Thr Ala Ala Leu Gly Cys Leu Val Lys Asp Tyr Phe
                165                 170                 175
Pro Glu Pro Val Thr Val Ser Trp Asn Ser Gly Ala Leu Thr Ser Gly
            180                 185                 190
Val His Thr Phe Pro Ala Val Leu Gln Ser Ser Gly Leu Tyr Ser Leu
        195                 200                 205
Ser Ser Val Val Thr Val Pro Ser Ser Ser Leu Gly Thr Gln Thr Tyr
    210                 215                 220
Ile Cys Asn Val Asn His Lys Pro Ser Asn Thr Lys Val Asp Lys Lys
225                 230                 235                 240
Val Glu Pro Lys Ser Cys Asp Lys Thr His Thr Cys Pro Pro Cys Pro
                245                 250                 255
Ala Pro Glu Leu Leu Gly Gly Pro Ser Val Phe Leu Phe Pro Pro Lys
            260                 265                 270
Pro Lys Asp Thr Leu Met Ile Ser Arg Thr Pro Glu Val Thr Cys Val
        275                 280                 285
Val Val Asp Val Ser His Glu Asp Pro Glu Val Lys Phe Asn Trp Tyr
    290                 295                 300
Val Asp Gly Val Glu Val His Asn Ala Lys Thr Lys Pro Arg Glu Glu
305                 310                 315                 320
```

```
Gln Tyr Asn Ser Thr Tyr Arg Val Val Ser Val Leu Thr Val Leu His
            325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
            355                 360                 365

Pro Arg Glu Pro Gln Val Tyr Thr Leu Pro Pro Ser Arg Asp Glu Leu
            370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
            435                 440                 445

Phe Ser Cys Ser Val Met His Glu Gly Leu His Asn His Tyr Thr Gln
            450                 455                 460

Lys Ser Leu Ser Leu Ser Pro Gly Lys
465                 470

<210> SEQ ID NO 61
<211> LENGTH: 473
<212> TYPE: PRT
<213> ORGANISM: Artificial Sequence
<220> FEATURE:
<223> OTHER INFORMATION: G126S

<400> SEQUENCE: 61

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
            35                  40                  45

Ser Gly Tyr Tyr Trp Gly Trp Ile Arg Gln Pro Pro Gly Lys Gly Leu
        50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
            100                 105                 110

Phe Cys Ala Arg Val Thr Arg Asp Leu Glu Trp Ile Pro Ser Asp Tyr
            115                 120                 125

Tyr Met Asp Val Trp Gly Lys Gly Thr Thr Val Thr Val Ser Ser Ala
            130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
            195                 200                 205
```

Ser Ser Val Val Thr Val Pro Ser Ser Leu Gly Thr Gln Thr Tyr
210                215                220

Ile Cys Asn Val Asn His Lys Pro Ser Asn Thr Lys Val Asp Lys Lys
225                230                235                240

Val Glu Pro Lys Ser Cys Asp Lys Thr His Thr Cys Pro Pro Cys Pro
            245                250                255

Ala Pro Glu Leu Leu Gly Gly Pro Ser Val Phe Leu Phe Pro Pro Lys
            260                265                270

Pro Lys Asp Thr Leu Met Ile Ser Arg Thr Pro Glu Val Thr Cys Val
            275                280                285

Val Val Asp Val Ser His Glu Asp Pro Glu Val Lys Phe Asn Trp Tyr
290                295                300

Val Asp Gly Val Glu Val His Asn Ala Lys Thr Lys Pro Arg Glu Glu
305                310                315                320

Gln Tyr Asn Ser Thr Tyr Arg Val Val Ser Val Leu Thr Val Leu His
            325                330                335

Gln Asp Trp Leu Asn Gly Lys Glu Tyr Lys Cys Lys Val Ser Asn Lys
            340                345                350

Ala Leu Pro Ala Pro Ile Glu Lys Thr Ile Ser Lys Ala Lys Gly Gln
            355                360                365

Pro Arg Glu Pro Gln Val Tyr Thr Leu Pro Pro Ser Arg Asp Glu Leu
370                375                380

Thr Lys Asn Gln Val Ser Leu Thr Cys Leu Val Lys Gly Phe Tyr Pro
385                390                395                400

Ser Asp Ile Ala Val Glu Trp Glu Ser Asn Gly Gln Pro Glu Asn Asn
            405                410                415

Tyr Lys Thr Thr Pro Pro Val Leu Asp Ser Asp Gly Ser Phe Phe Leu
            420                425                430

Tyr Ser Lys Leu Thr Val Asp Lys Ser Arg Trp Gln Gln Gly Asn Val
            435                440                445

Phe Ser Cys Ser Val Met His Glu Gly Leu His Asn His Tyr Thr Gln
            450                455                460

Lys Ser Leu Ser Leu Ser Pro Gly Lys
465                470

<210> SEQ ID NO 62
<211> LENGTH: 473
<212> TYPE: PRT
<213> ORGANISM: Artificial Sequence
<220> FEATURE:
<223> OTHER INFORMATION: G126N

<400> SEQUENCE: 62

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
            35                  40                  45

Ser Gly Tyr Tyr Trp Gly Trp Ile Arg Gln Pro Pro Gly Lys Gly Leu
50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
            85                  90                  95

Phe Ser Leu Lys Val Ser Ser Val Thr Ala Ala Asp Thr Ala Val Tyr

```
                     100                 105                 110
Phe Cys Ala Arg Val Thr Arg Asp Leu Glu Trp Ile Pro Asn Asp Tyr
            115                 120                 125

Tyr Met Asp Val Trp Gly Lys Gly Thr Thr Val Thr Val Ser Ser Ala
        130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Gly Leu His Asn His Tyr Thr Gln
450                 455                 460

Lys Ser Leu Ser Leu Ser Pro Gly Lys
465                 470

<210> SEQ ID NO 63
<211> LENGTH: 473
<212> TYPE: PRT
<213> ORGANISM: Artificial Sequence
<220> FEATURE:
<223> OTHER INFORMATION: G126T

<400> SEQUENCE: 63
```

```
Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
            35                  40                  45

Ser Gly Tyr Tyr Trp Gly Trp Ile Arg Gln Pro Pro Gly Lys Gly Leu
50                      55                  60

Glu Trp Ile Gly Glu Ile Asn His Ser Gly Ser Ala Asn Ser Asn Pro
65                      70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
            100                 105                 110

Phe Cys Ala Arg Val Thr Arg Asp Leu Glu Trp Ile Pro Thr Asp Tyr
            115                 120                 125

Tyr Met Asp Val Trp Gly Lys Gly Thr Thr Val Thr Val Ser Ser Ala
            130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
            195                 200                 205

Ser Ser Val Val Thr Val Pro Ser Ser Ser Leu Gly Thr Gln Thr Tyr
210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
            275                 280                 285

Val Val Asp Val Ser His Glu Asp Pro Glu Val Lys Phe Asn Trp Tyr
            290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
            355                 360                 365

Pro Arg Glu Pro Gln Val Tyr Thr Leu Pro Pro Ser Arg Asp Glu Leu
370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
```

-continued

```
                420                 425                 430
Tyr Ser Lys Leu Thr Val Asp Lys Ser Arg Trp Gln Gln Gly Asn Val
                435                 440                 445
Phe Ser Cys Ser Val Met His Glu Gly Leu His Asn His Tyr Thr Gln
            450                 455                 460
Lys Ser Leu Ser Leu Ser Pro Gly Lys
465                 470

<210> SEQ ID NO 64
<211> LENGTH: 473
<212> TYPE: PRT
<213> ORGANISM: Artificial Sequence
<220> FEATURE:
<223> OTHER INFORMATION: P125G

<400> SEQUENCE: 64

Met Lys His Leu Trp Phe Phe Leu Leu Leu Val Ala Ala Pro Arg Trp
1               5                   10                  15
Val Leu Ser Gln Val Gln Leu Gln Gln Trp Gly Ala Gly Leu Leu Lys
                20                  25                  30
Pro Ser Glu Thr Leu Ser Leu Thr Cys Ala Val Tyr Gly Gly Ser Phe
            35                  40                  45
Ser Gly Tyr Tyr Trp Gly Trp Ile Arg Gln Pro Pro Gly Lys Gly Leu
        50                  55                  60
Glu Trp Ile Gly Glu Ile Asn His Ser Gly Ser Ala Asn Ser Asn Pro
65                  70                  75                  80
Ser Leu Lys Ser Arg Val Thr Met Ser Val Asp Thr Ser Lys Asn Gln
                85                  90                  95
Phe Ser Leu Lys Val Ser Ser Val Thr Ala Ala Asp Thr Ala Val Tyr
            100                 105                 110
Phe Cys Ala Arg Val Thr Arg Asp Leu Glu Trp Ile Gly Gly Asp Tyr
        115                 120                 125
Tyr Met Asp Val Trp Gly Lys Gly Thr Thr Val Thr Val Ser Ser Ala
    130                 135                 140
Ser Thr Lys Gly Pro Ser Val Phe Pro Leu Ala Pro Ser Ser Lys Ser
145                 150                 155                 160
Thr Ser Gly Gly Thr Ala Ala Leu Gly Cys Leu Val Lys Asp Tyr Phe
                165                 170                 175
Pro Glu Pro Val Thr Val Ser Trp Asn Ser Gly Ala Leu Thr Ser Gly
            180                 185                 190
Val His Thr Phe Pro Ala Val Leu Gln Ser Ser Gly Leu Tyr Ser Leu
        195                 200                 205
Ser Ser Val Val Thr Val Pro Ser Ser Ser Leu Gly Thr Gln Thr Tyr
    210                 215                 220
Ile Cys Asn Val Asn His Lys Pro Ser Asn Thr Lys Val Asp Lys Lys
225                 230                 235                 240
Val Glu Pro Lys Ser Cys Asp Lys Thr His Thr Cys Pro Pro Cys Pro
                245                 250                 255
Ala Pro Glu Leu Leu Gly Gly Pro Ser Val Phe Leu Phe Pro Pro Lys
            260                 265                 270
Pro Lys Asp Thr Leu Met Ile Ser Arg Thr Pro Glu Val Thr Cys Val
        275                 280                 285
Val Val Asp Val Ser His Glu Asp Pro Glu Val Lys Phe Asn Trp Tyr
    290                 295                 300
Val Asp Gly Val Glu Val His Asn Ala Lys Thr Lys Pro Arg Glu Glu
305                 310                 315                 320
```

```
Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Gly Leu His Asn His Tyr Thr Gln
    450                 455                 460

Lys Ser Leu Ser Leu Ser Pro Gly Lys
465                 470

<210> SEQ ID NO 65
<211> LENGTH: 473
<212> TYPE: PRT
<213> ORGANISM: Artificial Sequence
<220> FEATURE:
<223> OTHER INFORMATION: P125I

<400> SEQUENCE: 65

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
            100                 105                 110

Phe Cys Ala Arg Val Thr Arg Asp Leu Glu Trp Ile Ile Gly Asp Tyr
        115                 120                 125

Tyr Met Asp Val Trp Gly Lys Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205
```

```
Ser Ser Val Val Thr Val Pro Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Gly Leu His Asn His Tyr Thr Gln
    450                 455                 460

Lys Ser Leu Ser Leu Ser Pro Gly Lys
465                 470

<210> SEQ ID NO 66
<211> LENGTH: 473
<212> TYPE: PRT
<213> ORGANISM: Artificial Sequence
<220> FEATURE:
<223> OTHER INFORMATION: P125A

<400> SEQUENCE: 66

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
```

```
                100             105             110
Phe Cys Ala Arg Val Thr Arg Asp Leu Glu Trp Ile Ala Gly Asp Tyr
            115                 120                 125
Tyr Met Asp Val Trp Gly Lys Gly Thr Thr Val Thr Val Ser Ser Ala
130                 135                 140
Ser Thr Lys Gly Pro Ser Val Phe Pro Leu Ala Pro Ser Ser Lys Ser
145                 150                 155                 160
Thr Ser Gly Gly Thr Ala Ala Leu Gly Cys Leu Val Lys Asp Tyr Phe
                165                 170                 175
Pro Glu Pro Val Thr Val Ser Trp Asn Ser Gly Ala Leu Thr Ser Gly
            180                 185                 190
Val His Thr Phe Pro Ala Val Leu Gln Ser Ser Gly Leu Tyr Ser Leu
        195                 200                 205
Ser Ser Val Val Thr Val Pro Ser Ser Ser Leu Gly Thr Gln Thr Tyr
    210                 215                 220
Ile Cys Asn Val Asn His Lys Pro Ser Asn Thr Lys Val Asp Lys Lys
225                 230                 235                 240
Val Glu Pro Lys Ser Cys Asp Lys Thr His Thr Cys Pro Pro Cys Pro
                245                 250                 255
Ala Pro Glu Leu Leu Gly Gly Pro Ser Val Phe Leu Phe Pro Pro Lys
            260                 265                 270
Pro Lys Asp Thr Leu Met Ile Ser Arg Thr Pro Glu Val Thr Cys Val
        275                 280                 285
Val Val Asp Val Ser His Glu Asp Pro Glu Val Lys Phe Asn Trp Tyr
    290                 295                 300
Val Asp Gly Val Glu Val His Asn Ala Lys Thr Lys Pro Arg Glu Glu
305                 310                 315                 320
Gln Tyr Asn Ser Thr Tyr Arg Val Val Ser Val Leu Thr Val Leu His
                325                 330                 335
Gln Asp Trp Leu Asn Gly Lys Glu Tyr Lys Cys Lys Val Ser Asn Lys
            340                 345                 350
Ala Leu Pro Ala Pro Ile Glu Lys Thr Ile Ser Lys Ala Lys Gly Gln
        355                 360                 365
Pro Arg Glu Pro Gln Val Tyr Thr Leu Pro Pro Ser Arg Asp Glu Leu
    370                 375                 380
Thr Lys Asn Gln Val Ser Leu Thr Cys Leu Val Lys Gly Phe Tyr Pro
385                 390                 395                 400
Ser Asp Ile Ala Val Glu Trp Glu Ser Asn Gly Gln Pro Glu Asn Asn
                405                 410                 415
Tyr Lys Thr Thr Pro Pro Val Leu Asp Ser Asp Gly Ser Phe Phe Leu
            420                 425                 430
Tyr Ser Lys Leu Thr Val Asp Lys Ser Arg Trp Gln Gln Gly Asn Val
        435                 440                 445
Phe Ser Cys Ser Val Met His Glu Gly Leu His Asn His Tyr Thr Gln
    450                 455                 460
Lys Ser Leu Ser Leu Ser Pro Gly Lys
465                 470

<210> SEQ ID NO 67
<211> LENGTH: 473
<212> TYPE: PRT
<213> ORGANISM: Artificial Sequence
<220> FEATURE:
<223> OTHER INFORMATION: P125L

<400> SEQUENCE: 67
```

```
Met Lys His Leu Trp Phe Phe Leu Leu Leu Val Ala Ala Pro Arg Trp
 1               5                  10                  15
Val Leu Ser Gln Val Gln Leu Gln Gln Trp Gly Ala Gly Leu Leu Lys
             20                  25                  30
Pro Ser Glu Thr Leu Ser Leu Thr Cys Ala Val Tyr Gly Gly Ser Phe
             35                  40                  45
Ser Gly Tyr Tyr Trp Gly Trp Ile Arg Gln Pro Pro Gly Lys Gly Leu
 50                  55                  60
Glu Trp Ile Gly Glu Ile Asn His Ser Gly Ser Ala Asn Ser Asn Pro
 65                  70                  75                  80
Ser Leu Lys Ser Arg Val Thr Met Ser Val Asp Thr Ser Lys Asn Gln
             85                  90                  95
Phe Ser Leu Lys Val Ser Ser Val Thr Ala Ala Asp Thr Ala Val Tyr
            100                 105                 110
Phe Cys Ala Arg Val Thr Arg Asp Leu Glu Trp Ile Leu Gly Asp Tyr
            115                 120                 125
Tyr Met Asp Val Trp Gly Lys Gly Thr Thr Val Thr Val Ser Ser Ala
130                 135                 140
Ser Thr Lys Gly Pro Ser Val Phe Pro Leu Ala Pro Ser Ser Lys Ser
145                 150                 155                 160
Thr Ser Gly Gly Thr Ala Ala Leu Gly Cys Leu Val Lys Asp Tyr Phe
            165                 170                 175
Pro Glu Pro Val Thr Val Ser Trp Asn Ser Gly Ala Leu Thr Ser Gly
            180                 185                 190
Val His Thr Phe Pro Ala Val Leu Gln Ser Ser Gly Leu Tyr Ser Leu
            195                 200                 205
Ser Ser Val Val Thr Val Pro Ser Ser Ser Leu Gly Thr Gln Thr Tyr
210                 215                 220
Ile Cys Asn Val Asn His Lys Pro Ser Asn Thr Lys Val Asp Lys Lys
225                 230                 235                 240
Val Glu Pro Lys Ser Cys Asp Lys Thr His Thr Cys Pro Pro Cys Pro
            245                 250                 255
Ala Pro Glu Leu Leu Gly Gly Pro Ser Val Phe Leu Phe Pro Pro Lys
            260                 265                 270
Pro Lys Asp Thr Leu Met Ile Ser Arg Thr Pro Glu Val Thr Cys Val
            275                 280                 285
Val Val Asp Val Ser His Glu Asp Pro Glu Val Lys Phe Asn Trp Tyr
290                 295                 300
Val Asp Gly Val Glu Val His Asn Ala Lys Thr Lys Pro Arg Glu Glu
305                 310                 315                 320
Gln Tyr Asn Ser Thr Tyr Arg Val Val Ser Val Leu Thr Val Leu His
            325                 330                 335
Gln Asp Trp Leu Asn Gly Lys Glu Tyr Lys Cys Lys Val Ser Asn Lys
            340                 345                 350
Ala Leu Pro Ala Pro Ile Glu Lys Thr Ile Ser Lys Ala Lys Gly Gln
            355                 360                 365
Pro Arg Glu Pro Gln Val Tyr Thr Leu Pro Pro Ser Arg Asp Glu Leu
            370                 375                 380
Thr Lys Asn Gln Val Ser Leu Thr Cys Leu Val Lys Gly Phe Tyr Pro
385                 390                 395                 400
Ser Asp Ile Ala Val Glu Trp Glu Ser Asn Gly Gln Pro Glu Asn Asn
            405                 410                 415
Tyr Lys Thr Thr Pro Pro Val Leu Asp Ser Asp Gly Ser Phe Phe Leu
```

-continued

```
                420                 425                 430
Tyr Ser Lys Leu Thr Val Asp Lys Ser Arg Trp Gln Gln Gly Asn Val
            435                 440                 445
Phe Ser Cys Ser Val Met His Glu Gly Leu His Asn His Tyr Thr Gln
450                 455                 460
Lys Ser Leu Ser Leu Ser Pro Gly Lys
465                 470

<210> SEQ ID NO 68
<211> LENGTH: 473
<212> TYPE: PRT
<213> ORGANISM: Artificial Sequence
<220> FEATURE:
<223> OTHER INFORMATION: P125V

<400> SEQUENCE: 68

Met Lys His Leu Trp Phe Phe Leu Leu Leu Val Ala Ala Pro Arg Trp
1               5                   10                  15
Val Leu Ser Gln Val Gln Leu Gln Gln Trp Gly Ala Gly Leu Leu Lys
                20                  25                  30
Pro Ser Glu Thr Leu Ser Leu Thr Cys Ala Val Tyr Gly Gly Ser Phe
            35                  40                  45
Ser Gly Tyr Tyr Trp Gly Trp Ile Arg Gln Pro Pro Gly Lys Gly Leu
    50                  55                  60
Glu Trp Ile Gly Glu Ile Asn His Ser Gly Ser Ala Asn Ser Asn Pro
65                  70                  75                  80
Ser Leu Lys Ser Arg Val Thr Met Ser Val Asp Thr Ser Lys Asn Gln
                85                  90                  95
Phe Ser Leu Lys Val Ser Ser Val Thr Ala Ala Asp Thr Ala Val Tyr
            100                 105                 110
Phe Cys Ala Arg Val Thr Arg Asp Leu Glu Trp Ile Val Gly Asp Tyr
    115                 120                 125
Tyr Met Asp Val Trp Gly Lys Gly Thr Thr Val Thr Val Ser Ser Ala
130                 135                 140
Ser Thr Lys Gly Pro Ser Val Phe Pro Leu Ala Pro Ser Ser Lys Ser
145                 150                 155                 160
Thr Ser Gly Gly Thr Ala Ala Leu Gly Cys Leu Val Lys Asp Tyr Phe
                165                 170                 175
Pro Glu Pro Val Thr Val Ser Trp Asn Ser Gly Ala Leu Thr Ser Gly
            180                 185                 190
Val His Thr Phe Pro Ala Val Leu Gln Ser Ser Gly Leu Tyr Ser Leu
    195                 200                 205
Ser Ser Val Val Thr Val Pro Ser Ser Ser Leu Gly Thr Gln Thr Tyr
210                 215                 220
Ile Cys Asn Val Asn His Lys Pro Ser Asn Thr Lys Val Asp Lys Lys
225                 230                 235                 240
Val Glu Pro Lys Ser Cys Asp Lys Thr His Thr Cys Pro Pro Cys Pro
                245                 250                 255
Ala Pro Glu Leu Leu Gly Gly Pro Ser Val Phe Leu Phe Pro Pro Lys
            260                 265                 270
Pro Lys Asp Thr Leu Met Ile Ser Arg Thr Pro Glu Val Thr Cys Val
    275                 280                 285
Val Val Asp Val Ser His Glu Asp Pro Glu Val Lys Phe Asn Trp Tyr
290                 295                 300
Val Asp Gly Val Glu Val His Asn Ala Lys Thr Lys Pro Arg Glu Glu
305                 310                 315                 320
```

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Gly Leu His Asn His Tyr Thr Gln
    450                 455                 460

Lys Ser Leu Ser Leu Ser Pro Gly Lys
465                 470

<210> SEQ ID NO 69
<211> LENGTH: 473
<212> TYPE: PRT
<213> ORGANISM: Artificial Sequence
<220> FEATURE:
<223> OTHER INFORMATION: P125S

<400> SEQUENCE: 69

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
            100                 105                 110

Phe Cys Ala Arg Val Thr Arg Asp Leu Glu Trp Ile Ser Gly Asp Tyr
        115                 120                 125

Tyr Met Asp Val Trp Gly Lys Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

```
Ser Ser Val Val Thr Val Pro Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Gly Leu His Asn His Tyr Thr Gln
    450                 455                 460

Lys Ser Leu Ser Leu Ser Pro Gly Lys
465                 470

<210> SEQ ID NO 70
<211> LENGTH: 473
<212> TYPE: PRT
<213> ORGANISM: Artificial Sequence
<220> FEATURE:
<223> OTHER INFORMATION: P125T

<400> SEQUENCE: 70

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
```

```
            100                 105                 110
Phe Cys Ala Arg Val Thr Arg Asp Leu Glu Trp Ile Thr Gly Asp Tyr
            115                 120                 125
Tyr Met Asp Val Trp Gly Lys Gly Thr Thr Val Thr Val Ser Ser Ala
130                 135                 140
Ser Thr Lys Gly Pro Ser Val Phe Pro Leu Ala Pro Ser Ser Lys Ser
145                 150                 155                 160
Thr Ser Gly Gly Thr Ala Ala Leu Gly Cys Leu Val Lys Asp Tyr Phe
                165                 170                 175
Pro Glu Pro Val Thr Val Ser Trp Asn Ser Gly Ala Leu Thr Ser Gly
                180                 185                 190
Val His Thr Phe Pro Ala Val Leu Gln Ser Ser Gly Leu Tyr Ser Leu
                195                 200                 205
Ser Ser Val Val Thr Val Pro Ser Ser Ser Leu Gly Thr Gln Thr Tyr
    210                 215                 220
Ile Cys Asn Val Asn His Lys Pro Ser Asn Thr Lys Val Asp Lys Lys
225                 230                 235                 240
Val Glu Pro Lys Ser Cys Asp Lys Thr His Thr Cys Pro Pro Cys Pro
                245                 250                 255
Ala Pro Glu Leu Leu Gly Gly Pro Ser Val Phe Leu Phe Pro Pro Lys
                260                 265                 270
Pro Lys Asp Thr Leu Met Ile Ser Arg Thr Pro Glu Val Thr Cys Val
                275                 280                 285
Val Val Asp Val Ser His Glu Asp Pro Glu Val Lys Phe Asn Trp Tyr
                290                 295                 300
Val Asp Gly Val Glu Val His Asn Ala Lys Thr Lys Pro Arg Glu Glu
305                 310                 315                 320
Gln Tyr Asn Ser Thr Tyr Arg Val Val Ser Val Leu Thr Val Leu His
                325                 330                 335
Gln Asp Trp Leu Asn Gly Lys Glu Tyr Lys Cys Lys Val Ser Asn Lys
                340                 345                 350
Ala Leu Pro Ala Pro Ile Glu Lys Thr Ile Ser Lys Ala Lys Gly Gln
                355                 360                 365
Pro Arg Glu Pro Gln Val Tyr Thr Leu Pro Pro Ser Arg Asp Glu Leu
                370                 375                 380
Thr Lys Asn Gln Val Ser Leu Thr Cys Leu Val Lys Gly Phe Tyr Pro
385                 390                 395                 400
Ser Asp Ile Ala Val Glu Trp Glu Ser Asn Gly Gln Pro Glu Asn Asn
                405                 410                 415
Tyr Lys Thr Thr Pro Pro Val Leu Asp Ser Asp Gly Ser Phe Phe Leu
                420                 425                 430
Tyr Ser Lys Leu Thr Val Asp Lys Ser Arg Trp Gln Gln Gly Asn Val
                435                 440                 445
Phe Ser Cys Ser Val Met His Glu Gly Leu His Asn His Tyr Thr Gln
                450                 455                 460
Lys Ser Leu Ser Leu Ser Pro Gly Lys
465                 470

<210> SEQ ID NO 71
<211> LENGTH: 473
<212> TYPE: PRT
<213> ORGANISM: Artificial Sequence
<220> FEATURE:
<223> OTHER INFORMATION: P125N

<400> SEQUENCE: 71
```

```
Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
                35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
                100                 105                 110

Phe Cys Ala Arg Val Thr Arg Asp Leu Glu Trp Ile Asn Gly Asp Tyr
    115                 120                 125

Tyr Met Asp Val Trp Gly Lys Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
                180                 185                 190

Val His Thr Phe Pro Ala Val Leu Gln Ser Ser Gly Leu Tyr Ser Leu
    195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
                260                 265                 270

Pro Lys Asp Thr Leu Met Ile Ser Arg Thr Pro Glu Val Thr Cys Val
    275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
                340                 345                 350

Ala Leu Pro Ala Pro Ile Glu Lys Thr Ile Ser Lys Ala Lys Gly Gln
    355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
```

-continued

```
                420                 425                 430
Tyr Ser Lys Leu Thr Val Asp Lys Ser Arg Trp Gln Gln Gly Asn Val
                435                 440                 445
Phe Ser Cys Ser Val Met His Glu Gly Leu His Asn His Tyr Thr Gln
                450                 455                 460
Lys Ser Leu Ser Leu Ser Pro Gly Lys
465                 470

<210> SEQ ID NO 72
<211> LENGTH: 473
<212> TYPE: PRT
<213> ORGANISM: Artificial Sequence
<220> FEATURE:
<223> OTHER INFORMATION: P125Q

<400> SEQUENCE: 72

Met Lys His Leu Trp Phe Phe Leu Leu Leu Val Ala Ala Pro Arg Trp
1               5                   10                  15
Val Leu Ser Gln Val Gln Leu Gln Gln Trp Gly Ala Gly Leu Leu Lys
                20                  25                  30
Pro Ser Glu Thr Leu Ser Leu Thr Cys Ala Val Tyr Gly Gly Ser Phe
                35                  40                  45
Ser Gly Tyr Tyr Trp Gly Trp Ile Arg Gln Pro Pro Gly Lys Gly Leu
        50                  55                  60
Glu Trp Ile Gly Glu Ile Asn His Ser Gly Ser Ala Asn Ser Asn Pro
65              70                  75                  80
Ser Leu Lys Ser Arg Val Thr Met Ser Val Asp Thr Ser Lys Asn Gln
                85                  90                  95
Phe Ser Leu Lys Val Ser Ser Val Thr Ala Ala Asp Thr Ala Val Tyr
                100                 105                 110
Phe Cys Ala Arg Val Thr Arg Asp Leu Glu Trp Ile Gln Gly Asp Tyr
                115                 120                 125
Tyr Met Asp Val Trp Gly Lys Gly Thr Thr Val Thr Val Ser Ser Ala
        130                 135                 140
Ser Thr Lys Gly Pro Ser Val Phe Pro Leu Ala Pro Ser Ser Lys Ser
145                 150                 155                 160
Thr Ser Gly Gly Thr Ala Ala Leu Gly Cys Leu Val Lys Asp Tyr Phe
                165                 170                 175
Pro Glu Pro Val Thr Val Ser Trp Asn Ser Gly Ala Leu Thr Ser Gly
                180                 185                 190
Val His Thr Phe Pro Ala Val Leu Gln Ser Ser Gly Leu Tyr Ser Leu
                195                 200                 205
Ser Ser Val Val Thr Val Pro Ser Ser Ser Leu Gly Thr Gln Thr Tyr
        210                 215                 220
Ile Cys Asn Val Asn His Lys Pro Ser Asn Thr Lys Val Asp Lys Lys
225                 230                 235                 240
Val Glu Pro Lys Ser Cys Asp Lys Thr His Thr Cys Pro Pro Cys Pro
                245                 250                 255
Ala Pro Glu Leu Leu Gly Gly Pro Ser Val Phe Leu Phe Pro Pro Lys
                260                 265                 270
Pro Lys Asp Thr Leu Met Ile Ser Arg Thr Pro Glu Val Thr Cys Val
                275                 280                 285
Val Val Asp Val Ser His Glu Asp Pro Glu Val Lys Phe Asn Trp Tyr
        290                 295                 300
Val Asp Gly Val Glu Val His Asn Ala Lys Thr Lys Pro Arg Glu Glu
305                 310                 315                 320
```

```
Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Gly Leu His Asn His Tyr Thr Gln
    450                 455                 460

Lys Ser Leu Ser Leu Ser Pro Gly Lys
465                 470

<210> SEQ ID NO 73
<211> LENGTH: 473
<212> TYPE: PRT
<213> ORGANISM: Artificial Sequence
<220> FEATURE:
<223> OTHER INFORMATION: P125D

<400> SEQUENCE: 73

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
            100                 105                 110

Phe Cys Ala Arg Val Thr Arg Asp Leu Glu Trp Ile Asp Gly Asp Tyr
        115                 120                 125

Tyr Met Asp Val Trp Gly Lys Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205
```

Ser Ser Val Thr Val Pro Ser Ser Leu Gly Thr Gln Thr Tyr
    210             215             220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Gly Leu His Asn His Tyr Thr Gln
450                 455                 460

Lys Ser Leu Ser Leu Ser Pro Gly Lys
465                 470

<210> SEQ ID NO 74
<211> LENGTH: 473
<212> TYPE: PRT
<213> ORGANISM: Artificial Sequence
<220> FEATURE:
<223> OTHER INFORMATION: P125E

<400> SEQUENCE: 74

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr 100                 105                 110
        Phe Cys Ala Arg Val Thr Arg Asp Leu Glu Trp Ile Glu Gly Asp Tyr
                        115                 120                 125

Tyr Met Asp Val Trp Gly Lys Gly Thr Thr Val Thr Val Ser Ser Ala
                    130                 135                 140

Ser Thr Lys Gly Pro Ser Val Phe Pro Leu Ala Pro Ser Ser Lys Ser
        145                 150                 155                 160

Thr Ser Gly Gly Thr Ala Ala Leu Gly Cys Leu Val Lys Asp Tyr Phe
                        165                 170                 175

Pro Glu Pro Val Thr Val Ser Trp Asn Ser Gly Ala Leu Thr Ser Gly
                    180                 185                 190

Val His Thr Phe Pro Ala Val Leu Gln Ser Ser Gly Leu Tyr Ser Leu
                        195                 200                 205

Ser Ser Val Val Thr Val Pro Ser Ser Ser Leu Gly Thr Gln Thr Tyr
            210                 215                 220

Ile Cys Asn Val Asn His Lys Pro Ser Asn Thr Lys Val Asp Lys Lys
        225                 230                 235                 240

Val Glu Pro Lys Ser Cys Asp Lys Thr His Thr Cys Pro Pro Cys Pro
                        245                 250                 255

Ala Pro Glu Leu Leu Gly Gly Pro Ser Val Phe Leu Phe Pro Pro Lys
                    260                 265                 270

Pro Lys Asp Thr Leu Met Ile Ser Arg Thr Pro Glu Val Thr Cys Val
                        275                 280                 285

Val Val Asp Val Ser His Glu Asp Pro Glu Val Lys Phe Asn Trp Tyr
                    290                 295                 300

Val Asp Gly Val Glu Val His Asn Ala Lys Thr Lys Pro Arg Glu Glu
        305                 310                 315                 320

Gln Tyr Asn Ser Thr Tyr Arg Val Val Ser Val Leu Thr Val Leu His
                        325                 330                 335

Gln Asp Trp Leu Asn Gly Lys Glu Tyr Lys Cys Lys Val Ser Asn Lys
                    340                 345                 350

Ala Leu Pro Ala Pro Ile Glu Lys Thr Ile Ser Lys Ala Lys Gly Gln
                        355                 360                 365

Pro Arg Glu Pro Gln Val Tyr Thr Leu Pro Pro Ser Arg Asp Glu Leu
        370                 375                 380

Thr Lys Asn Gln Val Ser Leu Thr Cys Leu Val Lys Gly Phe Tyr Pro
        385                 390                 395                 400

Ser Asp Ile Ala Val Glu Trp Glu Ser Asn Gly Gln Pro Glu Asn Asn
                        405                 410                 415

Tyr Lys Thr Thr Pro Pro Val Leu Asp Ser Asp Gly Ser Phe Phe Leu
                    420                 425                 430

Tyr Ser Lys Leu Thr Val Asp Lys Ser Arg Trp Gln Gln Gly Asn Val
                        435                 440                 445

Phe Ser Cys Ser Val Met His Glu Gly Leu His Asn His Tyr Thr Gln
                    450                 455                 460

Lys Ser Leu Ser Leu Ser Pro Gly Lys
        465                 470

<210> SEQ ID NO 75
<211> LENGTH: 473
<212> TYPE: PRT
<213> ORGANISM: Artificial Sequence
<220> FEATURE:
<223> OTHER INFORMATION: P125K

<400> SEQUENCE: 75

```
Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
                35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
                100                 105                 110

Phe Cys Ala Arg Val Thr Arg Asp Leu Glu Trp Ile Lys Gly Asp Tyr
            115                 120                 125

Tyr Met Asp Val Trp Gly Lys Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
    195                 200                 205

Ser Ser Val Val Thr Val Pro Ser Ser Ser Leu Gly Thr Gln Thr Tyr
210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
    275                 280                 285

Val Val Asp Val Ser His Glu Asp Pro Glu Val Lys Phe Asn Trp Tyr
290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
    355                 360                 365

Pro Arg Glu Pro Gln Val Tyr Thr Leu Pro Pro Ser Arg Asp Glu Leu
370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
```

-continued

```
                420             425             430
Tyr Ser Lys Leu Thr Val Asp Lys Ser Arg Trp Gln Gln Gly Asn Val
            435             440             445

Phe Ser Cys Ser Val Met His Glu Gly Leu His Asn His Tyr Thr Gln
450             455             460

Lys Ser Leu Ser Leu Ser Pro Gly Lys
465             470

<210> SEQ ID NO 76
<211> LENGTH: 473
<212> TYPE: PRT
<213> ORGANISM: Artificial Sequence
<220> FEATURE:
<223> OTHER INFORMATION: P125H

<400> SEQUENCE: 76

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
                20                  25                  30

Pro Ser Glu Thr Leu Ser Leu Thr Cys Ala Val Tyr Gly Gly Ser Phe
            35                  40                  45

Ser Gly Tyr Tyr Trp Gly Trp Ile Arg Gln Pro Pro Gly Lys Gly Leu
        50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
            100                 105                 110

Phe Cys Ala Arg Val Thr Arg Asp Leu Glu Trp Ile His Gly Asp Tyr
        115                 120                 125

Tyr Met Asp Val Trp Gly Lys Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320
```

```
Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Gly Leu His Asn His Tyr Thr Gln
    450                 455                 460

Lys Ser Leu Ser Leu Ser Pro Gly Lys
465                 470

<210> SEQ ID NO 77
<211> LENGTH: 473
<212> TYPE: PRT
<213> ORGANISM: Artificial Sequence
<220> FEATURE:
<223> OTHER INFORMATION: P125C

<400> SEQUENCE: 77

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
            100                 105                 110

Phe Cys Ala Arg Val Thr Arg Asp Leu Glu Trp Ile Cys Gly Asp Tyr
        115                 120                 125

Tyr Met Asp Val Trp Gly Lys Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205
```

```
Ser Ser Val Val Thr Val Pro Ser Ser Leu Gly Thr Gln Thr Tyr
    210             215                 220
Ile Cys Asn Val Asn His Lys Pro Ser Asn Thr Lys Val Asp Lys Lys
225                 230                 235                 240
Val Glu Pro Lys Ser Cys Asp Lys Thr His Thr Cys Pro Pro Cys Pro
                245                 250                 255
Ala Pro Glu Leu Leu Gly Gly Pro Ser Val Phe Leu Phe Pro Pro Lys
            260                 265                 270
Pro Lys Asp Thr Leu Met Ile Ser Arg Thr Pro Glu Val Thr Cys Val
        275                 280                 285
Val Val Asp Val Ser His Glu Asp Pro Glu Val Lys Phe Asn Trp Tyr
    290                 295                 300
Val Asp Gly Val Glu Val His Asn Ala Lys Thr Lys Pro Arg Glu Glu
305                 310                 315                 320
Gln Tyr Asn Ser Thr Tyr Arg Val Val Ser Val Leu Thr Val Leu His
                325                 330                 335
Gln Asp Trp Leu Asn Gly Lys Glu Tyr Lys Cys Lys Val Ser Asn Lys
            340                 345                 350
Ala Leu Pro Ala Pro Ile Glu Lys Thr Ile Ser Lys Ala Lys Gly Gln
        355                 360                 365
Pro Arg Glu Pro Gln Val Tyr Thr Leu Pro Pro Ser Arg Asp Glu Leu
    370                 375                 380
Thr Lys Asn Gln Val Ser Leu Thr Cys Leu Val Lys Gly Phe Tyr Pro
385                 390                 395                 400
Ser Asp Ile Ala Val Glu Trp Glu Ser Asn Gly Gln Pro Glu Asn Asn
                405                 410                 415
Tyr Lys Thr Thr Pro Pro Val Leu Asp Ser Asp Gly Ser Phe Phe Leu
            420                 425                 430
Tyr Ser Lys Leu Thr Val Asp Lys Ser Arg Trp Gln Gln Gly Asn Val
        435                 440                 445
Phe Ser Cys Ser Val Met His Glu Gly Leu His Asn His Tyr Thr Gln
    450                 455                 460
Lys Ser Leu Ser Leu Ser Pro Gly Lys
465                 470

<210> SEQ ID NO 78
<211> LENGTH: 473
<212> TYPE: PRT
<213> ORGANISM: Artificial Sequence
<220> FEATURE:
<223> OTHER INFORMATION: P125M

<400> SEQUENCE: 78

Met Lys His Leu Trp Phe Phe Leu Leu Leu Val Ala Ala Pro Arg Trp
1               5                   10                  15
Val Leu Ser Gln Val Gln Leu Gln Gln Trp Gly Ala Gly Leu Leu Lys
            20                  25                  30
Pro Ser Glu Thr Leu Ser Leu Thr Cys Ala Val Tyr Gly Gly Ser Phe
        35                  40                  45
Ser Gly Tyr Tyr Trp Gly Trp Ile Arg Gln Pro Pro Gly Lys Gly Leu
    50                  55                  60
Glu Trp Ile Gly Glu Ile Asn His Ser Gly Ser Ala Asn Ser Asn Pro
65                  70                  75                  80
Ser Leu Lys Ser Arg Val Thr Met Ser Val Asp Thr Ser Lys Asn Gln
                85                  90                  95
Phe Ser Leu Lys Val Ser Ser Val Thr Ala Ala Asp Thr Ala Val Tyr
```

```
                     100                 105                 110
Phe Cys Ala Arg Val Thr Arg Asp Leu Glu Trp Ile Met Gly Asp Tyr
                115                 120                 125
Tyr Met Asp Val Trp Gly Lys Gly Thr Thr Val Thr Val Ser Ser Ala
130                 135                 140
Ser Thr Lys Gly Pro Ser Val Phe Pro Leu Ala Pro Ser Ser Lys Ser
145                 150                 155                 160
Thr Ser Gly Gly Thr Ala Ala Leu Gly Cys Leu Val Lys Asp Tyr Phe
                165                 170                 175
Pro Glu Pro Val Thr Val Ser Trp Asn Ser Gly Ala Leu Thr Ser Gly
                180                 185                 190
Val His Thr Phe Pro Ala Val Leu Gln Ser Ser Gly Leu Tyr Ser Leu
                195                 200                 205
Ser Ser Val Val Thr Val Pro Ser Ser Ser Leu Gly Thr Gln Thr Tyr
                210                 215                 220
Ile Cys Asn Val Asn His Lys Pro Ser Asn Thr Lys Val Asp Lys Lys
225                 230                 235                 240
Val Glu Pro Lys Ser Cys Asp Lys Thr His Thr Cys Pro Pro Cys Pro
                245                 250                 255
Ala Pro Glu Leu Leu Gly Gly Pro Ser Val Phe Leu Phe Pro Pro Lys
                260                 265                 270
Pro Lys Asp Thr Leu Met Ile Ser Arg Thr Pro Glu Val Thr Cys Val
                275                 280                 285
Val Val Asp Val Ser His Glu Asp Pro Glu Val Lys Phe Asn Trp Tyr
                290                 295                 300
Val Asp Gly Val Glu Val His Asn Ala Lys Thr Lys Pro Arg Glu Glu
305                 310                 315                 320
Gln Tyr Asn Ser Thr Tyr Arg Val Val Ser Val Leu Thr Val Leu His
                325                 330                 335
Gln Asp Trp Leu Asn Gly Lys Glu Tyr Lys Cys Lys Val Ser Asn Lys
                340                 345                 350
Ala Leu Pro Ala Pro Ile Glu Lys Thr Ile Ser Lys Ala Lys Gly Gln
                355                 360                 365
Pro Arg Glu Pro Gln Val Tyr Thr Leu Pro Pro Ser Arg Asp Glu Leu
                370                 375                 380
Thr Lys Asn Gln Val Ser Leu Thr Cys Leu Val Lys Gly Phe Tyr Pro
385                 390                 395                 400
Ser Asp Ile Ala Val Glu Trp Glu Ser Asn Gly Gln Pro Glu Asn Asn
                405                 410                 415
Tyr Lys Thr Thr Pro Pro Val Leu Asp Ser Asp Gly Ser Phe Phe Leu
                420                 425                 430
Tyr Ser Lys Leu Thr Val Asp Lys Ser Arg Trp Gln Gln Gly Asn Val
                435                 440                 445
Phe Ser Cys Ser Val Met His Glu Gly Leu His Asn His Tyr Thr Gln
                450                 455                 460
Lys Ser Leu Ser Leu Ser Pro Gly Lys
465                 470

<210> SEQ ID NO 79
<211> LENGTH: 473
<212> TYPE: PRT
<213> ORGANISM: Artificial Sequence
<220> FEATURE:
<223> OTHER INFORMATION: P125Y

<400> SEQUENCE: 79
```

```
Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
            35                  40                  45

Ser Gly Tyr Tyr Trp Gly Trp Ile Arg Gln Pro Pro Gly Lys Gly Leu
        50                  55                  60

Glu Trp Ile Gly Glu Ile Asn His Ser Gly Ser Ala Asn Ser Asn Pro
65                      70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
                100                 105                 110

Phe Cys Ala Arg Val Thr Arg Asp Leu Glu Trp Ile Tyr Gly Asp Tyr
        115                 120                 125

Tyr Met Asp Val Trp Gly Lys Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
```

```
                        420             425             430
Tyr Ser Lys Leu Thr Val Asp Lys Ser Arg Trp Gln Gln Gly Asn Val
                435                 440                 445
Phe Ser Cys Ser Val Met His Glu Gly Leu His Asn His Tyr Thr Gln
        450                 455                 460
Lys Ser Leu Ser Leu Ser Pro Gly Lys
465                 470

<210> SEQ ID NO 80
<211> LENGTH: 473
<212> TYPE: PRT
<213> ORGANISM: Artificial Sequence
<220> FEATURE:
<223> OTHER INFORMATION: P125W

<400> SEQUENCE: 80

Met Lys His Leu Trp Phe Phe Leu Leu Leu Val Ala Ala Pro Arg Trp
1               5                   10                  15
Val Leu Ser Gln Val Gln Leu Gln Gln Trp Gly Ala Gly Leu Leu Lys
                20                  25                  30
Pro Ser Glu Thr Leu Ser Leu Thr Cys Ala Val Tyr Gly Gly Ser Phe
            35                  40                  45
Ser Gly Tyr Tyr Trp Gly Trp Ile Arg Gln Pro Pro Gly Lys Gly Leu
        50                  55                  60
Glu Trp Ile Gly Glu Ile Asn His Ser Gly Ser Ala Asn Ser Asn Pro
65              70                  75                  80
Ser Leu Lys Ser Arg Val Thr Met Ser Val Asp Thr Ser Lys Asn Gln
                85                  90                  95
Phe Ser Leu Lys Val Ser Ser Val Thr Ala Ala Asp Thr Ala Val Tyr
            100                 105                 110
Phe Cys Ala Arg Val Thr Arg Asp Leu Glu Trp Ile Trp Gly Asp Tyr
        115                 120                 125
Tyr Met Asp Val Trp Gly Lys Gly Thr Thr Val Thr Val Ser Ser Ala
    130                 135                 140
Ser Thr Lys Gly Pro Ser Val Phe Pro Leu Ala Pro Ser Ser Lys Ser
145                 150                 155                 160
Thr Ser Gly Gly Thr Ala Ala Leu Gly Cys Leu Val Lys Asp Tyr Phe
                165                 170                 175
Pro Glu Pro Val Thr Val Ser Trp Asn Ser Gly Ala Leu Thr Ser Gly
            180                 185                 190
Val His Thr Phe Pro Ala Val Leu Gln Ser Ser Gly Leu Tyr Ser Leu
        195                 200                 205
Ser Ser Val Val Thr Val Pro Ser Ser Ser Leu Gly Thr Gln Thr Tyr
    210                 215                 220
Ile Cys Asn Val Asn His Lys Pro Ser Asn Thr Lys Val Asp Lys Lys
225                 230                 235                 240
Val Glu Pro Lys Ser Cys Asp Lys Thr His Thr Cys Pro Pro Cys Pro
                245                 250                 255
Ala Pro Glu Leu Leu Gly Gly Pro Ser Val Phe Leu Phe Pro Pro Lys
            260                 265                 270
Pro Lys Asp Thr Leu Met Ile Ser Arg Thr Pro Glu Val Thr Cys Val
        275                 280                 285
Val Val Asp Val Ser His Glu Asp Pro Glu Val Lys Phe Asn Trp Tyr
    290                 295                 300
Val Asp Gly Val Glu Val His Asn Ala Lys Thr Lys Pro Arg Glu Glu
305                 310                 315                 320
```

```
Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Gly Leu His Asn His Tyr Thr Gln
    450                 455                 460

Lys Ser Leu Ser Leu Ser Pro Gly Lys
465                 470

<210> SEQ ID NO 81
<211> LENGTH: 473
<212> TYPE: PRT
<213> ORGANISM: Artificial Sequence
<220> FEATURE:
<223> OTHER INFORMATION: P125F

<400> SEQUENCE: 81

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
            100                 105                 110

Phe Cys Ala Arg Val Thr Arg Asp Leu Glu Trp Ile Phe Gly Asp Tyr
        115                 120                 125

Tyr Met Asp Val Trp Gly Lys Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205
```

```
Ser Ser Val Val Thr Val Pro Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Gly Leu His Asn His Tyr Thr Gln
450                 455                 460

Lys Ser Leu Ser Leu Ser Pro Gly Lys
465                 470

<210> SEQ ID NO 82
<211> LENGTH: 473
<212> TYPE: PRT
<213> ORGANISM: Artificial Sequence
<220> FEATURE:
<223> OTHER INFORMATION: V117L

<400> SEQUENCE: 82

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
```

100                 105                 110
Phe Cys Ala Arg Leu Thr Arg Asp Leu Glu Trp Ile Pro Gly Asp Tyr
            115                 120                 125

Tyr Met Asp Val Trp Gly Lys Gly Thr Thr Val Thr Val Ser Ser Ala
        130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Gly Leu His Asn His Tyr Thr Gln
    450                 455                 460

Lys Ser Leu Ser Leu Ser Pro Gly Lys
465                 470

<210> SEQ ID NO 83
<211> LENGTH: 473
<212> TYPE: PRT
<213> ORGANISM: Artificial Sequence
<220> FEATURE:
<223> OTHER INFORMATION: V117I

<400> SEQUENCE: 83

```
Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
            35                  40                  45

Ser Gly Tyr Tyr Trp Gly Trp Ile Arg Gln Pro Pro Gly Lys Gly Leu
50                      55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
            100                 105                 110

Phe Cys Ala Arg Ile Thr Arg Asp Leu Glu Trp Ile Pro Gly Asp Tyr
        115                 120                 125

Tyr Met Asp Val Trp Gly Lys Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
```

```
                    420             425             430
Tyr Ser Lys Leu Thr Val Asp Lys Ser Arg Trp Gln Gln Gly Asn Val
            435             440             445

Phe Ser Cys Ser Val Met His Glu Gly Leu His Asn His Tyr Thr Gln
    450             455             460

Lys Ser Leu Ser Leu Ser Pro Gly Lys
465             470

<210> SEQ ID NO 84
<211> LENGTH: 473
<212> TYPE: PRT
<213> ORGANISM: Artificial Sequence
<220> FEATURE:
<223> OTHER INFORMATION: T118S

<400> SEQUENCE: 84

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
                20                  25                  30

Pro Ser Glu Thr Leu Ser Leu Thr Cys Ala Val Tyr Gly Gly Ser Phe
            35                  40                  45

Ser Gly Tyr Tyr Trp Gly Trp Ile Arg Gln Pro Pro Gly Lys Gly Leu
        50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
            100                 105                 110

Phe Cys Ala Arg Val Ser Arg Asp Leu Glu Trp Ile Pro Gly Asp Tyr
        115                 120                 125

Tyr Met Asp Val Trp Gly Lys Gly Thr Thr Val Thr Val Ser Ser Ala
130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
290                 295                 300

Val Asp Gly Val Glu Val His Asn Ala Lys Thr Lys Pro Arg Glu Glu
305                 310                 315                 320
```

Gln Tyr Asn Ser Thr Tyr Arg Val Val Ser Val Leu Thr Val Leu His
            325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
            355                 360                 365

Pro Arg Glu Pro Gln Val Tyr Thr Leu Pro Pro Ser Arg Asp Glu Leu
        370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
            405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
            435                 440                 445

Phe Ser Cys Ser Val Met His Glu Gly Leu His Asn His Tyr Thr Gln
            450                 455                 460

Lys Ser Leu Ser Leu Ser Pro Gly Lys
465                 470

<210> SEQ ID NO 85
<211> LENGTH: 473
<212> TYPE: PRT
<213> ORGANISM: Artificial Sequence
<220> FEATURE:
<223> OTHER INFORMATION: T118K

<400> SEQUENCE: 85

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
            100                 105                 110

Phe Cys Ala Arg Val Lys Arg Asp Leu Glu Trp Ile Pro Gly Asp Tyr
            115                 120                 125

Tyr Met Asp Val Trp Gly Lys Gly Thr Thr Val Thr Val Ser Ser Ala
        130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

```
Ser Ser Val Val Thr Val Pro Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Gly Leu His Asn His Tyr Thr Gln
    450                 455                 460

Lys Ser Leu Ser Leu Ser Pro Gly Lys
465                 470

<210> SEQ ID NO 86
<211> LENGTH: 473
<212> TYPE: PRT
<213> ORGANISM: Artificial Sequence
<220> FEATURE:
<223> OTHER INFORMATION: R119K

<400> SEQUENCE: 86

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
```

```
                100                 105                 110
Phe Cys Ala Arg Val Thr Lys Asp Leu Glu Trp Ile Pro Gly Asp Tyr
            115                 120                 125

Tyr Met Asp Val Trp Gly Lys Gly Thr Thr Val Thr Val Ser Ser Ala
130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
            195                 200                 205

Ser Ser Val Val Thr Val Pro Ser Ser Ser Leu Gly Thr Gln Thr Tyr
            210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
            245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
            275                 280                 285

Val Val Asp Val Ser His Glu Asp Pro Glu Val Lys Phe Asn Trp Tyr
            290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
            355                 360                 365

Pro Arg Glu Pro Gln Val Tyr Thr Leu Pro Pro Ser Arg Asp Glu Leu
            370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
            435                 440                 445

Phe Ser Cys Ser Val Met His Glu Gly Leu His Asn His Tyr Thr Gln
            450                 455                 460

Lys Ser Leu Ser Leu Ser Pro Gly Lys
465                 470

<210> SEQ ID NO 87
<211> LENGTH: 473
<212> TYPE: PRT
<213> ORGANISM: Artificial Sequence
<220> FEATURE:
<223> OTHER INFORMATION: R119T

<400> SEQUENCE: 87
```

-continued

```
Met Lys His Leu Trp Phe Phe Leu Leu Leu Val Ala Ala Pro Arg Trp
 1               5                  10                  15

Val Leu Ser Gln Val Gln Leu Gln Gln Trp Gly Ala Gly Leu Leu Lys
             20                  25                  30

Pro Ser Glu Thr Leu Ser Leu Thr Cys Ala Val Tyr Gly Gly Ser Phe
             35                  40                  45

Ser Gly Tyr Tyr Trp Gly Trp Ile Arg Gln Pro Pro Gly Lys Gly Leu
 50                  55                  60

Glu Trp Ile Gly Glu Ile Asn His Ser Gly Ser Ala Asn Ser Asn Pro
 65                  70                  75                  80

Ser Leu Lys Ser Arg Val Thr Met Ser Val Asp Thr Ser Lys Asn Gln
             85                  90                  95

Phe Ser Leu Lys Val Ser Ser Val Thr Ala Ala Asp Thr Ala Val Tyr
            100                 105                 110

Phe Cys Ala Arg Val Thr Thr Asp Leu Glu Trp Ile Pro Gly Asp Tyr
            115                 120                 125

Tyr Met Asp Val Trp Gly Lys Gly Thr Thr Val Thr Val Ser Ser Ala
            130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
            195                 200                 205

Ser Ser Val Val Thr Val Pro Ser Ser Ser Leu Gly Thr Gln Thr Tyr
            210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
            275                 280                 285

Val Val Asp Val Ser His Glu Asp Pro Glu Val Lys Phe Asn Trp Tyr
            290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
            355                 360                 365

Pro Arg Glu Pro Gln Val Tyr Thr Leu Pro Pro Ser Arg Asp Glu Leu
            370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
            405                 410                 415

Tyr Lys Thr Thr Pro Pro Val Leu Asp Ser Asp Gly Ser Phe Phe Leu
```

```
                      420                 425                 430
Tyr Ser Lys Leu Thr Val Asp Lys Ser Arg Trp Gln Gln Gly Asn Val
                435                 440                 445

Phe Ser Cys Ser Val Met His Glu Gly Leu His Asn His Tyr Thr Gln
        450                 455                 460

Lys Ser Leu Ser Leu Ser Pro Gly Lys
465                 470

<210> SEQ ID NO 88
<211> LENGTH: 473
<212> TYPE: PRT
<213> ORGANISM: Artificial Sequence
<220> FEATURE:
<223> OTHER INFORMATION: D120E

<400> SEQUENCE: 88

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
            100                 105                 110

Phe Cys Ala Arg Val Thr Arg Glu Leu Glu Trp Ile Pro Gly Asp Tyr
        115                 120                 125

Tyr Met Asp Val Trp Gly Lys Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320
```

Gln Tyr Asn Ser Thr Tyr Arg Val Val Ser Val Leu Thr Val Leu His
            325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
            355                 360                 365

Pro Arg Glu Pro Gln Val Tyr Thr Leu Pro Pro Ser Arg Asp Glu Leu
            370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
            405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
            435                 440                 445

Phe Ser Cys Ser Val Met His Glu Gly Leu His Asn His Tyr Thr Gln
            450                 455                 460

Lys Ser Leu Ser Leu Ser Pro Gly Lys
465                 470

<210> SEQ ID NO 89
<211> LENGTH: 473
<212> TYPE: PRT
<213> ORGANISM: Artificial Sequence
<220> FEATURE:
<223> OTHER INFORMATION: D120A

<400> SEQUENCE: 89

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
            35                  40                  45

Ser Gly Tyr Tyr Trp Gly Trp Ile Arg Gln Pro Pro Gly Lys Gly Leu
        50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
            85                  90                  95

Phe Ser Leu Lys Val Ser Ser Val Thr Ala Ala Asp Thr Ala Val Tyr
            100                 105                 110

Phe Cys Ala Arg Val Thr Arg Ala Leu Glu Trp Ile Pro Gly Asp Tyr
            115                 120                 125

Tyr Met Asp Val Trp Gly Lys Gly Thr Thr Val Thr Val Ser Ser Ala
            130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
            165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
            195                 200                 205

```
Ser Ser Val Val Thr Val Pro Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Gly Leu His Asn His Tyr Thr Gln
    450                 455                 460

Lys Ser Leu Ser Leu Ser Pro Gly Lys
465                 470

<210> SEQ ID NO 90
<211> LENGTH: 473
<212> TYPE: PRT
<213> ORGANISM: Artificial Sequence
<220> FEATURE:
<223> OTHER INFORMATION: E122D

<400> SEQUENCE: 90

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
```

```
            100                 105                 110
Phe Cys Ala Arg Val Thr Arg Asp Leu Asp Trp Ile Pro Gly Asp Tyr
            115                 120                 125
Tyr Met Asp Val Trp Gly Lys Gly Thr Thr Val Thr Val Ser Ser Ala
        130                 135                 140
Ser Thr Lys Gly Pro Ser Val Phe Pro Leu Ala Pro Ser Ser Lys Ser
145                 150                 155                 160
Thr Ser Gly Gly Thr Ala Ala Leu Gly Cys Leu Val Lys Asp Tyr Phe
                165                 170                 175
Pro Glu Pro Val Thr Val Ser Trp Asn Ser Gly Ala Leu Thr Ser Gly
            180                 185                 190
Val His Thr Phe Pro Ala Val Leu Gln Ser Ser Gly Leu Tyr Ser Leu
            195                 200                 205
Ser Ser Val Val Thr Val Pro Ser Ser Ser Leu Gly Thr Gln Thr Tyr
        210                 215                 220
Ile Cys Asn Val Asn His Lys Pro Ser Asn Thr Lys Val Asp Lys Lys
225                 230                 235                 240
Val Glu Pro Lys Ser Cys Asp Lys Thr His Thr Cys Pro Pro Cys Pro
                245                 250                 255
Ala Pro Glu Leu Leu Gly Gly Pro Ser Val Phe Leu Phe Pro Pro Lys
            260                 265                 270
Pro Lys Asp Thr Leu Met Ile Ser Arg Thr Pro Glu Val Thr Cys Val
            275                 280                 285
Val Val Asp Val Ser His Glu Asp Pro Glu Val Lys Phe Asn Trp Tyr
        290                 295                 300
Val Asp Gly Val Glu Val His Asn Ala Lys Thr Lys Pro Arg Glu Glu
305                 310                 315                 320
Gln Tyr Asn Ser Thr Tyr Arg Val Val Ser Val Leu Thr Val Leu His
                325                 330                 335
Gln Asp Trp Leu Asn Gly Lys Glu Tyr Lys Cys Lys Val Ser Asn Lys
            340                 345                 350
Ala Leu Pro Ala Pro Ile Glu Lys Thr Ile Ser Lys Ala Lys Gly Gln
            355                 360                 365
Pro Arg Glu Pro Gln Val Tyr Thr Leu Pro Pro Ser Arg Asp Glu Leu
        370                 375                 380
Thr Lys Asn Gln Val Ser Leu Thr Cys Leu Val Lys Gly Phe Tyr Pro
385                 390                 395                 400
Ser Asp Ile Ala Val Glu Trp Glu Ser Asn Gly Gln Pro Glu Asn Asn
                405                 410                 415
Tyr Lys Thr Thr Pro Pro Val Leu Asp Ser Asp Gly Ser Phe Phe Leu
            420                 425                 430
Tyr Ser Lys Leu Thr Val Asp Lys Ser Arg Trp Gln Gln Gly Asn Val
            435                 440                 445
Phe Ser Cys Ser Val Met His Glu Gly Leu His Asn His Tyr Thr Gln
        450                 455                 460
Lys Ser Leu Ser Leu Ser Pro Gly Lys
465                 470

<210> SEQ ID NO 91
<211> LENGTH: 473
<212> TYPE: PRT
<213> ORGANISM: Artificial Sequence
<220> FEATURE:
<223> OTHER INFORMATION: E122A

<400> SEQUENCE: 91
```

```
Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
                35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ser Ala Asn Ser Asn Pro
65                      70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
                100                 105                 110

Phe Cys Ala Arg Val Thr Arg Asp Leu Ala Trp Ile Pro Gly Asp Tyr
        115                 120                 125

Tyr Met Asp Val Trp Gly Lys Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
                180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
            405                 410                 415

Tyr Lys Thr Thr Pro Pro Val Leu Asp Ser Asp Gly Ser Phe Phe Leu
```

```
                           420                 425                 430
Tyr Ser Lys Leu Thr Val Asp Lys Ser Arg Trp Gln Gln Gly Asn Val
            435                 440                 445

Phe Ser Cys Ser Val Met His Glu Gly Leu His Asn His Tyr Thr Gln
        450                 455                 460

Lys Ser Leu Ser Leu Ser Pro Gly Lys
465                 470

<210> SEQ ID NO 92
<211> LENGTH: 473
<212> TYPE: PRT
<213> ORGANISM: Artificial Sequence
<220> FEATURE:
<223> OTHER INFORMATION: D127E

<400> SEQUENCE: 92

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
            100                 105                 110

Phe Cys Ala Arg Val Thr Arg Asp Leu Glu Trp Ile Pro Gly Glu Tyr
        115                 120                 125

Tyr Met Asp Val Trp Gly Lys Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320
```

Gln Tyr Asn Ser Thr Tyr Arg Val Val Ser Val Leu Thr Val Leu His
              325                 330                 335

Gln Asp Trp Leu Asn Gly Lys Glu Tyr Lys Cys Lys Val Ser Asn Lys
              340                 345                 350

Ala Leu Pro Ala Pro Ile Glu Lys Thr Ile Ser Lys Ala Lys Gly Gln
              355                 360                 365

Pro Arg Glu Pro Gln Val Tyr Thr Leu Pro Pro Ser Arg Asp Glu Leu
              370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
              405                 410                 415

Tyr Lys Thr Thr Pro Pro Val Leu Asp Ser Asp Gly Ser Phe Phe Leu
              420                 425                 430

Tyr Ser Lys Leu Thr Val Asp Lys Ser Arg Trp Gln Gln Gly Asn Val
              435                 440                 445

Phe Ser Cys Ser Val Met His Glu Gly Leu His Asn His Tyr Thr Gln
              450                 455                 460

Lys Ser Leu Ser Leu Ser Pro Gly Lys
465                 470

<210> SEQ ID NO 93
<211> LENGTH: 473
<212> TYPE: PRT
<213> ORGANISM: Artificial Sequence
<220> FEATURE:
<223> OTHER INFORMATION: D127A

<400> SEQUENCE: 93

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
              20                  25                  30

Pro Ser Glu Thr Leu Ser Leu Thr Cys Ala Val Tyr Gly Gly Ser Phe
              35                  40                  45

Ser Gly Tyr Tyr Trp Gly Trp Ile Arg Gln Pro Pro Gly Lys Gly Leu
              50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
              85                  90                  95

Phe Ser Leu Lys Val Ser Ser Val Thr Ala Ala Asp Thr Ala Val Tyr
              100                 105                 110

Phe Cys Ala Arg Val Thr Arg Asp Leu Glu Trp Ile Pro Gly Ala Tyr
              115                 120                 125

Tyr Met Asp Val Trp Gly Lys Gly Thr Thr Val Thr Val Ser Ser Ala
              130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
              165                 170                 175

Pro Glu Pro Val Thr Val Ser Trp Asn Ser Gly Ala Leu Thr Ser Gly
              180                 185                 190

Val His Thr Phe Pro Ala Val Leu Gln Ser Ser Gly Leu Tyr Ser Leu
              195                 200                 205

```
Ser Ser Val Val Thr Val Pro Ser Ser Leu Gly Thr Gln Thr Tyr
    210                 215                 220
Ile Cys Asn Val Asn His Lys Pro Ser Asn Thr Lys Val Asp Lys Lys
225                 230                 235                 240
Val Glu Pro Lys Ser Cys Asp Lys Thr His Thr Cys Pro Pro Cys Pro
                245                 250                 255
Ala Pro Glu Leu Leu Gly Gly Pro Ser Val Phe Leu Phe Pro Pro Lys
            260                 265                 270
Pro Lys Asp Thr Leu Met Ile Ser Arg Thr Pro Glu Val Thr Cys Val
        275                 280                 285
Val Val Asp Val Ser His Glu Asp Pro Glu Val Lys Phe Asn Trp Tyr
    290                 295                 300
Val Asp Gly Val Glu Val His Asn Ala Lys Thr Lys Pro Arg Glu Glu
305                 310                 315                 320
Gln Tyr Asn Ser Thr Tyr Arg Val Val Ser Val Leu Thr Val Leu His
                325                 330                 335
Gln Asp Trp Leu Asn Gly Lys Glu Tyr Lys Cys Lys Val Ser Asn Lys
            340                 345                 350
Ala Leu Pro Ala Pro Ile Glu Lys Thr Ile Ser Lys Ala Lys Gly Gln
        355                 360                 365
Pro Arg Glu Pro Gln Val Tyr Thr Leu Pro Pro Ser Arg Asp Glu Leu
    370                 375                 380
Thr Lys Asn Gln Val Ser Leu Thr Cys Leu Val Lys Gly Phe Tyr Pro
385                 390                 395                 400
Ser Asp Ile Ala Val Glu Trp Glu Ser Asn Gly Gln Pro Glu Asn Asn
                405                 410                 415
Tyr Lys Thr Thr Pro Pro Val Leu Asp Ser Asp Gly Ser Phe Phe Leu
            420                 425                 430
Tyr Ser Lys Leu Thr Val Asp Lys Ser Arg Trp Gln Gln Gly Asn Val
        435                 440                 445
Phe Ser Cys Ser Val Met His Glu Gly Leu His Asn His Tyr Thr Gln
    450                 455                 460
Lys Ser Leu Ser Leu Ser Pro Gly Lys
465                 470

<210> SEQ ID NO 94
<211> LENGTH: 473
<212> TYPE: PRT
<213> ORGANISM: Artificial Sequence
<220> FEATURE:
<223> OTHER INFORMATION: Y128F

<400> SEQUENCE: 94

Met Lys His Leu Trp Phe Phe Leu Leu Leu Val Ala Ala Pro Arg Trp
1               5                   10                  15
Val Leu Ser Gln Val Gln Leu Gln Gln Trp Gly Ala Gly Leu Leu Lys
            20                  25                  30
Pro Ser Glu Thr Leu Ser Leu Thr Cys Ala Val Tyr Gly Gly Ser Phe
        35                  40                  45
Ser Gly Tyr Tyr Trp Gly Trp Ile Arg Gln Pro Pro Gly Lys Gly Leu
    50                  55                  60
Glu Trp Ile Gly Glu Ile Asn His Ser Gly Ser Ala Asn Ser Asn Pro
65                  70                  75                  80
Ser Leu Lys Ser Arg Val Thr Met Ser Val Asp Thr Ser Lys Asn Gln
                85                  90                  95
Phe Ser Leu Lys Val Ser Ser Val Thr Ala Ala Asp Thr Ala Val Tyr
```

```
            100                 105                 110
Phe Cys Ala Arg Val Thr Arg Asp Leu Glu Trp Ile Pro Gly Asp Phe
            115                 120                 125
Tyr Met Asp Val Trp Gly Lys Gly Thr Thr Val Thr Val Ser Ser Ala
130                 135                 140
Ser Thr Lys Gly Pro Ser Val Phe Pro Leu Ala Pro Ser Ser Lys Ser
145                 150                 155                 160
Thr Ser Gly Gly Thr Ala Ala Leu Gly Cys Leu Val Lys Asp Tyr Phe
            165                 170                 175
Pro Glu Pro Val Thr Val Ser Trp Asn Ser Gly Ala Leu Thr Ser Gly
            180                 185                 190
Val His Thr Phe Pro Ala Val Leu Gln Ser Ser Gly Leu Tyr Ser Leu
            195                 200                 205
Ser Ser Val Val Thr Val Pro Ser Ser Ser Leu Gly Thr Gln Thr Tyr
            210                 215                 220
Ile Cys Asn Val Asn His Lys Pro Ser Asn Thr Lys Val Asp Lys Lys
225                 230                 235                 240
Val Glu Pro Lys Ser Cys Asp Lys Thr His Thr Cys Pro Pro Cys Pro
            245                 250                 255
Ala Pro Glu Leu Leu Gly Gly Pro Ser Val Phe Leu Phe Pro Pro Lys
            260                 265                 270
Pro Lys Asp Thr Leu Met Ile Ser Arg Thr Pro Glu Val Thr Cys Val
            275                 280                 285
Val Val Asp Val Ser His Glu Asp Pro Glu Val Lys Phe Asn Trp Tyr
            290                 295                 300
Val Asp Gly Val Glu Val His Asn Ala Lys Thr Lys Pro Arg Glu Glu
305                 310                 315                 320
Gln Tyr Asn Ser Thr Tyr Arg Val Val Ser Val Leu Thr Val Leu His
            325                 330                 335
Gln Asp Trp Leu Asn Gly Lys Glu Tyr Lys Cys Lys Val Ser Asn Lys
            340                 345                 350
Ala Leu Pro Ala Pro Ile Glu Lys Thr Ile Ser Lys Ala Lys Gly Gln
            355                 360                 365
Pro Arg Glu Pro Gln Val Tyr Thr Leu Pro Pro Ser Arg Asp Glu Leu
            370                 375                 380
Thr Lys Asn Gln Val Ser Leu Thr Cys Leu Val Lys Gly Phe Tyr Pro
385                 390                 395                 400
Ser Asp Ile Ala Val Glu Trp Glu Ser Asn Gly Gln Pro Glu Asn Asn
            405                 410                 415
Tyr Lys Thr Thr Pro Pro Val Leu Asp Ser Asp Gly Ser Phe Phe Leu
            420                 425                 430
Tyr Ser Lys Leu Thr Val Asp Lys Ser Arg Trp Gln Gln Gly Asn Val
            435                 440                 445
Phe Ser Cys Ser Val Met His Glu Gly Leu His Asn His Tyr Thr Gln
            450                 455                 460
Lys Ser Leu Ser Leu Ser Pro Gly Lys
465                 470

<210> SEQ ID NO 95
<211> LENGTH: 473
<212> TYPE: PRT
<213> ORGANISM: Artificial Sequence
<220> FEATURE:
<223> OTHER INFORMATION: Y128W

<400> SEQUENCE: 95
```

```
Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
                35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
                100                 105                 110

Phe Cys Ala Arg Val Thr Arg Asp Leu Glu Trp Ile Pro Gly Asp Trp
                115                 120                 125

Tyr Met Asp Val Trp Gly Lys Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
                180                 185                 190

Val His Thr Phe Pro Ala Val Leu Gln Ser Ser Gly Leu Tyr Ser Leu
    195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
                260                 265                 270

Pro Lys Asp Thr Leu Met Ile Ser Arg Thr Pro Glu Val Thr Cys Val
                275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
                340                 345                 350

Ala Leu Pro Ala Pro Ile Glu Lys Thr Ile Ser Lys Ala Lys Gly Gln
                355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
```

-continued

```
                420                 425                 430
Tyr Ser Lys Leu Thr Val Asp Lys Ser Arg Trp Gln Gln Gly Asn Val
            435                 440                 445

Phe Ser Cys Ser Val Met His Glu Gly Leu His Asn His Tyr Thr Gln
450                 455                 460

Lys Ser Leu Ser Leu Ser Pro Gly Lys
465                 470

<210> SEQ ID NO 96
<211> LENGTH: 473
<212> TYPE: PRT
<213> ORGANISM: Artificial Sequence
<220> FEATURE:
<223> OTHER INFORMATION: Y129F

<400> SEQUENCE: 96

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
            100                 105                 110

Phe Cys Ala Arg Val Thr Arg Asp Leu Glu Trp Ile Pro Gly Asp Tyr
        115                 120                 125

Phe Met Asp Val Trp Gly Lys Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320
```

```
Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Gly Leu His Asn His Tyr Thr Gln
    450                 455                 460

Lys Ser Leu Ser Leu Ser Pro Gly Lys
465                 470

<210> SEQ ID NO 97
<211> LENGTH: 473
<212> TYPE: PRT
<213> ORGANISM: Artificial Sequence
<220> FEATURE:
<223> OTHER INFORMATION: Y129W

<400> SEQUENCE: 97

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
            100                 105                 110

Phe Cys Ala Arg Val Thr Arg Asp Leu Glu Trp Ile Pro Gly Asp Tyr
        115                 120                 125

Trp Met Asp Val Trp Gly Lys Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205
```

| | | | | | | | | | | | |
|---|---|---|---|---|---|---|---|---|---|---|---|
|Ser|Ser|Val|Val|Thr|Val|Pro|Ser|Ser|Leu|Gly|Thr|Gln|Thr|Tyr|
| |210| | | |215| | | |220| | | | | |

```
Ser Ser Val Val Thr Val Pro Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Gly Leu His Asn His Tyr Thr Gln
    450                 455                 460

Lys Ser Leu Ser Leu Ser Pro Gly Lys
465                 470

<210> SEQ ID NO 98
<211> LENGTH: 473
<212> TYPE: PRT
<213> ORGANISM: Artificial Sequence
<220> FEATURE:
<223> OTHER INFORMATION: M130F

<400> SEQUENCE: 98

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
```

```
                100                 105                 110
Phe Cys Ala Arg Val Thr Arg Asp Leu Glu Trp Ile Pro Gly Asp Tyr
            115                 120                 125
Tyr Phe Asp Val Trp Gly Lys Gly Thr Thr Val Thr Val Ser Ser Ala
        130                 135                 140
Ser Thr Lys Gly Pro Ser Val Phe Pro Leu Ala Pro Ser Ser Lys Ser
145                 150                 155                 160
Thr Ser Gly Gly Thr Ala Ala Leu Gly Cys Leu Val Lys Asp Tyr Phe
                165                 170                 175
Pro Glu Pro Val Thr Val Ser Trp Asn Ser Gly Ala Leu Thr Ser Gly
            180                 185                 190
Val His Thr Phe Pro Ala Val Leu Gln Ser Ser Gly Leu Tyr Ser Leu
        195                 200                 205
Ser Ser Val Val Thr Val Pro Ser Ser Ser Leu Gly Thr Gln Thr Tyr
    210                 215                 220
Ile Cys Asn Val Asn His Lys Pro Ser Asn Thr Lys Val Asp Lys Lys
225                 230                 235                 240
Val Glu Pro Lys Ser Cys Asp Lys Thr His Thr Cys Pro Pro Cys Pro
                245                 250                 255
Ala Pro Glu Leu Leu Gly Gly Pro Ser Val Phe Leu Phe Pro Pro Lys
            260                 265                 270
Pro Lys Asp Thr Leu Met Ile Ser Arg Thr Pro Glu Val Thr Cys Val
        275                 280                 285
Val Val Asp Val Ser His Glu Asp Pro Glu Val Lys Phe Asn Trp Tyr
    290                 295                 300
Val Asp Gly Val Glu Val His Asn Ala Lys Thr Lys Pro Arg Glu Glu
305                 310                 315                 320
Gln Tyr Asn Ser Thr Tyr Arg Val Val Ser Val Leu Thr Val Leu His
                325                 330                 335
Gln Asp Trp Leu Asn Gly Lys Glu Tyr Lys Cys Lys Val Ser Asn Lys
            340                 345                 350
Ala Leu Pro Ala Pro Ile Glu Lys Thr Ile Ser Lys Ala Lys Gly Gln
        355                 360                 365
Pro Arg Glu Pro Gln Val Tyr Thr Leu Pro Pro Ser Arg Asp Glu Leu
    370                 375                 380
Thr Lys Asn Gln Val Ser Leu Thr Cys Leu Val Lys Gly Phe Tyr Pro
385                 390                 395                 400
Ser Asp Ile Ala Val Glu Trp Glu Ser Asn Gly Gln Pro Glu Asn Asn
                405                 410                 415
Tyr Lys Thr Thr Pro Pro Val Leu Asp Ser Asp Gly Ser Phe Phe Leu
            420                 425                 430
Tyr Ser Lys Leu Thr Val Asp Lys Ser Arg Trp Gln Gln Gly Asn Val
        435                 440                 445
Phe Ser Cys Ser Val Met His Glu Gly Leu His Asn His Tyr Thr Gln
    450                 455                 460
Lys Ser Leu Ser Leu Ser Pro Gly Lys
465                 470

<210> SEQ ID NO 99
<211> LENGTH: 473
<212> TYPE: PRT
<213> ORGANISM: Artificial Sequence
<220> FEATURE:
<223> OTHER INFORMATION: M130I

<400> SEQUENCE: 99
```

```
Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
            35                  40                  45

Ser Gly Tyr Tyr Trp Gly Trp Ile Arg Gln Pro Pro Gly Lys Gly Leu
50                  55                  60

Glu Trp Ile Gly Glu Ile Asn His Ser Gly Ser Ala Asn Ser Asn Pro
65                      70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
            100                 105                 110

Phe Cys Ala Arg Val Thr Arg Asp Leu Glu Trp Ile Pro Gly Asp Tyr
        115                 120                 125

Tyr Ile Asp Val Trp Gly Lys Gly Thr Thr Val Thr Val Ser Ser Ala
        130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
        210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
        290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
```

-continued

```
                420                 425                 430
Tyr Ser Lys Leu Thr Val Asp Lys Ser Arg Trp Gln Gln Gly Asn Val
                435                 440                 445

Phe Ser Cys Ser Val Met His Glu Gly Leu His Asn His Tyr Thr Gln
        450                 455                 460

Lys Ser Leu Ser Leu Ser Pro Gly Lys
465                 470

<210> SEQ ID NO 100
<211> LENGTH: 473
<212> TYPE: PRT
<213> ORGANISM: Artificial Sequence
<220> FEATURE:
<223> OTHER INFORMATION: D131E

<400> SEQUENCE: 100

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
            100                 105                 110

Phe Cys Ala Arg Val Thr Arg Asp Leu Glu Trp Ile Pro Gly Asp Tyr
        115                 120                 125

Tyr Met Glu Val Trp Gly Lys Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320
```

```
Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Gly Leu His Asn His Tyr Thr Gln
    450                 455                 460

Lys Ser Leu Ser Leu Ser Pro Gly Lys
465                 470

<210> SEQ ID NO 101
<211> LENGTH: 473
<212> TYPE: PRT
<213> ORGANISM: Artificial Sequence
<220> FEATURE:
<223> OTHER INFORMATION: D131A

<400> SEQUENCE: 101

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
            100                 105                 110

Phe Cys Ala Arg Val Thr Arg Asp Leu Glu Trp Ile Pro Gly Asp Tyr
        115                 120                 125

Tyr Met Ala Val Trp Gly Lys Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205
```

```
Ser Ser Val Val Thr Val Pro Ser Ser Leu Gly Thr Gln Thr Tyr
    210                 215                 220
Ile Cys Asn Val Asn His Lys Pro Ser Asn Thr Lys Val Asp Lys Lys
225                 230                 235                 240
Val Glu Pro Lys Ser Cys Asp Lys Thr His Thr Cys Pro Pro Cys Pro
                245                 250                 255
Ala Pro Glu Leu Leu Gly Gly Pro Ser Val Phe Leu Phe Pro Pro Lys
            260                 265                 270
Pro Lys Asp Thr Leu Met Ile Ser Arg Thr Pro Glu Val Thr Cys Val
        275                 280                 285
Val Val Asp Val Ser His Glu Asp Pro Glu Val Lys Phe Asn Trp Tyr
    290                 295                 300
Val Asp Gly Val Glu Val His Asn Ala Lys Thr Lys Pro Arg Glu Glu
305                 310                 315                 320
Gln Tyr Asn Ser Thr Tyr Arg Val Val Ser Val Leu Thr Val Leu His
                325                 330                 335
Gln Asp Trp Leu Asn Gly Lys Glu Tyr Lys Cys Lys Val Ser Asn Lys
            340                 345                 350
Ala Leu Pro Ala Pro Ile Glu Lys Thr Ile Ser Lys Ala Lys Gly Gln
        355                 360                 365
Pro Arg Glu Pro Gln Val Tyr Thr Leu Pro Pro Ser Arg Asp Glu Leu
    370                 375                 380
Thr Lys Asn Gln Val Ser Leu Thr Cys Leu Val Lys Gly Phe Tyr Pro
385                 390                 395                 400
Ser Asp Ile Ala Val Glu Trp Glu Ser Asn Gly Gln Pro Glu Asn Asn
                405                 410                 415
Tyr Lys Thr Thr Pro Pro Val Leu Asp Ser Asp Gly Ser Phe Phe Leu
            420                 425                 430
Tyr Ser Lys Leu Thr Val Asp Lys Ser Arg Trp Gln Gln Gly Asn Val
        435                 440                 445
Phe Ser Cys Ser Val Met His Glu Gly Leu His Asn His Tyr Thr Gln
    450                 455                 460
Lys Ser Leu Ser Leu Ser Pro Gly Lys
465                 470

<210> SEQ ID NO 102
<211> LENGTH: 473
<212> TYPE: PRT
<213> ORGANISM: Artificial Sequence
<220> FEATURE:
<223> OTHER INFORMATION: V132Y

<400> SEQUENCE: 102

Met Lys His Leu Trp Phe Phe Leu Leu Leu Val Ala Ala Pro Arg Trp
1               5                   10                  15
Val Leu Ser Gln Val Gln Leu Gln Gln Trp Gly Ala Gly Leu Leu Lys
            20                  25                  30
Pro Ser Glu Thr Leu Ser Leu Thr Cys Ala Val Tyr Gly Gly Ser Phe
        35                  40                  45
Ser Gly Tyr Tyr Trp Gly Trp Ile Arg Gln Pro Pro Gly Lys Gly Leu
    50                  55                  60
Glu Trp Ile Gly Glu Ile Asn His Ser Gly Ser Ala Asn Ser Asn Pro
65                  70                  75                  80
Ser Leu Lys Ser Arg Val Thr Met Ser Val Asp Thr Ser Lys Asn Gln
                85                  90                  95
Phe Ser Leu Lys Val Ser Ser Val Thr Ala Ala Asp Thr Ala Val Tyr
```

```
                  100                 105                 110
Phe Cys Ala Arg Val Thr Arg Asp Leu Glu Trp Ile Pro Gly Asp Tyr
            115                 120                 125
Tyr Met Asp Tyr Trp Gly Lys Gly Thr Thr Val Thr Val Ser Ser Ala
        130                 135                 140
Ser Thr Lys Gly Pro Ser Val Phe Pro Leu Ala Pro Ser Ser Lys Ser
145                 150                 155                 160
Thr Ser Gly Gly Thr Ala Ala Leu Gly Cys Leu Val Lys Asp Tyr Phe
                165                 170                 175
Pro Glu Pro Val Thr Val Ser Trp Asn Ser Gly Ala Leu Thr Ser Gly
            180                 185                 190
Val His Thr Phe Pro Ala Val Leu Gln Ser Ser Gly Leu Tyr Ser Leu
        195                 200                 205
Ser Ser Val Val Thr Val Pro Ser Ser Ser Leu Gly Thr Gln Thr Tyr
    210                 215                 220
Ile Cys Asn Val Asn His Lys Pro Ser Asn Thr Lys Val Asp Lys Lys
225                 230                 235                 240
Val Glu Pro Lys Ser Cys Asp Lys Thr His Thr Cys Pro Pro Cys Pro
                245                 250                 255
Ala Pro Glu Leu Leu Gly Gly Pro Ser Val Phe Leu Phe Pro Pro Lys
            260                 265                 270
Pro Lys Asp Thr Leu Met Ile Ser Arg Thr Pro Glu Val Thr Cys Val
        275                 280                 285
Val Val Asp Val Ser His Glu Asp Pro Glu Val Lys Phe Asn Trp Tyr
    290                 295                 300
Val Asp Gly Val Glu Val His Asn Ala Lys Thr Lys Pro Arg Glu Glu
305                 310                 315                 320
Gln Tyr Asn Ser Thr Tyr Arg Val Val Ser Val Leu Thr Val Leu His
                325                 330                 335
Gln Asp Trp Leu Asn Gly Lys Glu Tyr Lys Cys Lys Val Ser Asn Lys
            340                 345                 350
Ala Leu Pro Ala Pro Ile Glu Lys Thr Ile Ser Lys Ala Lys Gly Gln
        355                 360                 365
Pro Arg Glu Pro Gln Val Tyr Thr Leu Pro Pro Ser Arg Asp Glu Leu
    370                 375                 380
Thr Lys Asn Gln Val Ser Leu Thr Cys Leu Val Lys Gly Phe Tyr Pro
385                 390                 395                 400
Ser Asp Ile Ala Val Glu Trp Glu Ser Asn Gly Gln Pro Glu Asn Asn
                405                 410                 415
Tyr Lys Thr Thr Pro Pro Val Leu Asp Ser Asp Gly Ser Phe Phe Leu
            420                 425                 430
Tyr Ser Lys Leu Thr Val Asp Lys Ser Arg Trp Gln Gln Gly Asn Val
        435                 440                 445
Phe Ser Cys Ser Val Met His Glu Gly Leu His Asn His Tyr Thr Gln
    450                 455                 460
Lys Ser Leu Ser Leu Ser Pro Gly Lys
465                 470

<210> SEQ ID NO 103
<211> LENGTH: 473
<212> TYPE: PRT
<213> ORGANISM: Artificial Sequence
<220> FEATURE:
<223> OTHER INFORMATION: V132S

<400> SEQUENCE: 103
```

```
Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
                35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
                100                 105                 110

Phe Cys Ala Arg Val Thr Arg Asp Leu Glu Trp Ile Pro Gly Asp Tyr
            115                 120                 125

Tyr Met Asp Ser Trp Gly Lys Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
                180                 185                 190

Val His Thr Phe Pro Ala Val Leu Gln Ser Ser Gly Leu Tyr Ser Leu
            195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
    275                 280                 285

Val Val Asp Val Ser His Glu Asp Pro Glu Val Lys Phe Asn Trp Tyr
290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
    355                 360                 365

Pro Arg Glu Pro Gln Val Tyr Thr Leu Pro Pro Ser Arg Asp Glu Leu
370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
```

-continued

```
                     420                 425                 430
Tyr Ser Lys Leu Thr Val Asp Lys Ser Arg Trp Gln Gln Gly Asn Val
                435                 440                 445

Phe Ser Cys Ser Val Met His Glu Gly Leu His Asn His Tyr Thr Gln
            450                 455                 460

Lys Ser Leu Ser Leu Ser Pro Gly Lys
465                 470

<210> SEQ ID NO 104
<211> LENGTH: 473
<212> TYPE: PRT
<213> ORGANISM: Artificial Sequence
<220> FEATURE:
<223> OTHER INFORMATION: I124V/G126A

<400> SEQUENCE: 104

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
            100                 105                 110

Phe Cys Ala Arg Val Thr Arg Asp Leu Glu Trp Val Pro Ala Asp Tyr
        115                 120                 125

Tyr Met Asp Val Trp Gly Lys Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320
```

```
Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Gly Leu His Asn His Tyr Thr Gln
    450                 455                 460

Lys Ser Leu Ser Leu Ser Pro Gly Lys
465                 470

<210> SEQ ID NO 105
<211> LENGTH: 473
<212> TYPE: PRT
<213> ORGANISM: Artificial Sequence
<220> FEATURE:
<223> OTHER INFORMATION: I124V/G126S

<400> SEQUENCE: 105

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
            100                 105                 110

Phe Cys Ala Arg Val Thr Arg Asp Leu Glu Trp Val Pro Ser Asp Tyr
        115                 120                 125

Tyr Met Asp Val Trp Gly Lys Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205
```

```
Ser Ser Val Val Thr Val Pro Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Gly Leu His Asn His Tyr Thr Gln
    450                 455                 460

Lys Ser Leu Ser Leu Ser Pro Gly Lys
465                 470

<210> SEQ ID NO 106
<211> LENGTH: 473
<212> TYPE: PRT
<213> ORGANISM: Artificial Sequence
<220> FEATURE:
<223> OTHER INFORMATION: L121I/W123Y/I124V/G126A

<400> SEQUENCE: 106

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
```

```
                    100                 105                 110
Phe Cys Ala Arg Val Thr Arg Asp Ile Glu Tyr Val Pro Ala Asp Tyr
            115                 120                 125
Tyr Met Asp Val Trp Gly Lys Gly Thr Thr Val Thr Val Ser Ser Ala
        130                 135                 140
Ser Thr Lys Gly Pro Ser Val Phe Pro Leu Ala Pro Ser Ser Lys Ser
145                 150                 155                 160
Thr Ser Gly Gly Thr Ala Ala Leu Gly Cys Leu Val Lys Asp Tyr Phe
                165                 170                 175
Pro Glu Pro Val Thr Val Ser Trp Asn Ser Gly Ala Leu Thr Ser Gly
            180                 185                 190
Val His Thr Phe Pro Ala Val Leu Gln Ser Ser Gly Leu Tyr Ser Leu
        195                 200                 205
Ser Ser Val Val Thr Val Pro Ser Ser Ser Leu Gly Thr Gln Thr Tyr
210                 215                 220
Ile Cys Asn Val Asn His Lys Pro Ser Asn Thr Lys Val Asp Lys Lys
225                 230                 235                 240
Val Glu Pro Lys Ser Cys Asp Lys Thr His Thr Cys Pro Pro Cys Pro
                245                 250                 255
Ala Pro Glu Leu Leu Gly Gly Pro Ser Val Phe Leu Phe Pro Pro Lys
            260                 265                 270
Pro Lys Asp Thr Leu Met Ile Ser Arg Thr Pro Glu Val Thr Cys Val
        275                 280                 285
Val Val Asp Val Ser His Glu Asp Pro Glu Val Lys Phe Asn Trp Tyr
290                 295                 300
Val Asp Gly Val Glu Val His Asn Ala Lys Thr Lys Pro Arg Glu Glu
305                 310                 315                 320
Gln Tyr Asn Ser Thr Tyr Arg Val Val Ser Val Leu Thr Val Leu His
                325                 330                 335
Gln Asp Trp Leu Asn Gly Lys Glu Tyr Lys Cys Lys Val Ser Asn Lys
            340                 345                 350
Ala Leu Pro Ala Pro Ile Glu Lys Thr Ile Ser Lys Ala Lys Gly Gln
        355                 360                 365
Pro Arg Glu Pro Gln Val Tyr Thr Leu Pro Pro Ser Arg Asp Glu Leu
370                 375                 380
Thr Lys Asn Gln Val Ser Leu Thr Cys Leu Val Lys Gly Phe Tyr Pro
385                 390                 395                 400
Ser Asp Ile Ala Val Glu Trp Glu Ser Asn Gly Gln Pro Glu Asn Asn
                405                 410                 415
Tyr Lys Thr Thr Pro Pro Val Leu Asp Ser Asp Gly Ser Phe Phe Leu
            420                 425                 430
Tyr Ser Lys Leu Thr Val Asp Lys Ser Arg Trp Gln Gln Gly Asn Val
        435                 440                 445
Phe Ser Cys Ser Val Met His Glu Gly Leu His Asn His Tyr Thr Gln
        450                 455                 460
Lys Ser Leu Ser Leu Ser Pro Gly Lys
465                 470

<210> SEQ ID NO 107
<211> LENGTH: 473
<212> TYPE: PRT
<213> ORGANISM: Artificial Sequence
<220> FEATURE:
<223> OTHER INFORMATION: L121I/W123Y/I124V/G126S

<400> SEQUENCE: 107
```

```
Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
            35                  40                  45

Ser Gly Tyr Tyr Trp Gly Trp Ile Arg Gln Pro Pro Gly Lys Gly Leu
        50                  55                  60

Glu Trp Ile Gly Glu Ile Asn His Ser Gly Ser Ala Asn Ser Asn Pro
65                      70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
            100                 105                 110

Phe Cys Ala Arg Val Thr Arg Asp Ile Glu Tyr Val Pro Ser Asp Tyr
        115                 120                 125

Tyr Met Asp Val Trp Gly Lys Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
```

```
                    420                 425                 430
Tyr Ser Lys Leu Thr Val Asp Lys Ser Arg Trp Gln Gln Gly Asn Val
                435                 440                 445

Phe Ser Cys Ser Val Met His Glu Gly Leu His Asn His Tyr Thr Gln
            450                 455                 460

Lys Ser Leu Ser Leu Ser Pro Gly Lys
465                 470

<210> SEQ ID NO 108
<211> LENGTH: 472
<212> TYPE: PRT
<213> ORGANISM: Artificial Sequence
<220> FEATURE:
<223> OTHER INFORMATION: E122del

<400> SEQUENCE: 108

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Val Thr Ala Ala Asp Thr Ala Val Tyr
            100                 105                 110

Phe Cys Ala Arg Val Thr Arg Asp Leu Trp Ile Pro Gly Asp Tyr Tyr
        115                 120                 125

Met Asp Val Trp Gly Lys Gly Thr Thr Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320
```

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Asp Glu Leu Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Gly Leu His Asn His Tyr Thr Gln Lys
    450                 455                 460

Ser Leu Ser Leu Ser Pro Gly Lys
465                 470

<210> SEQ ID NO 109
<211> LENGTH: 474
<212> TYPE: PRT
<213> ORGANISM: Artificial Sequence
<220> FEATURE:
<223> OTHER INFORMATION: G126_D127insE

<400> SEQUENCE: 109

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ser Ala Asn Ser Asn Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
            100                 105                 110

Phe Cys Ala Arg Val Thr Arg Asp Leu Glu Trp Ile Pro Gly Glu Asp
        115                 120                 125

Tyr Tyr Met Asp Val Trp Gly Lys Gly Thr Thr Val Thr Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

```
Leu Ser Ser Val Val Thr Val Pro Ser Ser Leu Gly Thr Gln Thr
    210                 215                 220

Tyr Ile Cys Asn Val Asn His Lys Pro Ser Asn Thr Lys Val Asp Lys
225                 230                 235                 240

Lys Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Asp Glu
    370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Gly Leu His Asn His Tyr Thr
    450                 455                 460

Gln Lys Ser Leu Ser Leu Ser Pro Gly Lys
465                 470

<210> SEQ ID NO 110
<211> LENGTH: 473
<212> TYPE: PRT
<213> ORGANISM: Artificial Sequence
<220> FEATURE:
<223> OTHER INFORMATION: N79Q

<400> SEQUENCE: 110

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Gly Trp Ile Arg Gln Pro Pro Gly Lys Gly Leu
    50                  55                  60

Glu Trp Ile Gly Glu Ile Asn His Ser Gly Ser Ala Asn Ser Gln Pro
65                  70                  75                  80

Ser Leu Lys Ser Arg Val Thr Met Ser Val Asp Thr Ser Lys Asn Gln
                85                  90                  95

Phe Ser Leu Lys Val Ser Ser Val Thr Ala Ala Asp Thr Ala Val Tyr
```

```
            100                 105                 110
Phe Cys Ala Arg Val Thr Arg Asp Leu Glu Trp Ile Pro Gly Asp Tyr
            115                 120                 125
Tyr Met Asp Val Trp Gly Lys Gly Thr Thr Val Thr Val Ser Ser Ala
        130                 135                 140
Ser Thr Lys Gly Pro Ser Val Phe Pro Leu Ala Pro Ser Ser Lys Ser
145                 150                 155                 160
Thr Ser Gly Gly Thr Ala Ala Leu Gly Cys Leu Val Lys Asp Tyr Phe
                165                 170                 175
Pro Glu Pro Val Thr Val Ser Trp Asn Ser Gly Ala Leu Thr Ser Gly
                180                 185                 190
Val His Thr Phe Pro Ala Val Leu Gln Ser Ser Gly Leu Tyr Ser Leu
                195                 200                 205
Ser Ser Val Val Thr Val Pro Ser Ser Ser Leu Gly Thr Gln Thr Tyr
        210                 215                 220
Ile Cys Asn Val Asn His Lys Pro Ser Asn Thr Lys Val Asp Lys Lys
225                 230                 235                 240
Val Glu Pro Lys Ser Cys Asp Lys Thr His Thr Cys Pro Pro Cys Pro
                245                 250                 255
Ala Pro Glu Leu Leu Gly Gly Pro Ser Val Phe Leu Phe Pro Pro Lys
                260                 265                 270
Pro Lys Asp Thr Leu Met Ile Ser Arg Thr Pro Glu Val Thr Cys Val
                275                 280                 285
Val Val Asp Val Ser His Glu Asp Pro Glu Val Lys Phe Asn Trp Tyr
                290                 295                 300
Val Asp Gly Val Glu Val His Asn Ala Lys Thr Lys Pro Arg Glu Glu
305                 310                 315                 320
Gln Tyr Asn Ser Thr Tyr Arg Val Val Ser Val Leu Thr Val Leu His
                325                 330                 335
Gln Asp Trp Leu Asn Gly Lys Glu Tyr Lys Cys Lys Val Ser Asn Lys
                340                 345                 350
Ala Leu Pro Ala Pro Ile Glu Lys Thr Ile Ser Lys Ala Lys Gly Gln
                355                 360                 365
Pro Arg Glu Pro Gln Val Tyr Thr Leu Pro Pro Ser Arg Asp Glu Leu
        370                 375                 380
Thr Lys Asn Gln Val Ser Leu Thr Cys Leu Val Lys Gly Phe Tyr Pro
385                 390                 395                 400
Ser Asp Ile Ala Val Glu Trp Glu Ser Asn Gly Gln Pro Glu Asn Asn
                405                 410                 415
Tyr Lys Thr Thr Pro Pro Val Leu Asp Ser Asp Gly Ser Phe Phe Leu
                420                 425                 430
Tyr Ser Lys Leu Thr Val Asp Lys Ser Arg Trp Gln Gln Gly Asn Val
                435                 440                 445
Phe Ser Cys Ser Val Met His Glu Gly Leu His Asn His Tyr Thr Gln
                450                 455                 460
Lys Ser Leu Ser Leu Ser Pro Gly Lys
465                 470

<210> SEQ ID NO 111
<211> LENGTH: 12
<212> TYPE: PRT
<213> ORGANISM: Artificial Sequence
<220> FEATURE:
<223> OTHER INFORMATION: Synthetic peptide

<400> SEQUENCE: 111
```

```
Met Gly Asp Val Leu Gly Leu Ala Ser Cys Val Thr
1               5                   10
```

<210> SEQ ID NO 112
<211> LENGTH: 12
<212> TYPE: PRT
<213> ORGANISM: Artificial Sequence
<220> FEATURE:
<223> OTHER INFORMATION: Synthetic peptide

<400> SEQUENCE: 112

```
Leu Gly Leu Ala Ser Cys Val Thr Ile Asn Gln Thr
1               5                   10
```

<210> SEQ ID NO 113
<211> LENGTH: 12
<212> TYPE: PRT
<213> ORGANISM: Artificial Sequence
<220> FEATURE:
<223> OTHER INFORMATION: Synthetic peptide

<400> SEQUENCE: 113

```
Ser Cys Val Thr Ile Asn Gln Thr Ser Val Lys Val
1               5                   10
```

<210> SEQ ID NO 114
<211> LENGTH: 12
<212> TYPE: PRT
<213> ORGANISM: Artificial Sequence
<220> FEATURE:
<223> OTHER INFORMATION: Synthetic peptide

<400> SEQUENCE: 114

```
Ile Asn Gln Thr Ser Val Lys Val Leu Arg Asp Met
1               5                   10
```

<210> SEQ ID NO 115
<211> LENGTH: 12
<212> TYPE: PRT
<213> ORGANISM: Artificial Sequence
<220> FEATURE:
<223> OTHER INFORMATION: Synthetic peptide

<400> SEQUENCE: 115

```
Ser Val Lys Val Leu Arg Asp Met Asn Val Lys Glu
1               5                   10
```

<210> SEQ ID NO 116
<211> LENGTH: 12
<212> TYPE: PRT
<213> ORGANISM: Artificial Sequence
<220> FEATURE:
<223> OTHER INFORMATION: Synthetic peptide

<400> SEQUENCE: 116

```
Leu Arg Asp Met Asn Val Lys Glu Ser Pro Gly Arg
1               5                   10
```

<210> SEQ ID NO 117
<211> LENGTH: 12
<212> TYPE: PRT
<213> ORGANISM: Artificial Sequence
<220> FEATURE:
<223> OTHER INFORMATION: Synthetic peptide

<400> SEQUENCE: 117

```
Asn Val Lys Glu Ser Pro Gly Arg Cys Tyr Ser Arg
```

```
1               5                   10
```

<210> SEQ ID NO 118
<211> LENGTH: 12
<212> TYPE: PRT
<213> ORGANISM: Artificial Sequence
<220> FEATURE:
<223> OTHER INFORMATION: Synthetic peptide

<400> SEQUENCE: 118

```
Ser Pro Gly Arg Cys Tyr Ser Arg Pro Val Val Ile
1               5                   10
```

<210> SEQ ID NO 119
<211> LENGTH: 12
<212> TYPE: PRT
<213> ORGANISM: Artificial Sequence
<220> FEATURE:
<223> OTHER INFORMATION: Synthetic peptide

<400> SEQUENCE: 119

```
Cys Tyr Ser Arg Pro Val Val Ile Phe Asn Phe Ala
1               5                   10
```

<210> SEQ ID NO 120
<211> LENGTH: 12
<212> TYPE: PRT
<213> ORGANISM: Artificial Sequence
<220> FEATURE:
<223> OTHER INFORMATION: Synthetic peptide

<400> SEQUENCE: 120

```
Pro Val Val Ile Phe Asn Phe Ala Asn Ser Ser Tyr
1               5                   10
```

<210> SEQ ID NO 121
<211> LENGTH: 12
<212> TYPE: PRT
<213> ORGANISM: Artificial Sequence
<220> FEATURE:
<223> OTHER INFORMATION: Synthetic peptide

<400> SEQUENCE: 121

```
Phe Asn Phe Ala Asn Ser Ser Tyr Val Gln Tyr Gly
1               5                   10
```

<210> SEQ ID NO 122
<211> LENGTH: 12
<212> TYPE: PRT
<213> ORGANISM: Artificial Sequence
<220> FEATURE:
<223> OTHER INFORMATION: Synthetic peptide

<400> SEQUENCE: 122

```
Asn Ser Ser Tyr Val Gln Tyr Gly Gln Leu Gly Glu
1               5                   10
```

<210> SEQ ID NO 123
<211> LENGTH: 12
<212> TYPE: PRT
<213> ORGANISM: Artificial Sequence
<220> FEATURE:
<223> OTHER INFORMATION: Synthetic peptide

<400> SEQUENCE: 123

```
Val Gln Tyr Gly Gln Leu Gly Glu Asp Asn Glu Ile
1               5                   10
```

```
<210> SEQ ID NO 124
<211> LENGTH: 12
<212> TYPE: PRT
<213> ORGANISM: Artificial Sequence
<220> FEATURE:
<223> OTHER INFORMATION: Synthetic peptide

<400> SEQUENCE: 124

Gln Leu Gly Glu Asp Asn Glu Ile Leu Leu Gly Asn
1               5                   10

<210> SEQ ID NO 125
<211> LENGTH: 12
<212> TYPE: PRT
<213> ORGANISM: Artificial Sequence
<220> FEATURE:
<223> OTHER INFORMATION: Synthetic peptide

<400> SEQUENCE: 125

Asp Asn Glu Ile Leu Leu Gly Asn His Arg Thr Glu
1               5                   10

<210> SEQ ID NO 126
<211> LENGTH: 12
<212> TYPE: PRT
<213> ORGANISM: Artificial Sequence
<220> FEATURE:
<223> OTHER INFORMATION: Synthetic peptide

<400> SEQUENCE: 126

Leu Leu Gly Asn His Arg Thr Glu Glu Cys Gln Leu
1               5                   10

<210> SEQ ID NO 127
<211> LENGTH: 12
<212> TYPE: PRT
<213> ORGANISM: Artificial Sequence
<220> FEATURE:
<223> OTHER INFORMATION: Synthetic peptide

<400> SEQUENCE: 127

His Arg Thr Glu Glu Cys Gln Leu Pro Ser Leu Lys
1               5                   10

<210> SEQ ID NO 128
<211> LENGTH: 12
<212> TYPE: PRT
<213> ORGANISM: Artificial Sequence
<220> FEATURE:
<223> OTHER INFORMATION: Synthetic peptide

<400> SEQUENCE: 128

Glu Cys Gln Leu Pro Ser Leu Lys Ile Phe Ile Ala
1               5                   10

<210> SEQ ID NO 129
<211> LENGTH: 12
<212> TYPE: PRT
<213> ORGANISM: Artificial Sequence
<220> FEATURE:
<223> OTHER INFORMATION: Synthetic peptide

<400> SEQUENCE: 129

Pro Ser Leu Lys Ile Phe Ile Ala Gly Asn Ser Ala
1               5                   10

<210> SEQ ID NO 130
```

```
<211> LENGTH: 12
<212> TYPE: PRT
<213> ORGANISM: Artificial Sequence
<220> FEATURE:
<223> OTHER INFORMATION: Synthetic peptide

<400> SEQUENCE: 130

Ile Phe Ile Ala Gly Asn Ser Ala Tyr Glu Tyr Val
1               5                   10

<210> SEQ ID NO 131
<211> LENGTH: 12
<212> TYPE: PRT
<213> ORGANISM: Artificial Sequence
<220> FEATURE:
<223> OTHER INFORMATION: Synthetic peptide

<400> SEQUENCE: 131

Gly Asn Ser Ala Tyr Glu Tyr Val Asp Tyr Leu Phe
1               5                   10

<210> SEQ ID NO 132
<211> LENGTH: 12
<212> TYPE: PRT
<213> ORGANISM: Artificial Sequence
<220> FEATURE:
<223> OTHER INFORMATION: Synthetic peptide

<400> SEQUENCE: 132

Tyr Glu Tyr Val Asp Tyr Leu Phe Lys Arg Met Ile
1               5                   10

<210> SEQ ID NO 133
<211> LENGTH: 12
<212> TYPE: PRT
<213> ORGANISM: Artificial Sequence
<220> FEATURE:
<223> OTHER INFORMATION: Synthetic peptide

<400> SEQUENCE: 133

Asp Tyr Leu Phe Lys Arg Met Ile Asp Leu Ser Ser
1               5                   10

<210> SEQ ID NO 134
<211> LENGTH: 12
<212> TYPE: PRT
<213> ORGANISM: Artificial Sequence
<220> FEATURE:
<223> OTHER INFORMATION: Synthetic peptide

<400> SEQUENCE: 134

Lys Arg Met Ile Asp Leu Ser Ser Ile Ser Thr Val
1               5                   10

<210> SEQ ID NO 135
<211> LENGTH: 12
<212> TYPE: PRT
<213> ORGANISM: Artificial Sequence
<220> FEATURE:
<223> OTHER INFORMATION: Synthetic peptide

<400> SEQUENCE: 135

Asp Leu Ser Ser Ile Ser Thr Val Asp Ser Met Ile
1               5                   10

<210> SEQ ID NO 136
<211> LENGTH: 12
<212> TYPE: PRT
```

-continued

```
<213> ORGANISM: Artificial Sequence
<220> FEATURE:
<223> OTHER INFORMATION: Synthetic peptide

<400> SEQUENCE: 136

Ile Ser Thr Val Asp Ser Met Ile Ala Leu Asp Ile
1               5                   10

<210> SEQ ID NO 137
<211> LENGTH: 906
<212> TYPE: PRT
<213> ORGANISM: Human cytomegalovirus
<300> PUBLICATION INFORMATION:
<308> DATABASE ACCESSION NUMBER: Swiss-Prot/P06473
<309> DATABASE ENTRY DATE: 1988-01-01
<313> RELEVANT RESIDUES IN SEQ ID NO: (1)..(906)

<400> SEQUENCE: 137

Met Glu Ser Arg Ile Trp Cys Leu Val Val Cys Val Asn Leu Cys Ile
1               5                   10                  15

Val Cys Leu Gly Ala Ala Val Ser Ser Ser Thr Ser His Ala Thr
                20                  25                  30

Ser Ser Thr His Asn Gly Ser His Thr Ser Arg Thr Thr Ser Ala Gln
            35                  40                  45

Thr Arg Ser Val Tyr Ser Gln His Val Thr Ser Ser Glu Ala Val Ser
        50                  55                  60

His Arg Ala Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Ile Cys Thr
            100                 105                 110

Ser Met Lys Pro Ile Asn Glu Asp Leu Asp Glu Gly Ile Met Val Val
        115                 120                 125

Tyr Lys Arg Asn Ile Val Ala His Thr Phe Lys Val Arg Val Tyr Gln
    130                 135                 140

Lys Val Leu Thr Phe Arg Arg Ser Tyr Ala Tyr Ile Tyr Thr Thr Tyr
145                 150                 155                 160

Leu Leu Gly Ser Asn Thr Glu Tyr Val Ala Pro Pro Met Trp Glu Ile
                165                 170                 175

His His Ile Asn Lys Phe Ala Gln Cys Tyr Ser Ser Tyr Ser Arg Val
            180                 185                 190

Ile Gly Gly Thr Val Phe Val Ala Tyr His Arg Asp Ser Tyr Glu Asn
        195                 200                 205

Lys Thr Met Gln Leu Ile Pro Asp Asp Tyr Ser Asn Thr His Ser Thr
    210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Leu Thr Ile Thr Thr
                245                 250                 255

Ala Arg Ser Lys Tyr Pro Tyr His Phe Phe Ala Thr Ser Thr Gly Asp
            260                 265                 270

Val Val Tyr Ile Ser Pro Phe Tyr Asn Gly Thr Asn Arg Asn Ala Ser
        275                 280                 285

Tyr Phe Gly Glu Asn Ala Asp Lys Phe Phe Ile Phe Pro Asn Tyr Thr
    290                 295                 300

Ile Val Ser Asp Phe Gly Arg Pro Asn Ala Ala Pro Glu Thr His Arg
305                 310                 315                 320
```

-continued

Leu Val Ala Phe Leu Glu Arg Ala Asp Ser Val Ile Ser Trp Asp Ile
              325                 330                 335

Gln Asp Glu Lys Asn Val Thr Cys Gln Leu Thr Phe Trp Glu Ala Ser
              340                 345                 350

Glu Arg Thr Ile Arg Ser Glu Ala Glu Asp Ser Tyr His Phe Ser Ser
              355                 360                 365

Ala Lys Met Thr Ala Thr Phe Leu Ser Lys Lys Gln Glu Val Asn Met
              370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
                  405                 410                 415

Asn Val Ser Val Phe Glu Thr Ser Gly Gly Leu Val Val Phe Trp Gln
              420                 425                 430

Gly Ile Lys Gln Lys Ser Leu Val Glu Leu Glu Arg Leu Ala Asn Arg
              435                 440                 445

Ser Ser Leu Asn Ile Thr His Arg Thr Arg Ser Thr Ser Asp Asn
450                 455                 460

Asn Thr Thr His Leu Ser Ser Met Glu Ser Val His Asn Leu Val Tyr
465                 470                 475                 480

Ala Gln Leu Gln Phe Thr Tyr Asp Thr Leu Arg Gly Tyr Ile Asn Arg
                  485                 490                 495

Ala Leu Ala Gln Ile Ala Glu Ala Trp Cys Val Asp Gln Arg Arg Thr
              500                 505                 510

Leu Glu Val Phe Lys Glu Leu Ser Lys Ile Asn Pro Ser Ala Ile Leu
              515                 520                 525

Ser Ala Ile Tyr Asn Lys Pro Ile Ala Ala Arg Phe Met Gly Asp Val
              530                 535                 540

Leu Gly Leu Ala Ser Cys Val Thr Ile Asn Gln Thr Ser Val Lys Val
545                 550                 555                 560

Leu Arg Asp Met Asn Val Lys Glu Ser Pro Gly Arg Cys Tyr Ser Arg
                  565                 570                 575

Pro Val Val Ile Phe Asn Phe Ala Asn Ser Ser Tyr Val Gln Tyr Gly
              580                 585                 590

Gln Leu Gly Glu Asp Asn Glu Ile Leu Leu Gly Asn His Arg Thr Glu
              595                 600                 605

Glu Cys Gln Leu Pro Ser Leu Lys Ile Phe Ile Ala Gly Asn Ser Ala
610                 615                 620

Tyr Glu Tyr Val Asp Tyr Leu Phe Lys Arg Met Ile Asp Leu Ser Ser
625                 630                 635                 640

Ile Ser Thr Val Asp Ser Met Ile Ala Leu Asp Ile Asp Pro Leu Glu
                  645                 650                 655

Asn Thr Asp Phe Arg Val Leu Glu Leu Tyr Ser Gln Lys Glu Leu Arg
              660                 665                 670

Ser Ser Asn Val Phe Asp Leu Glu Glu Ile Met Arg Glu Phe Asn Ser
              675                 680                 685

Tyr Lys Gln Arg Val Lys Tyr Val Glu Asp Lys Val Val Asp Pro Leu
              690                 695                 700

Pro Pro Tyr Leu Lys Gly Leu Asp Asp Leu Met Ser Gly Leu Gly Ala
705                 710                 715                 720

Ala Gly Lys Ala Val Gly Val Ala Ile Gly Ala Val Gly Gly Ala Val
                  725                 730                 735

Ala Ser Val Val Glu Gly Val Ala Thr Phe Leu Lys Asn Pro Phe Gly

-continued

```
                740                 745                 750
Ala Phe Thr Ile Ile Leu Val Ala Ile Ala Val Val Ile Ile Thr Tyr
        755                 760                 765

Leu Ile Tyr Thr Arg Gln Arg Arg Leu Cys Thr Gln Pro Leu Gln Asn
    770                 775                 780

Leu Phe Pro Tyr Leu Val Ser Ala Asp Gly Thr Val Thr Ser Gly
785                 790                 795                 800

Ser Thr Lys Asp Thr Ser Leu Gln Ala Pro Pro Ser Tyr Glu Glu Ser
                805                 810                 815

Val Tyr Asn Ser Gly Arg Lys Gly Pro Gly Pro Pro Ser Ser Asp Ala
            820                 825                 830

Ser Thr Ala Ala Pro Pro Tyr Thr Asn Glu Gln Ala Tyr Gln Met Leu
        835                 840                 845

Leu Ala Leu Ala Arg Leu Asp Ala Glu Gln Arg Ala Gln Gln Asn Gly
    850                 855                 860

Thr Asp Ser Leu Asp Gly Gln Thr Gly Thr Gln Asp Lys Gly Gln Lys
865                 870                 875                 880

Pro Asn Leu Leu Asp Arg Leu Arg His Arg Lys Asn Gly Tyr Arg His
                885                 890                 895

Leu Lys Asp Ser Asp Glu Glu Glu Asn Val
                900                 905
```

MONOCLONAL ANTIBODY CAPABLE OF BINDING TO SPECIFIC DISCONTINUOUS EPITOPE OCCURRING IN AD1 REGION OF HUMAN CYTOMEGALOVIRUS GB GLYCOPROTEIN, AND ANTIGEN-BINDING FRAGMENT THEREOF

CROSS-REFERENCE TO RELATED APPLICATIONS

This application is a National Stage application of PCT/JP 2010/056037, filed Apr. 1, 2010, which claims priority from Japanese application JP 2009-089442, filed Apr. 1, 2009.

TECHNICAL FIELD

The present invention relates to a monoclonal antibody that binds to human cytomegalovirus (hereinafter, sometimes referred to as "HCMV"), and an antigen-binding fragment thereof. More particularly, the present invention relates to a human monoclonal antibody that binds to AD1 region of HCMV glycoprotein gB and an antigen-binding fragment thereof.

BACKGROUND ART

Along with human herpesvirus-6 (HHV-6) and human herpesvirus-7 (HHV-7), human cytomegalovirus (HCMV) belongs to beta-herpesvirus of Herpesviridae. HCMV is a double-stranded DNA virus that is the largest among Herpesviridae with a diameter of approximately 180 nm, where the wild strain thereof encodes 165 genes with a genome size of approximately 235 kbp (Non-Patent Documents 1 and 2).

HCMV is highly species-specific and does not infect animals other than human but it widely infects human and has affinity for broad types of tissues in human body.

Moreover, once infected, HCMV is not eliminated even after the establishment of immunity in the host and remains lifelong.

Once infected, HCMV remain latent over a lifetime. More than 90% of Japanese adults are already infected and carry the virus, although the virus is rarely activated and rarely produce diseases in healthy people.

However, an immunodeficiency state due to AIDS, due to cancer, after organ transplantation, after bone-marrow transplantation, after hemodialysis or the like could cause reactivation of the latent HCMV, which may cause serious HCMV infection that may be fatal such as interstitial pneumonia, retinitis, gastroenteritis, encephalitis or the like (Non-Patent Documents 3 and 4).

Furthermore, when a pregnant woman experiences primary infection by HCMV during the fetal period, HCMV infection may be transmitted to the fetus from the pregnant woman via the placenta, in which case the fetus may develop congenital CMV infection (congenital cytomegalovirus disease: also called cytomegalic inclusion disease or congenital cytomegalic inclusion disease), and may result in miscarriage, stillbirth or death shortly after birth. Even in the case of survival, it may result in low birth weight, hepatosplenomegaly, jaundice, thrombocytopenic purpura, microcephaly, disorder of mental development, delay of intellectual development, chorioretinitis, hearing impairment or the like. In addition, even during newborn period or infancy, if HCMV antibody transmitted from the mother is insufficient, HCMV infection via birth canal, breast milk, urine, saliva or the like may develop abnormality of hepatic function, interstitial pneumonia, mononucleosis or the like (Non-Patent Documents 3,4 and 5).

HCMV infection has become a worldwide issue and prophylactic and therapeutic drugs that are capable of suppressing onsets of various pathological conditions due to the above-described HCMV, or that are capable of alleviating such pathological conditions are currently under development. Recently, ganciclovir (Non-Patent Documents 6 and 7), foscarnet (Non-Patent Document 8), valganciclovir (Non-Patent Document 9) and the like have been developed as antiviral drugs for suppressing HCMV proliferation.

Ganciclovir is an antiviral drug that blocks synthesis of viral DNA, which is activated to ganciclovir triphosphate in cells and competitively antagonize with deoxyguanosine triphosphate (dGTP), i.e., a substrate of DNA polymerase, thereby inhibiting DNA polymerase. Hence, it is used for treating cytomegalovirus retinitis in an immunodeficiency state, mainly AIDS, or used for suppressing onset of cytomegalovirus retinitis in advanced HIV infection with 100 or less CD4 lymphocytes/$mm^3$, and approved as a pharmaceutical product.

Antiviral agents such as ganciclovir, however, have been reported of various side effects such as hematopoietic disorder, and their mode of use has been very limited as described above.

The most frequently-occurring and attention-requiring side effect among the side effects of ganciclovir is blood disorders associated with bone-marrow suppression, where the numbers of leukocytes, erythrocytes and platelets are abnormally decreased. The early symptoms include fever, sore throat, abnormal sluggishness and bleeding tendency such as bleeding beneath the skin In some cases, it may cause abnormality in the psyconeurotic system, resulting in headache, dizziness, insomnia, difficulty with thinking, feeling of anxiety or the like.

In addition, teratogenesis, mutagenicity and carcinogenicity have been reported in animal experiments, and thus it cannot be used during pregnancy.

Furthermore, although use of ganciclovir in severe cases of congenital HCMV infection is thought to be effective in decreasing onset of neurological aftereffects and improving progression of hearing loss (Non-Patent Document 10), problems of bone-marrow suppression, teratogenesis or carcinogenicity as side effects of ganciclovir still require sufficient and careful consideration.

Valganciclovir is L-valine ester of ganciclovir which is converted to ganciclovir with intestinal and hepatic esterases after oral administration. Accordingly, its mechanism of action and side effects are the same as those of ganciclovir and thus associated with the problems of bone-marrow suppression, teratogenesis and carcinogenicity. In Japan, valganciclovir is approved as a therapeutic drug for cytomegalovirus retinitis in immunodeficiency states, mainly AIDS.

Meanwhile, foscarnet is an analog of pyrophosphoric acid and suppresses HCMV proliferation by directly acting on the pyrophosphoric acid-binding site of DNA polymerase to inhibit DNA polymerase. It is also effective against ganciclovir-resistant HCMV. Main side effects include feeling of sickness, anemia, increase in serum creatinine, vomiting, hypomagnesemia, hypokalemia, abnormal sensation and the like. In particular, shock and kidney damage frequently occur and thus requires careful administration. In Japan, use of foscarnet is permitted only in patients determinably diagnosed to have HCMV retinitis or patients highly and clinically suspicious of HCMV retinitis among the AIDS patients, and not to be used for the purpose of prevention of infection (Non-Patent Document 8).

Thus, development of a drug capable of preventing onset of various diseases due to the above-described HCMV or alleviating symptoms thereof without any side effect has been strongly desired. Under the circumstances, clinical developments of two anti-HCMV antibodies have been carried out, where one is anti-HCMV antibody "C23 (also called TI-23 at the time of development)" described in Patent Document 3 which is an antibody that recognizes the AD2 region of glycoprotein gB, and the other is anti-HCMV antibody "SDZ MSL 109" described in Patent Document 4 which is a monoclonal antibody that recognizes the glycoprotein gH on the surface of the HCMV. Particularly, development of C23 was abandoned along the way despite of its high neutralizing activity, i.e. 50% inhibitory concentration of 0.5 µg/mL as determined by plaque method (Non-Patent Document 11).

For the time being, development of HCMV vaccine has been keenly conducted but no vaccine is still available that can endure clinical use. A formulation of human-derived anti-CMV high-titer gamma globulin was recently developed, which is approved in the United States of its use for preventing the onset of HCMV infection associated with kidney transplantation. However, since an anti-CMV high-titer gamma globulin formulation is a human-derived blood preparation, it has various problems. For example, a mixture of human-derived gamma globulin results in significant lot-to-lot variation in the activity, low activity and limited supply, as well as constant risks such as contamination of unknown pathogenic virus or pathogen.

Accordingly, since a monoclonal antibody (hereinafter, sometimes referred to as an "anti-HCMV antibody") that binds to HCMV and neutralizes the infectivity thereof (i.e., annihilating the biological activity thereof) can be expected as a prophylactic or therapeutic drug for various pathological conditions caused by HCMV, it is useful, for example, in terms of prevention or treatment strategy against various diseases caused by HCMV in a patient with an immunodeficiency condition.

Specifically, a human-derived anti-HCMV antibody that has strong affinity and high neutralizing capacity against HCMV to annihilate HCMV activity to prevent the onset of the diseases or alleviate the symptoms and that cause no allergic reaction appeared to be effective to be administered as a so-called "antibody drug".

However, HCMV-inhibiting antibodies reported so far (for example, Patent Documents 1, 2, 3, 4 and 5) were insufficient in terms of affinity, neutralizing capacity and the like against HCMV, and thus they were short of being expected to sufficiently block HCMV bioactivities to prevent onset of various diseases caused by HCMV or to alleviate symptoms thereof.

Therefore, development of an anti-HCMV antibody or an antigen-binding fragment thereof, which is a human monoclonal antibody that does not recognize or respond to a foreign substance, that has excellent affinity, specificity and neutralizing capacity for HCMV, and that can be expected of its use as a prophylactic or therapeutic drug, has been strongly desired.

Lately, in order to suppress HCMV proliferation in vivo, not only the neutralizing activity but also the importance of blocking cell-to-cell infection has been mentioned (Non-Patent Documents 12 and 13), and thus an anti-HCMV antibody that also has an activity to inhibit cell-to-cell infection has been much needed.

PRIOR ART DOCUMENTS

Patent Documents

Patent Document 1: Japanese Patent Application Publication No. 8-502403
Patent Document 2: Japanese Patent Application Publication No. 8-506325
Patent Document 3: WO87/03602
Patent Document 4: WO93/021952
Patent Document 5: WO2007/094423

Non-Patent Documents

Non-Patent Document 1: Davison, A. J. et al., The human cytomegalovirus genome revisited: comparison with the chimpanzee cytomegalovirus genome. J. Gen. Virol., 2003; 84: p 17-28
Non-Patent Document 2: Dolan, A. et al., Genetic content of wild-type human cytomegalovirus. J. Gen. Virol., 2004; 85: p 1301-1312
Non-Patent Document 3: Keiko TAYA, Discussion of Infection: Cytomegalovirus infection, Infectious Diseases Weekly Report Japan. 2003; Week 15:10-14
Non-Patent Document 4: Griffiths, P. D., The treatment of cytomegalovirus infection. J. Anti. Chemo., 2002; 49: p 243-253
Non-Patent Document 5: Demmler, G. J., Congenital cytomegalovirus infection and disease. Seminars in Pediatric Infection Diseases. Seminars in Pediatric Infectious Diseases, 1999; 10: p 195-200
Non-Patent Document 6: Freitas, V. R. et al., Activity of 9-(1,3-dihydroxy-2-Propoxymethel)guanine compared with that of acyclovir against human, monkey, and rodent cytomegaloviruses. Anti. Agent Chemo., 1985; 28: p 240-245
Non-Patent Document 7: Package insert for anti-cytomegalovirus chemotherapeutic agent, Denosine for intravenous infusion, 500 mg, ganciclovir formulation, Mitsubishi Tanabe Pharma (revised in October, 2007)
Non-Patent Document 8: Package insert for antiviral agent for drip injection, Foscavir, 24 mg/mL, foscarnet sodium hydrate injection, AstraZeneca (revised in June, 2007)
Non-Patent Document 9: Package insert for anti-cytomegalovirus chemotherapeutic agent, Valixa tablet (4500 mg), valganciclovir hydrochloride formulation, Mitsubishi Tanabe Pharma (revised in October, 2007)
Non-Patent Document 10: Kimberlin, D. W. et al., Effect of ganciclovir therapy on hearing in symptomatic congenital cytomegalovirus disease involving the central nervous system; randomized, controlled trial. J. Pediatr., 2003; 143: 16-25
Non-Patent Document 11: Masuho, T., et al., Human monoclonal antibodies neutralizing human cytomegalovirus. J. Gen. Virol, 1987; 68: p 1457-1461
Non-Patent Document 12: Navarro, D. et al., Glycoprotein B of human cytomegalovirus promotes virion penetration into cells, transmission of infection from cell to cell, and fusion of infected cells. Virology, 1993; 197: p 143-158
Non-Patent Document 13: Ohizumi, Y., Neutralizing mechanism of two human monoclonal antibodies against human cytomegalovirus glycoprotein 130/55. J. Gen. Virol., 1992; 73: p 2705-2707

SUMMARY OF THE INVENTION

Problems to be Solved by the Invention

Thus, an antibody or an antigen-binding fragment that specifically binds to HCMV and that sufficiently inhibits the bioactivity thereof appears to be useful against various diseases caused by HCMV from a treatment or prevention strategy perspective.

At the moment, most of the antibody drugs that are approved as pharmaceutical products need to be administered in a large amount of several mg to several hundreds of mg per day and are expensive. Many of the biopharmaceutical products that are commercially available so far other than antibody pharmaceutical products need to be administered several-tens μg to 1 mg per day. In comparison, daily dosages of antibody pharmaceutical products greatly vary from approximately 10 to 1000 times the conventional biopharmaceutical product. HCMV leads to various disease conditions, and treatments of these diseases have important issues such as higher activity, less therapeutic dose and keeping the treatment cost low, considering the possible effect on newborn, infant and a pregnant woman. In other words, not any antibody drug but one with high bioactivity is desired, which is more useful with more excellent affinity and higher neutralizing capacity as a pharmaceutical product in terms of healthcare expenditure.

Although the amount of production of the antibody pharmaceutical products needed is greatly increasing, production facilities are insufficient on a global basis. Under such circumstances, a human anti-HCMV monoclonal antibody with higher affinity and neutralizing capacity is desired since an antibody with excellent affinity and neutralizing capacity can exert effects with less amount. What's more, since HCMV is fundamentally infective for broad types of tissues and cells in bodies (Sinzger, C. et al., Curr Top Microbiol Immunol., 2008; 325: p 63-83), it is important for the anti-HCMV antibody to exert clinical effects to have an effective neutralizing activity for any of fibroblast cell, epithelial cell and endothelial cell as a host cell to be infected.

Given the spreading manner of HCMV infection in vivo, an anti-HCMV antibody that not only has neutralizing capacity but also has blocking capacity of cell-to-cell infection is much needed. Moreover, in view of effectivity and safety as a pharmaceutical product, provision of a pharmaceutical composition comprising a human-derived monoclonal antibody or an antigen-binding fragment thereof that has high neutralizing capacity and cell-to-cell infection blocking capacity against HCMV that causes various disease states is desired.

Means for Solving the Problems

In order to acquire the above-described antibody, the present inventors have conducted keen studies and succeeded with ingenuity in obtaining a human monoclonal antibody that specifically recognizes a previously unreported discontinuous epitope present on the AD1 region of the HCMV glycoprotein gB, that also has high neutralizing capacity and high cell-to-cell infection blocking capacity, thereby accomplishing the present invention.

Thus, the present invention relates to an anti-HCMV monoclonal antibody or a binding fragment thereof, DNA (polynucleotide) coding for the antibody or the binding fragment, a vector containing the DNA, and a host cell containing the vector described below.

[1] An antibody or an antigen-binding fragment thereof that binds to the AD1 region of human cytomegalovirus (HCMV) glycoprotein gB, and that recognizes, as an epitope, a discontinuous sequence comprising the amino acid sequence of SEQ ID NO:25, the amino acid sequence of SEQ ID NO:26 and the amino acid sequence of SEQ ID NO:27 present in the AD1 region.

[2] A monoclonal antibody that specifically binds to the AD1 region of human cytomegalovirus (HCMV) glycoprotein gB and that is capable of neutralizing the bioactivity thereof, wherein
(i) the variable region of the heavy chain comprises:
(a) an amino acid sequence of heavy chain CDR1 selected from the group consisting of the amino acid sequence of SEQ ID NO:13 and an amino acid sequence having deletion, substitution, insertion, addition or a combination of two or more of these mutations for one to several amino acid residues in the amino acid sequence of SEQ ID NO:13;
(b) an amino acid sequence of heavy chain CDR2 selected from the group consisting of the amino acid sequence of SEQ ID NO:14 and an amino acid sequence having deletion, substitution, insertion, addition or a combination of two or more of these mutations for one to several amino acid residues in the amino acid sequence of SEQ ID NO:14; and
(c) an amino acid sequence of heavy chain CDR3 selected from the group consisting of the amino acid sequence of SEQ ID NO:15, an amino acid sequence having deletion, substitution, insertion, addition or a combination of two or more of these mutations for one to several amino acid residues in the amino acid sequence of SEQ ID NO:15, and the amino acid sequence of SEQ ID NO:22, and
(ii) the variable region of the light chain comprises:
(a) an amino acid sequence of light chain CDR1 selected from the group consisting of the amino acid sequence of SEQ ID NO:16 and an amino acid sequence having deletion, substitution, insertion, addition or a combination of two or more of these mutations for one to several amino acid residues in the amino acid sequence of SEQ ID NO:16;
(b) an amino acid sequence of light chain CDR2 selected from the group consisting of the amino acid sequence of SEQ ID NO:17 and an amino acid sequence having deletion, substitution, insertion, addition or a combination of two or more of these mutations for one to several amino acid residues in the amino acid sequence of SEQ ID NO:17; and
(c) an amino acid sequence of light chain CDR3 selected from the group consisting of the amino acid sequence of SEQ ID NO:18 and an amino acid sequence having deletion, substitution, insertion, addition or a combination of two or more of these mutations for one to several amino acid residues in the amino acid sequence of SEQ ID NO:18, or an antigen-binding fragment thereof.

[3] The antibody or the antigen-binding fragment thereof according to [2] above, which specifically binds to an epitope comprising two or more discontinuous sequences present in regions of an amino acid sequence (SEQ ID NO:23) consisting of the continuous amino acid residues at positions 549-580 and an amino acid sequence (SEQ ID NO:24) consisting of the continuous amino acid residues at positions 596-640 of HCMV-glycoprotein gB.

[4] The antibody or the antigen-binding fragment thereof according to [2] above, which recognizes, as an epitope, a discontinuous sequence comprising the amino acid sequence of SEQ ID NO:25, the amino acid sequence of SEQ ID NO:26 and the amino acid sequence of SEQ ID NO:27 in the AD1 region of HCMV-glycoprotein gB.

[5] The antibody or the antigen-binding fragment thereof according to either one of [3] and [4] above, the antibody comprising:
(i)
(a) an amino acid sequence of heavy chain CDR1 comprising the amino acid sequence of SEQ ID NO:13

(b) an amino acid sequence of heavy chain CDR2 comprising the amino acid sequence of SEQ ID NO:14; and
(c) an amino acid sequence of heavy chain CDR3 comprising the amino acid sequence of SEQ ID NO:22, and
(ii)
(a) an amino acid sequence of light chain CDR1 comprising the amino acid sequence of SEQ ID NO:16
(b) an amino acid sequence of light chain CDR2 comprising the amino acid sequence of SEQ ID NO:17; and
(c) an amino acid sequence of light chain CDR3 comprising the amino acid sequence of SEQ ID NO:18.

[6] The antibody or the antigen-binding fragment thereof according to [5] above, the antibody comprising:
(i)
(a) an amino acid sequence of heavy chain CDR1 comprising the amino acid sequence of SEQ ID NO:13
(b) an amino acid sequence of heavy chain CDR2 comprising the amino acid sequence of SEQ ID NO:14; and
(c) an amino acid sequence of heavy chain CDR3 comprising the amino acid sequence of SEQ ID NO:15, and
(ii)
(a) an amino acid sequence of light chain CDR1 comprising the amino acid sequence of SEQ ID NO:16
(b) an amino acid sequence of light chain CDR2 comprising the amino acid sequence of SEQ ID NO:17; and
(c) an amino acid sequence of light chain CDR3 comprising the amino acid sequence of SEQ ID NO:18.

[7] The antibody or the antigen-binding fragment thereof according to [2] above, comprising:
(a) a heavy chain variable region (HCVR) consisting of the amino acid sequence of SEQ ID NO:10, an amino acid sequence having deletion, substitution, insertion, addition or a combination of two or more of these mutations for one to several amino acid residues in the amino acid sequence of SEQ ID NO:10, or an amino acid sequence having an identity of 95% or more with the amino acid sequence of SEQ ID NO:10; and
(b) a light chain variable region (LCVR) consisting of the amino acid sequence of SEQ ID NO:12, an amino acid sequence having deletion, substitution, insertion, addition or a combination of two or more of these mutations for one to several amino acid residues in the amino acid sequence of SEQ ID NO:12, or an amino acid sequence having an identity of 95% or more with the amino acid sequence of SEQ ID NO:12.

[8] The antibody or the antigen-binding fragment thereof according to [7] above, comprising:
(a) a heavy chain variable region (HCVR) comprising the amino acid sequence of SEQ ID NO:10; and
(b) a light chain variable region (LCVR) comprising the amino acid sequence of SEQ ID NO:12.

[9] The antibody or the antigen-binding fragment thereof according to [2] above, comprising:
(a) a heavy chain (H-chain) having the amino acid sequence of SEQ ID NO:2 or 6, an amino acid sequence having deletion, substitution, insertion, addition or a combination of two or more of these mutations for one to several amino acid residues in the amino acid sequence of SEQ ID NO:2 or 6, or an amino acid sequence having an identity of 95% or more with the amino acid sequence of SEQ ID NO:2 or 6; and
(b) a light chain (L-chain) having the amino acid sequence of SEQ ID NO:4 or 8, an amino acid sequence having deletion, substitution, insertion, addition or a combination of two or more of these mutations for one to several amino acid residues in the amino acid sequence of SEQ ID NO:4 or 8, or an amino acid sequence having an identity of 95% or more with the amino acid sequence of SEQ ID NO:4 or 8.

[10] The antibody or the antigen-binding fragment thereof according to [9] above, comprising:
(a) a heavy chain (H-chain) comprising the amino acid sequence of SEQ ID NO:2 or 6; and
(b) a light chain (L-chain) comprising the amino acid sequence of SEQ ID NO:4 or 8.

[11] The antibody or the antigen-binding fragment according to any one of [1]-[10] above, wherein the antibody is a human monoclonal antibody.

[12] The antibody or the antigen-binding fragment according to any one of [1]-[11] above, wherein the class (subclass) of the antibody is IgG1 (λ).

[13] The antibody or the antigen-binding fragment according to any one of [1]-[12] above, whose 50% inhibitory concentration for plaque formation is 0.05 μg/mL (approximately 0.3 nM) or less for HCMV laboratory strain (AD169) in the presence of a human fibroblast cell.

[14] The antibody or the antigen-binding fragment according to any one of [1]-[13] above, which has cell-to-cell infection blocking capacity of 50% or higher at 0.2 μg/mL (approximately 1.3 nM) or less in a human fibroblast cell line (MRC-5) infected with HCMV laboratory strain (AD169).

[15] A pharmaceutical composition for preventing or treating a human cytomegalovirus (HCMV)-related disease, comprising the antibody or the antigen-binding fragment according to any one of [1]-[14] above and a pharmaceutically acceptable carrier.

[16] The pharmaceutical composition according to [15] above, wherein the HCMV-related disease is (a) interstitial pneumonia, retinitis, gastroenteritis or encephalitis caused by reactivation of HCMV in an immunodeficiency state, (b) congenital CMV infection due to transmission of HCMV infection from a pregnant woman to a fetus, (c) miscarriage, stillbirth or death shortly after birth caused by the above-described congenital CMV infection, (d) low birth weight, hepatosplenomegaly, jaundice, thrombocytopenic purpura, microcephaly, disorder of mental development, delay of intellectual development, chorioretinitis or hearing impairment in the case of survival through the above-described congenital CMV infection; or (e) abnormality of hepatic function, interstitial pneumonia or mononucleosis that is caused by HCMV infection during newborn or infancy.

[17] A nucleic acid coding for an anti-HCMV monoclonal antibody or an antigen-binding fragment thereof that specifically binds to the AD1 region of HCMV glycoprotein gB and that is capable of neutralizing the bioactivity thereof, wherein the isolated nucleic acid is selected from nucleic acids coding for amino acid sequences selected from the group consisting of SEQ ID NOS:2, 4, 6, 8, 10, 12, 13-18 and 22, and nucleic acids that hybridize therewith under highly stringent conditions.

[18] A vector incorporating a nucleic acid according to [17] above.

[19] A host cell incorporating the vector according to [18] above.

[20] A method for producing the antibody or the antigen-binding fragment according to any one of [1]-[14] above, comprising a step of culturing the host cell according to [19] above.

Effects of the Invention

An anti-HCMV antibody of the present invention, in particular, an antibody that specifically binds to AD1 region of HCMV-glycoprotein gB, or an antigen-binding fragment thereof can specifically bind to HCMV that is causative of various diseases, for example, in an immunodeficiency state, and annihilate (neutralize) the bioactivity of HCMV, thereby exerting excellent neutralizing capacity against HCMV. In addition, an embodiment where the anti-HCMV-glycoprotein gB AD1 antibody of the present invention is a human monoclonal antibody is advantageous in that it has no immunogenicity and in that it produces no immune response.

One embodiment of the anti-HCMV antibody of the present invention has high cell-to-cell infection blocking capacity or cell-to-cell infection inhibitory activity against HCMV. In view of the mode of HCMV infection spread in vivo, it is advantageous that the anti-HCMV antibody not only has neutralizing capacity but also has cell-to-cell infection blocking capacity.

An anti-HCMV antibody or an antigen-binding fragment thereof of the present invention has high neutralizing capacity and infection spread inhibitory activity against HCMV. Since a human monoclonal antibody has no immunogenicity, it is likely to be useful as a prophylactic or therapeutic drug for various diseases caused by HCMV, for example: (a) diseases such as interstitial pneumonia, retinitis, gastroenteritis, encephalitis and the like due to HCMV reactivation in immunodeficiency states such as AIDS, cancer, after organ transplantation, after bone-marrow transplantation, and after hemodialysis; (b) congenital CMV infection due to transmission of HCMV infection from a pregnant woman to a fetus; (c) miscarriage, stillbirth and death shortly after birth caused by the above-described congenital CMV infection; (d) low birth weight, hepatosplenomegaly, jaundice, thrombocytopenic purpura, microcephaly, disorder of mental development, delay of intellectual development, chorioretinitis and hearing impairment in the case of survival through the above-described congenital CMV infection; and (e) abnormality of hepatic function, interstitial pneumonia and mononucleosis due to HCMV infection during newborn or infancy (Non-Patent Documents 3, 4 and 5).

Furthermore, a pharmaceutical composition containing a particularly preferable human monoclonal antibody of the present invention is effective with an extremely small amount.

Lately, studies for an anti-HCMV antibody have been conducted against various surface antigens other than glycoprotein gB, for example, gH, gL or the like. However, given the circumstances mentioned in (1)-(3) below, an antibody that specifically binds to glycoprotein gB, particularly AD1 region thereof, and having high neutralizing activity, like the antibody of the present invention, is highly useful as a prophylactic or therapeutic drug for HCMV infection.

(1) In order to suppress viral proliferation such as HCMV in vivo, importance of not only neutralizing activity but also blocking of cell-to-cell infection has been pointed out (Non-Patent Documents 12 and 13). Meanwhile, recent glycoprotein gB studies shows that gB plays an important role in the entry of viral particles into cells and the cell-to-cell infection (Isaacson, M. K. et al., Human cytomegalovirus glycoprotein B is required for virus entry and cell-to-cell spread but not for virion attachment, assembly, or egress. J. Virology, 2009; 83: p 3891-3903). Hence, an antibody against gB is very likely to also contribute to inhibition of cell-to-cell infection.

(2) Among the glycoprotein gB essential for HCMV infection, AD1 region is requisite for functions and formation of conformation of gB (Qadri, I. et al., Assembly of conformational-dependent neutralizing domains on glycoprotein B of human cytomegalovirus. J. Gen. Virol, 1992; 73; p 2913-2921; and Britt, W. J. et al., Antigenic domain is required for oligomerization of human cytomegalovirus glycoprotein B. J. Virol., 2005; 79: p 4066-4079), and it is also known as a part with less mutation of a clinically isolated virus strain. Thus, an antibody against AD1 possibly has a broad spectrum.

(3) An AD1 antibody that recognizes discontinuous epitopes throughout a longer region on gB as compared to an antibody against AD2 region, has higher specificity and thus seems to have less possibility in causing unexpected side effects by cross reactivity with other biological molecule.

BRIEF DESCRIPTION OF THE DRAWINGS

FIG. 3 shows evaluation of the capacities of the sequence to bind to AD1, when subjected to conservative amino acid substitutions at positions 121, 123, 124 and 126 of EV2038 H-chain.

FIG. 4 shows evaluation of the capacities of the sequence to bind to AD1 when proline at position 125 of EV2038 H-chain is substituted with all of the amino acids other than proline and arginine.

FIG. 5 shows evaluation of the capacities of the sequence to bind to AD1 when subjected to conservative amino acid substitutions of the amino acid residues among the amino acids forming EV2038 CDR-H3 whose binding capacities to AD1 did not decrease when subjected to the nonconservative amino acid substitutions shown in FIG. 2.

FIG. 6 shows evaluation of the binding capacities of variants to AD1. A total of four types of variants were prepared by simultaneously substituting two or four of the amino acid residues that showed reduced binding capacities to AD1 upon nonconservative amino acid substitutions among the amino acids forming EV2038 CDR-H3 other than proline at position 125 (namely, total of four residues at positions 121, 123, 124 and 126) (two-amino-acid-substituted products: I124V/G126A and I124V/G126S, four-amino-acid-substituted products: L121I/W123Y/I124V/G126A and L121I/W123Y/I124V/G126S).

FIG. 7 shows evaluation of binding capacities of variants to AD1. One each of deletion and insertion variants (E122del and G126_D127insE) for the amino acid residues at positions 121, 123, 124 and 126 (proline at position 125 was excluded), i.e., four residues in total, in the amino acids forming EV2038 CDR-H3, the non-conservative amino acid substitution which showed reduced binding capacities to AD1, was prepared and subjected to the evaluation.

FIG. 8 shows evaluation of binding capacity to AD1 of a variant having mutation at 79th amino acid residue of EV2038 CDR-H2 region.

FIG. 9(A) shows a view of clones of glycoprotein gB AD1 region-deleted mutants used for analyzing epitope regions, while FIG. 9(B) is a view showing results from Western blot analysis using these deletion mutants.

FIG. 10(A) shows results from epitope mapping of EV2038 using a peptide array. FIG. 10(B) shows the above-mentioned results from the analysis along with the amino acid sequence of glycoprotein gB, as well as results of an analysis using deletion mutant of EV2038 and previously reported epitope sequence of ITC52. The SEQ ID NOs corresponding to the sequences appearing in FIG. 10(B) are listed in Table 5.

FIG. 11(A) is a graph showing the neutralizing activities of a human monoclonal antibody (hIgG) as a negative control that has no specificity to HCMV and EV2001 as an anti-AD1 antibody (disclosed in Patent Document 5), against human cytomegalovirus (AD169 strain) in the presence of a complement; FIG. 11(B) is a graph showing the neutralizing activities of hIgG and anti-HCVM monoclonal antibodies (EV2038 and HCMV16), against human cytomegalovirus (AD169 strain) in the presence of a complement; FIG. 11(C) is a graph showing the neutralizing activities of hIgG as a negative control and EV2001, against human cytomegalovirus (AD169 strain) in the absence of a complement; and FIG. 11(D) shows the neutralizing activities of hIgG and anti-HCMV monoclonal antibodies (EV2038 and HCMV16), against human cytomegalovirus (AD169 strain) in the absence of a complement.

EMBODIMENT FOR CARRYING OUT THE INVENTION

Figures 1, 2:
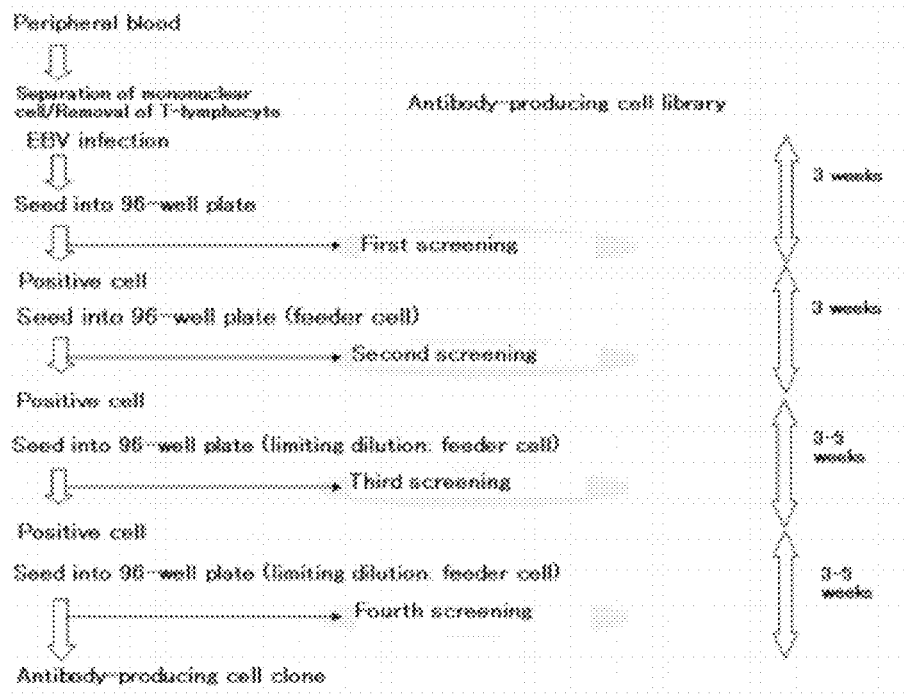
FIG. 1 is a flowchart showing a procedure for separating an antibody-producing cell clone for producing an anti-HCMV antibody according to the present invention.
FIG. 2 shows evaluation of the capacities of sequences of 16 amino acid residues forming EV2038 CDR-H3 to bind to AD1, when subjected to nonconservative amino-acid substitutions.

1. Antibody or Antigen-Binding Fragment thereof According to the Present Invention According to one embodiment of the present invention, an antibody or an antigen-binding fragment thereof that specifically binds to glycoprotein gB of human cytomegalovirus (HCMV) and that is capable of neutralizing the bioactivity thereof is provided. According to a more specific embodiment, an antibody or an antigen-binding fragment thereof that specifically binds to a discontinuous epitope present in the AD1 region of HCMV glycoprotein gB and that is capable of neutralizing the bioactivity of the protein is provided.

"Glycoprotein gB of human cytomegalovirus (HCMV)" (or "HCMV glycoprotein gB" or "HCMV-glycoprotein gB") is one of the major glycoproteins that form the envelope of HCMV, which is known to contribute to the entry of viral particles into cells, cell fusion and the cell-to-cell infection by a virus. The amino acid sequence of HCMV glycoprotein gB (amino acid sequence of AD169 strain as a representative strain of HCMV virus) is available as the amino acid sequence (SEQ ID NO:137) of the protein of Accession No: P06473 from a sequence database available to the public (Swiss-Prot).

"AD1 region of glycoprotein gB of human cytomegalovirus (HCMV)" or "HCMV glycoprotein gBAD1 region" refers to a region consisting of continuous amino acid residues at positions 552-635 of the amino acid sequence of HCMV glycoprotein gB (Wagner et al., Journal of Virology, Vol. 66, No. 9, September 1992, p. 5290-5297).

Herein, the term "epitope" is used in a general meaning in the art field and refers to a small partial structure of an antigen molecule as a binding partner of an antibody (Iwanami Biological Dictionary, 4th Ed. (1st Ed. published in 1996)).

According to a still more specific embodiment of the invention, a discontinuous epitope present in the AD1 region exists in the amino acid sequence of continuous amino acid residues at positions 549-580 (SEQ ID NO:23) and the amino acid sequence of continuous amino acid residues at positions 596-640 (SEQ ID NO:24) of human cytomegalovirus (HCMV) glycoprotein gB. Yet more specifically, the discontinuous epitope consists of the amino acid sequence of SEQ ID NO:25, the amino acid sequence of SEQ ID NO: 26 and the amino acid sequence of SEQ ID NO: 27.

According to one embodiment, an antibody or an antigen-binding fragment thereof the present invention includes:

(a) a heavy chain (H-chain) containing the amino acid sequence of SEQ ID NO:2 or 6; and
(b) a light chain (L-chain) containing the amino acid sequence of SEQ ID NO:4 or 8, where the antibody or the antigen-binding fragment specifically binds to glycoprotein gB of human cytomegalovirus and is capable of neutralizing the bioactivity thereof.

Alternatively, an antibody or an antigen-binding fragment thereof of the present invention includes:

(a) a heavy chain variable region (HCVR) containing the amino acid sequence of SEQ ID NO:10; and
(b) a light chain variable region (LCVR) containing the amino acid sequence of SEQ ID NO:12, where it specifically binds to glycoprotein gB of human cytomegalovirus and is capable of neutralizing the bioactivity thereof.

Alternatively, an antibody or an antigen-binding fragment of the present invention specifically binds to glycoprotein gB of human cytomegalovirus and is capable of neutralizing the bioactivity thereof, where (i) the amino acid sequences of CDR (Complementarity Determining Region) 1, CDR2 and CDR3 of the variable region of the heavy chain includes:
(a) the amino acid sequence of SEQ ID NO:13;
(b) the amino acid sequence of SEQ ID NO:14; and
(c) the amino acid sequence of SEQ ID NO:15, respectively, and
(ii) the amino acid sequences of CDR1, CDR2 and CDR3 of the variable region of the light chain includes:
(a) the amino acid sequence of SEQ ID NO:16;
(b) the amino acid sequence of SEQ ID NO:17; and
(c) the amino acid sequence of SEQ ID NO:18, respectively.

An antibody or an antigen-binding fragment thereof also comprises a functional equivalent of the above-described antibody or antigen-binding fragment, which specifically binds to glycoprotein gB of human cytomegalovirus and is capable of neutralizing the bioactivity thereof. These include, for example:

(a) a heavy chain (H-chain) shown by an amino acid sequence having deletion, substitution, insertion, addition or a combination of two of more of any of these mutations for one to several amino acid residues in the amino acid sequence of SEQ ID NO:2 or 6, or an amino acid sequence having an identity of 95% or more with the amino acid sequence of SEQ ID NO:2 or 6; and
(b) a light chain (L-chain) shown by an amino acid sequence having deletion, substitution, insertion, addition or a combination of two of more of any of these mutations for one to several amino acid residues in the amino acid sequence of SEQ ID NO:4 or 8, or an amino acid sequence having an identity of 95% or more with the amino acid sequence of SEQ ID NO:4 or 8.

Alternatively, a functional equivalent of the above-described antibody or antigen-binding fragment also include:

(a) a heavy chain variable region (HCVR) comprising an amino acid sequence having deletion, substitution, insertion, addition or a combination of two of more of any of these mutations for one to several amino acid residues in the amino acid sequence of SEQ ID NO:10, or an amino acid sequence having an identity of 95% or more with the amino acid sequence of SEQ ID NO:10; and
(b) a light chain variable region (LCVR) comprising an amino acid sequence having deletion, substitution, insertion, addition or a combination of two of more of any of these mutations for one to several amino acid residues in the amino acid sequence of SEQ ID NO:12, or an amino acid sequence having an identity of 95% or more with the amino acid sequence of SEQ ID NO:12.

Alternatively, a functional equivalent of the above-described antibody or antigen-binding fragment further includes:

(i)
(a) heavy chain CDR1 selected from the group consisting of amino acid sequences having deletion, substitution, insertion, addition or a combination of two of more of any of these mutations for one to several amino acid residues in the amino acid sequence of SEQ ID NO:13,
(b) heavy chain CDR2 selected from the group consisting of amino acid sequences having deletion, substitution, insertion, addition or a combination of two of more of any of these mutations for one to several amino acid residues in the amino acid sequence of SEQ ID NO:14, and
(c) heavy chain CDR3 selected from the group consisting of amino acid sequences having deletion, substitution, insertion, addition or a combination of two of more of any of these mutations for one to several amino acid residues in the amino acid sequence of SEQ ID NO:15 and the amino acid sequence of SEQ ID NO:22; and (ii)
(a) light chain CDR1 selected from the group consisting of amino acid sequences having deletion, substitution, insertion, addition or a combination of two of more of any of these mutations for one to several amino acid residues in the amino acid sequence of SEQ ID NO:16,
(b) light chain CDR2 selected from the group consisting of amino acid sequences having deletion, substitution, insertion, addition or a combination of two of more of any of these mutations for one to several amino acid residues in the amino acid sequence of SEQ ID NO:17, and
(c) light chain CDR3 selected from the group consisting of amino acid sequences having deletion, substitution, insertion, addition or a combination of two of more of any of these mutations for one to several amino acid residues in the amino acid sequence of SEQ ID NO:18.

The upper limit of the number of mutations contained in the amino acid sequence of the above-described functional equivalent may be determined based on whether the equivalent can specifically bind to glycoprotein gB of HCMV and is capable of neutralizing the bioactivity thereof. The neutralizing activity of HCMV may be evaluated, for example, according to methods described in Examples 9 and 10 below. The capacity for blocking cell-to-cell infection can be evaluated according to a method described in Example 11 below.

The term "antibody" as used herein refers to an immunoglobulin molecule consisting of four polypeptide chains, that is, two heavy (H) chains and two light (L) chains, which are mutually connected via disulfide bonds. A monoclonal antibody according to the present invention also consists of an immunoglobulin molecule containing two each of light chains (L-chains) and heavy chains (H-chains). Each of the H-chains consists of a H-chain variable region (sometimes referred to as "HCVR" or "$V_H$") and a H-chain constant region (H-chain constant region consists of three domains, which may sometimes be referred to as "$C_H1$", "$C_H2$" and "$C_H3$" (collectively called $C_H$)). Each of the L-chain consists of a L-chain variable region (sometimes referred to as "LCVR" or "$V_L$") and a L-chain constant region (L-chain constant region consists of a single domain, which may sometimes be referred to as "$C_L$").

In particular, HCVR and LCVR are important in that they are responsible for the binding specificity of an antibody. Since an antibody interacts with a target antigen chiefly via the amino acid residues of LCVR and HCVR, the amino acid sequence within the variable region greatly varies among various antibodies than the sequence outside the variable region. HCVR and LCVR can further be classified into a region called framework region (FR) and a hypervariable region called complemetarity determining region (CDR), which are more constant among various antibodies. HCVR and LCVR each consist of three CDRs and four FRs, which are sequentially aligned in the order of FR1, CDR1, FR2, CDR2, FR3, CDR3 and FR4 from the amino terminus to the carboxy terminus.

The term "antigen-binding fragment" (or simply "antibody fragment") of an antibody refers to a fragment of one or more antibodies capable of specifically binding to an antigen (for example, HCMV). In this case, this fragment should contain a peptide having a minimum amino acid sequence that specifically binds to the antigen. In addition, a single-stranded antibody (scFV), a bispecific antigen, a polyspecific antigen and the like having the variable region or the complemetarity determining region of the antibody that specifically bind to the antigen are also included in the "antigen-binding fragments". Herein, for the sake of simplicity, "an antibody or an antigen-binding fragment" may be simply referred to as an "antibody".

An "antibody capable of neutralizing bioactivity of HCMV" refers to an antibody that inhibits bioactivity of HCMV by binding to HCMV or a HCMV-infected cell.

Typical "bioactivity of HCMV" includes, but not limited to, activities of HCMV that cause the following diseases (a)-(e) exemplified below, and include HCMV activities that induce various diseases caused by the action of the activated HCMV:

(a) various diseases such as interstitial pneumonia, retinitis, gastroenteritis or encephalitis caused by reactivation of HCMV in an immunodeficiency state such as AIDS, cancer, after organ transplantation, after bone-marrow transplantation or after hemodialysis;
(b) congenital CMV infection due to transmission of HCMV infection from a pregnant woman to a fetus;
(c) miscarriage, stillbirth or death shortly after birth caused by the above-described congenital CMV infection;
(d) low birth weight, hepatosplenomegaly, jaundice, thrombocytopenic purpura, microcephaly, disorder of mental development, delay of intellectual development, chorioretinitis or hearing impairment in the case of survival through the above-described congenital CMV infection; or
(e) abnormality of hepatic function, interstitial pneumonia or mononucleosis that is caused due to HCMV infection during newborn or infancy (Non-Patent Documents 3, 4 and 5).

The term "disease caused by HCMV" as used herein include, as well as other diseases, a disease that is found to be or that appears to be caused because a target subject suffering from that disease has HCMV as the cause of the pathological conditions of that disease or as a cause of worsening that disease. Therefore, diseases caused by bioactivity of HCMV are those whose symptoms and/or progression are expected to be alleviated by inhibition of HCMV bioactivity. Symptoms of such diseases may be alleviated or treated, for example, by using the above-described anti-HCMV antibody. Specifically, the above-mentioned disease may be proven by increasing the anti-HCMV antibody level in the biological fluid of the target subject suffering from that disease (for example, by increasing the anti-HCMV antibody level in the serum, plasma or synovial fluid of the target subject).

The terms such as "inhibitory effect", "inhibition", "suppression" and "capable of inhibiting" as used herein refer to reducing the bioactivity resulting from the antigen (HCMV)

by approximately 5-100%, preferably 10-100%, more preferably 20-100%, more preferably 30-100%, more preferably 40-100%, more preferably 50-100%, more preferably 60-100%, more preferably 70-100% and still more preferably 80-100%.

Since the amino acid sequence of the variable region is responsible for most of the antibody-antigen interaction, a recombinant antibody replicating a property of a particular naturally-occurring antibody can be expressed by constructing an expression vector that contains a sequence of the variable region or a sequence of the CDR moiety derived from the particular naturally-occurring antibody, grafted to a constant region or a framework sequence derived from a different antibody having a different property.

Accordingly, in order to remake an intact recombinant antibody having the same binding characteristic as that of the original antibody, there is no need to obtain the entire sequence of the particular antibody. The sequence of the variable region or the CDR moiety of the heavy and light chains of the antibody may be sufficient for this purpose.

SEQ ID NOS:13, 14 and 15 represent amino acid sequences corresponding to CDR1, CDR2 and CDR3 of the heavy chain, respectively. SEQ ID NOS:16, 17 and 18 are amino acid sequences corresponding to CDR1, CDR2 and CDR3 of the light chain, respectively. Therefore, a preferable antibody of the present invention has CDR1, CDR2 and CDR3 of the heavy chain and CDR1, CDR2 and CDR3 of the light chain corresponding to SEQ ID NOS:13, 14, 15, 16, 17 and 18, respectively. However, CDR1, CDR2 and CDR3 of the heavy chain and CDR1, CDR2 and CDR3 of the light chain may not necessarily correspond to SEQ ID NOS:13, 14, 15, 16, 17 and 18, respectively, as long as the monoclonal antibody specifically binds to HCMV and is capable of neutralizing the bioactivity thereof. CDR-3 of the heavy chain, in particular, may be an amino acid sequence selected from the amino acid sequence group of SEQ ID NO:22. Moreover, the CDR sequence may be an amino acid sequence having deletion, substitution, insertion, addition or a combination of two or more of these mutations for one to several (specifically, 1-9, 1-8, 1-7, 1-6, 1-5, 1-4, 1-3, 1-2 or 1) amino acid residues in an amino acid sequence selected from the group consisting of the amino acid sequences of SEQ ID NOS:13, 14, 15, 16, 17 and 18, as long as it has the above-described neutralizing activity.

The amino acid sequence other than CDR is not particularly limited, and a so-called CDR grafting antibody in which the amino acid sequence other than CDR is derived from other antibody, in particular, an antibody of other species, is also encompassed by the present invention. The amino acid sequence other than CDR is preferably a human-derived antibody, but if necessary, the framework region (FR) may include deletion, substitution, insertion, addition or a combination of two or more of these mutations for one to several (specific number being the same as mentioned above) amino acid residues. Such antibodies may be prepared according to a known method (Riechmann L, et al., Reshaping human antibodies for therapy. Nature, 332:323-327, 1988). According to the present invention, a complete human antibody, of course, is favorable.

Deletion, substitution, insertion, addition or a combination of two or more of these mutations for one or more amino acid residues in an amino acid sequence of a protein of the present invention means that deletion, substitution, insertion and addition of one or several amino acid residues are present at any one or more positions of the same amino acid sequence, where two or more of the deletion, substitution, insertion and addition may occur simultaneously.

Amino acids forming naturally-occurring proteins can be classified according to the properties of their side chains. For example, examples of amino acid groups having similar properties include aromatic amino acids (tyrosine, phenylalanine, tryptophan), basic amino acids (lysine, arginine, histidine), acidic amino acids (aspartic acid, glutamic acid), neutral amino acids (serine, threonine, asparagine, glutamine), amino acids having a hydrocarbon chain (alanine, valine, leucine, isoleucine, proline) and else (glycine, methionine, cysteine).

Mutually replaceable amino acid residues including non-native amino acids may also be classified, for example, as follows, where amino acid residues in the same group can be mutually replaceable with each other. Group A: leucine, isoleucine, norleucine, valine, norvaline, alanine, 2-aminobutanoic acid, methionine, o-methylserine, t-butylglycine, t-butylalanine, cyclohexylalanine; Group B: aspartic acid, glutamic acid, isoaspartic acid, isoglutamic acid, 2-aminoadipic acid, 2-aminosuberic acid; Group C: asparagine, glutamine; Group D: lysine, arginine, ornithine, 2,4-diaminobutanoic acid, 2,3-diaminopropionic acid; Group E: proline, 3-hydroxyproline, 4-hydroxyproline; Group F: serine, threonine, homoserine; and Group G: phenylalanine, tyrosine, tryptophan.

According to the present invention, more preferable antibodies include (a) a heavy chain variable region (HCVR) shown by: the amino acid sequence of SEQ ID NO:10; an amino acid sequence having deletion, substitution, insertion, addition or a combination of two or more of these mutations for one to several (specifically, 1-9, 1-8, 1-7, 1-6, 1-5, 1-4, 1-3, 1-2 or 1) amino acid residues in the amino acid sequence of SEQ ID NO:10; or an amino acid sequence having identity of 95% or higher (preferably, 96% or higher, 97% or higher, 98% or higher, 99% or higher or 99.5% or higher) with the amino acid sequence of SEQ ID NO:10, and (b) a light chain variable region (LCVR) shown by: the amino acid sequence of SEQ ID NO:12; an amino acid sequence having deletion, substitution, insertion, addition or a combination of two or more of these mutations of one to several (specific number being the same as mentioned above) amino acid residues in the amino acid sequence of SEQ ID NO:12; or an amino acid sequence having identity of 95% or higher (specific percentage being the same as mentioned above) with the amino acid sequence of SEQ ID NO:12.

Here, the identity of an amino acid sequence or a nucleotide sequence can be determined by employing BLAST algorithm by Karlin and Altschul (Proc. Natl. Acad. Sci. USA 872264-2268, 1990; Proc Natl Acad Sci USA 90: 5873, 1993). Programs called BLASTN and BLASTX have been developed based on BLAST algorithm (Altschul S F, et al: J Mol Biol 215: 403, 1990). In order to analyze a nucleotide sequence using BLASTN, parameters are set, for example, to score=100 and word length=12. In order to analyze an amino acid sequence using BLASTX, parameters are set, for example, to score=50 and word length=3. In the case of using BLAST and Gapped BLAST programs, default parameters for each program are used.

According to the present invention, still more preferable antibody include (a) a heavy chain variable region (HCVR) represented by the amino acid sequence of SEQ ID NO:10 and (b) a light chain variable region (LCVR) represented by the amino acid sequence of SEQ ID NO:12.

According to the present invention, yet more preferable antibody include (a) a heavy chain (H-chain) shown by: the amino acid sequence of SEQ ID NO:6; an amino acid sequence having deletion, substitution, insertion, addition or a combination of two or more of these mutations for one to several (specific number being the same as mentioned above) amino acid residues in the amino acid sequence of SEQ ID NO:6; or an amino acid sequence having identity of 95% or higher (specific percentage being the same as mentioned above) with the amino acid sequence of SEQ ID NO:6, and (b) a light chain (L-chain) shown by: the amino acid sequence of SEQ ID NO:8; an amino acid sequence having deletion, substitution, insertion, addition or a combination of two or more of these mutations for one to several (specific number being the same as mentioned above) amino acid residues in the amino acid sequence of SEQ ID NO:8; or an amino acid sequence having identity of 95% or higher (specific percentage being the same as mentioned above) with the amino acid sequence of SEQ ID NO:8.

The most preferable antibody according to the present invention is a complete human monoclonal antibody including a heavy chain (H-chain) represented by the amino acid sequence of SEQ ID NO:6 and a light chain (L-chain) represented by the amino acid sequence of SEQ ID NO:8. Moreover, the class (subclass) of a preferable antibody of the invention is IgG1 ($\lambda$).

The above-described anti-HCMV antibody or an antigen-binding fragment thereof according to the present invention specifically binds to HCMV causative of various diseases, neutralizes the bioactivity thereof, and has much higher neutralizing capacity than that of a conventional anti-HCMV antibody.

The phrase "specifically bind to" as used herein means to recognize and bind to a predetermined antigen.

Typically, a dissociation constant (Kd value) between HCMV (especially, human HCMV) and an antibody of the invention is preferably $1 \times 10^{-7}$M or less, more preferably $1 \times 10^{-8}$M or less, still more preferably $1 \times 10^{-9}$M or less, and most preferably $1 \times 10^{-10}$M or less. A dissociation constant between an antibody and HCMV can be determined according to a known method. For example, an anti-HCMV antibody immobilized on a chip may be used for determination using a protein interaction analyzer such as BIACORET100 (registered trademark).

The neutralizing capacity of an anti-HCMV antibody can be assessed by determining an infection blocking rate or a plaque formation blocking rate by immunostaining Specifically, a typical HCMV strain such as AD169 strain and Towne strain is brought into contact with various levels of anti-HCMV antibodies for a predetermined time before inoculating it into an infectable cell culture system. Subsequently, they are inoculated into cells. Twenty-four hours after the infection, the number of HCMV-infected cells may be counted by immunostaining to determine the infection blocking rate, or the number of plaques formed 5-6 days after the infection may be counted to determine the blocking rate thereof, thereby determining the neutralizing activity of the anti-HCMV antibody.

An anti-HCMV antibody or an antigen-binding fragment thereof according to the present invention has approximately 50% plaque formation blocking capacity, i.e., a neutralizing activity against AD169 strain, preferably at 1 µg/mL (approximately 7 nM) or lower, more preferably at 0.1 µg/mL (approximately 0.7 nM) or lower, still more preferably at 0.05 µg/mL (approximately 0.3 nM) or lower and most preferably approximately at 0.03 µg/mL (approximately 0.2 nM) or lower.

In addition, as a cell-to-cell infection blocking capacity, an inhibitory effect for cell-to-cell infection can be assessed by culturing a HCMV-infected cell for a predetermined time and then adding various levels of anti-HCMV antibodies to that cell culture system.

An anti-HCMV antibody or an antigen-binding fragment thereof according to the present invention has 50% or higher cell-to-cell infection blocking capacity at a final concentration of preferably 2 µg/mL (approximately 13 nM) or lower, more preferably 0.5 µg/mL (approximately 3 nM) or lower, and still more preferably 0.2 µg/mL (approximately 0.13 nM) or lower.

An antibody of the present invention can be a recombinant human monoclonal antibody, a monoclonal antibody (including chimeric antibody and humanized antibody) or an antigen-binding fragment thereof that can specifically bind to HCMV and is capable of neutralizing the bioactivity thereof, which can be obtained according to a technique well-known in the art based on a full-length antibody, an antigen-binding fragment thereof, or an amino acid sequence of a variable region of SEQ ID NO:6, 8, 10 or 12, and an amino acid sequence of a complemetarity determining region (CDR) represented by any one of SEQ ID NO:13-18. These antibodies fall within the technical scope of the present invention.

For example, signal sequences of heavy and light chains are cleaved in the course of protein maturation, and thus they do not contribute to the property of the final antibody. In order to add the missing sequence, a cloned cDNA sequence may be combined with a synthetic oligonucleotide by ligation or PCR amplification.

Alternatively, the entire variable region can be synthesized by combining a set of short overlapping oligonucleotides by PCR amplification, thereby preparing a completely artificial clone of the variable region.

2. Nucleic Acid Coding for Antibody or the like of the Present Invention

According to another embodiment of the present invention, an isolated nucleic acid coding for an anti-HCMV monoclonal antibody or an antigen-binding fragment thereof is provided that specifically binds to HCMV and that is capable of neutralizing the bioactivity thereof, where the nucleic acid is selected from nucleic acids coding for an amino acid sequence selected from the group consisting of SEQ ID NOS: 2, 4, 6, 8, 10, 12, 13-18 and 22 and nucleic acids that hybridizes with these nucleic acids under highly stringent conditions.

Preferably, the above-described nucleic acid is either DNA or RNA, and more preferably DNA.

An isolated nucleic acid encoding an anti-HCMV monoclonal antibody or an antigen-binding fragment thereof that binds to HCMV and that is capable of neutralizing the bioactivity thereof, which has high identity with a nucleic acid coding for an amino acid sequence selected from the group consisting of SEQ ID NOS:2, 4, 6, 8, 10, 12, 13-18 and 22 is also encompassed by the present invention. The phrase "having high identity" as used herein refers to sequence identity that is sufficient to hybridize to a predetermined nucleic acid sequence under highly stringent conditions, meaning, for example, identity of 60%, 70%, 80%, 90%, 95% or higher.

"Highly stringent conditions" means, for example, conditions of 5×SSC, 5×Denhardt's solution, 0.5% SDS and 50% formamide at 50° C. (see, for example, J. Sambrook et al., Molecular Cloning, A Laboratory Manual 2nd ed., Cold Spring Harbor Laboratory Press (1989), in particular, section 11.45 "Conditions for Hybridization of Oligonucleotide Probes"). Under these conditions, higher temperature is expected to efficiently give a polynucleotide (for example, DNA) with higher identity. There are, however, appear to be multiple factors that influence the stringency of hybridization such as temperature, probe concentration, probe length, ionic strength, time and salt concentration, and those skilled in the art should be able to appropriately select these factors to realize similar stringency.

Examples of nucleic acids subjected to hybridization under the above-described highly stringent conditions include nucleic acids that have identity of, for example, 70% or higher, 80% or higher, 90% or higher, 95% or higher, 97% or higher or 99% or higher to a nucleic acid coding for an amino acid sequence of any one of SEQ ID NOS:2, 4, 6, 8, 10, 12, 13-18 and 22.

The identity of a nucleotide sequence may be determined by utilizing the above-described identity searching algorithm (Proc. Natl. Acad. Sci. USA 872264-2268, 1990; Proc Natl Acad Sci USA 90: 5873, 1993).

A preferable nucleic acid according to the present invention is DNA coding for both amino acid sequences of SEQ ID NOS:10 and 12, and more preferably DNA coding for both amino acid sequences of SEQ ID NOS:6 and 8. A still more preferable nucleic acid is DNA coding for both amino acid sequences of SEQ ID NOS:2 and 4.

A yet still more preferable nucleic acid is a nucleic acid containing both nucleic acids of SEQ ID NOS:5 and 7, and a still more preferable nucleic acid is a nucleic acid containing both nucleic acids of SEQ ID NOS:1 and 3.

3. Vector, Host Cell and Method for Preparing Antibody of the Invention

The present invention also relates to a vector incorporating the above-described nucleic acid, a host cell introduced with the vector, and a method for preparing an antibody using the same.

An antibody of the present invention may also be prepared as a recombinant human antibody according to a known method (see Nature, 312:643, 1984, Nature, 321:522, 1986, etc.). For example, an antibody of the present invention can be prepared by culturing a host cell introduced with a vector of the invention, and purifying the produced antibody from the culture supernatant or the like. More specifically, an antibody can be prepared by inserting cDNAs coding for $V_H$ and $V_L$ into animal cell expression vectors containing genes coding for human antibody $C_H$ and/or human antibody $C_L$ prepared from the same cell or different human cells to construct a human antibody expression vector and introducing the vector into an animal cell for expression.

Vectors into which nucleic acids coding for $V_H$ or $V_L$ of the antibody of the present invention are incorporated are not necessarily limited, but they are preferably vectors generally used for the expression of a protein gene or the like, and particularly a vector or a high-expression vector that is suitable for expression of an antibody gene. Preferable examples include vectors containing an EF promoter and/or a CMV enhancer. In general, expression vectors each incorporating a nucleic acid coding for $V_H$ or $V_L$ are prepared and used for cotransfecting a host cell, but the nucleic acids may also be incorporated into a single expression vector.

The host cell for introducing the expression vector is not necessarily limited, but it is preferably a cell that is generally used for the expression of a protein gene or the like, and particularly a cell that is suitable for expression of an antibody gene. Examples include a bacterium (E. coli, etc.), actinomycetes, an yeast, an insect cell (SF9, etc.), and a mammal cell (COS-1, CHO, myeloma cell or the like).

In order to industrially produce a recombinant antibody, a recombinant animal cell strain such as CHO cell strain that is highly and stably productive of the antibody is generally utilized. Known gene amplification and screening methods can be employed for preparation, cloning and high expression of such a recombinant cell strain (for example, see Omasa T.: J. Biosci. Bioeng., 94, 600-605, 2002, etc.).

Other than an antibody consisting of two heavy chains and two light chains, the present invention also comprises an antigen-binding fragment of an antibody of the present invention. Examples of antigen-binding fragments include Fab (fragment of antigen binding), Fab' and F(ab')$_2$. Examples of those obtained by linking the active fragments of the antibody via a linker or the like include a single chain antibody (single chain Fv: scFv) and a disulfide stabilized antibody (disulfide stabilized Fv: dsFv). An example of a peptide containing an active fragment of the antibody include a peptide containing CDR. These may be produced according to a known method such as a method in which the antibody of the present invention is treated with an appropriate proteolytic enzyme or a gene recombination technique.

Purification of the antibody can be carried out by using a known purification technique such as salting-out method, gel filtration, ion-exchange chromatography or affinity chromatography.

In addition, $V_H$ and $V_L$ genes can be artificially shuffled to express a diversified scFv (single chain Fragment of variable region) antibody as a phage fusion protein by a recently developed phage display antibody technique in which a recombinant antibody is expressed on a phage surface by a genetic engineering technique, thereby obtaining a specific antibody. This technique is highly appreciated for being able to escape immune system and further as a technique for preparing a humanized antibody as an alternative to cell fusion method. A specific antibody or an antigen-binding fragment thereof prepared using this technique with respect to the amino acid sequence of SEQ ID NOS:2, 4, 6, 8, 10, 12, 13-18 and 22 herein belongs to the technical scope of the present invention.

Moreover, an antibody obtained by applying recently developed Potelligent technique in which ADCC activity of an antibody is greatly improved by modifying the sugar chain moiety of the antibody can be applied to an antibody of the present invention (see Niwa R., et al, Clin. Cancer Res., 10,6248-6255 (2004)) and an antibody obtained by applying Complegnent technique which improves the CDC activity to an antibody of the present invention (see Kanda S., et al, Glycobiology, 17, 104-118 (2007)) also fall within the technical scope of the present invention.

An antibody is generally prepared by obtaining a polyclonal antibody or a monoclonal antibody utilizing an experiment animal such as a mouse, a rabbit, a goat or the like. Since such an antibody has a sequence that is characteristic of the species of animal used, it would be recognized as a foreign substance by the human immune system if directly administered, which may result in human anti-animal antibody response (in other words, an antibody is produced against an antibody).

An anti-HCMV monoclonal antibody or an antigen-binding fragment thereof according to the present invention can be obtained from an antibody-producing cell derived from blood of a healthy human, which is a complete human antibody. When this complete human antibody is administered to a human as an antibody drug, it has no immunogenicity and thus should show no immune response.

Since an anti-HCMV monoclonal antibody of the present invention has a higher neutralizing capacity than that of a conventional anti-HCMV monoclonal antibody, a similar level of the therapeutic effect can be expected with less dosage.

Hereinafter, a procedure for obtaining an anti-HCMV monoclonal antibody and an antigen-binding fragment according to the present invention will be described, but a procedure for obtaining an antibody or the like of the present invention should not be limited to these descriptions and it goes without saying that any modification that is generally conducted in the art can be performed.

An anti-HCMV monoclonal antibody and an antigen-binding fragment thereof according to the present invention can be obtained by: separating a cell clone that produces the antibody from blood of a healthy human through various steps; collecting the antibody from the culture supernatant of the antibody-producing cell clone; and carrying out affinity purification to the antibody obtained.

1) Separation of Cell Clone that Produces Complete Human Antibody Against HCMV

B-lymphocyte is separated from healthy human blood for inducing proliferation of the B-lymphocyte. A method for inducing proliferation is known per se, and can be carried out, for example, by a transformation method using "Epstein-Barr virus (EB virus)" (hereinafter, referred to as EBV) as a cancer-inducing factor (D. Kozbor et al.).

Specifically, the above-mentioned B-lymphocyte is infected with EBV for inducing proliferation, and the proliferated cells are used as an antibody-producing cell library.

2) Collection of Monoclonal Antibody from Antibody-Producing Cell Library

A monoclonal antibody can be collected from proliferation-induced cells according to a well-known method commonly used for preparation of a monoclonal antibody.

From the above-described antibody-producing cell library, a lymphocyte clone that produces an antibody that binds to HCMV is sorted out, and the antibody is removed from the culture supernatant thereof. Specifically, a cell population (clones) that produces an HCMV-binding antibody is selected from the above-described antibody-producing cell library by limiting dilution method.

In order to detect a clone that binds to HCMV, ELISA using an HCMV-derived antigen and a labeled mouse anti-human IgG antibody is preferably employed.

By repeating the cultivation and screening of the selected antibody-positive cell population, a cell population (clones) that produces only the antibody of interest can be obtained.

A flowchart indicating the steps until the separation of a clone of an antibody-producing cell is shown in FIG. 1.

3) Affinity Purification using Protein A or G

In order to purify the anti-HCMV antibody, the sorted out cell can be proliferated in a roller bottle, a 2 L Spinner flask, or other culture system.

The resulting culture supernatant is filtrated to be concentrated and then subjected to affinity chromatography with protein A or protein G-sepharose (GE Healthcare) or the like, thereby purifying the protein. The buffer can be replaced with PBS to determine the concentration by $OD_{280}$ or preferably by nephelometer analysis.

The isotype can be examined by a method specific to the isotype antigen.

Since the thus-obtained anti-HCMV antibody is a complete human antibody prepared from a B-lymphocyte sensitized in a human body, the chance of causing immune response against the antibody is low.

This preparation of an antibody-producing cell clone is also characterized by the use of EB virus that is active in infecting and inducing proliferation of the B-lymphocyte.

Advantages of the EB virus method are that a natural antibody made in human body can be prepared and that an antibody with high affinity can be obtained. For example, a human antibody against HCMV is found to have an affinity that is approximately 10-100 times higher than that of an antibody made by artificially immunizing a mouse.

A B-lymphocyte population proliferated by EB virus infection can be a library of antibody-producing cells.

A specific antibody-producing cell clone can be separated from this library to obtain a human antibody.

4. Pharmaceutical Composition Containing Antibody of the Invention

Next, the present invention provides a pharmaceutical composition for preventing or treating a disease associated with human cytomegalovirus (HCMV), which comprises the above-described antibody or an antigen-binding site thereof and a pharmaceutically acceptable carrier.

Since an anti-HCMV antibody or an antigen-binding fragment thereof according to the present invention has higher neutralizing capacity against HCMV than that of a conventional anti-HCMV antibody, it is useful as a prophylactic or therapeutic drug for an HCMV-related disease (various diseases caused by HCMV). A disease caused by HCMV is a disease whose symptoms and/or progression is expected to be alleviated by inhibition of the HCMV activity.

The term "HCMV-related disease" as used herein comprises, as well as other diseases, a disease that is found to be or that appears to be caused because a target subject suffering from that disease has HCMV as the cause of the pathological conditions of that disease or as a cause of worsening that disease. In other words, since an anti-HCMV antibody or an antigen-binding fragment thereof according to the present invention has a high neutralizing capacity against HCMV, it can be expected as a prophylactic or therapeutic drug for various diseases caused by HCMV, for example: (a) diseases such as interstitial pneumonia, retinitis, gastroenteritis, encephalitis and the like due to HCMV reactivation in immunodeficiency states such as AIDS, cancer, after organ transplantation, after bone-marrow transplantation, after hemodialysis; (b) congenital CMV infection due to transmission of HCMV infection from a pregnant woman to a fetus; (c) miscarriage, stillbirth and death shortly after birth caused by the above-described congenital CMV infection; (d) low birth weight, hepatosplenomegaly, jaundice, thrombocytopenic purpura, microcephaly, disorder of mental development, delay of intellectual development, chorioretinitis and hearing impairment in the case of survival through the above-described congenital CMV infection; and (e) abnormality of hepatic function, interstitial pneumonia and mononucleosis due to HCMV infection during newborn or infancy (Non-Patent Documents 3, 4 and 5).

A "carrier acceptable as a pharmaceutical product" used herein comprises any physiologically adaptable or any solvent, dispersion medium, coating, isotonic agent, absorption retardant and the like.

Examples of carriers acceptable as pharmaceutical products include one or more, or a combination of water, saline solution, phosphate buffered saline, dextrose, glycerol, ethanol and the like. For use as an injectable agent or the like, a pH regulator or an isotonic agent, for example, sugar or polyalcohol such as mannitol and sorbitol or sodium chloride is preferably contained in the composition. A carrier acceptable as a pharmaceutical product can further contain a small amount of auxiliary substance for enhancing the conservative property or effectivity of the antibody or the antibody moiety such as a wetting agent, an emulsifier, an antiseptic agent, a buffer, a stabilizer or the like.

A composition of the present invention may be made into various dosage forms. Examples of such compositions include liquid, semisolid and solid dosage forms such as a solution (for example, an injectable and infusable solution), a dispersion, a suspension, a tablet, a capsule, a lozenge, a pill, powder, a liposome, a suppository and the like. Preferable form differs depending on the intended administration mode and treatment applied. A generally preferable composition is in a form of injectable or infusable solution such as a composition similar to those used for passively immunizing human with other antibody. A preferable administration mode is parenteral (for example, intravenous, subcutaneous, intraperitoneal or intramuscular). According to a preferable embodiment, the antibody is administered by intravenous infusion or intravenous injection. According to another preferable embodiment, the antibody is administered by intramuscular injection or subcutaneous injection.

An antibody and an antibody fragment according to the present invention can be incorporated into a pharmaceutical composition suitable for parenteral administration. When a single type of antibody or antibody moiety is used, it is preferably prepared as an injectable formulation containing the antibody for 0.1-250 mg/mL. On the other hand, when multiple types of antibodies are used as a mixture, they are preferably prepared as an injectable formulation containing the antibody for 0.001-100 mg/mL. The mix proportion of the multiple types of antibodies may be determined accordingly.

An injectable formulation may be a product obtained by dissolving the effective component in a liquid or a lyophilized product of the effective component, which is placed in a flint or umber vial, an ampule or a prefilled syringe. The buffer may be L-histidine (1-50 mM) at pH5.0-7.0 (optimally pH6.0), and optimally 5-10 mM of L-histidine. Examples of other suitable buffers include, but not limited to, sodium succinate, sodium citrate, sodium phosphate or potassium phosphate. In order to alter an osmotic pressure of a solution at a concentration of 0-300 mM (optimally 150 mM in the case of a liquid dosage form), sodium chloride may be used. The lyophilized dosage form can contain a cryoprotectant, mainly 0-10% (optimally 0.5-5.0%) of sucrose. Other appropriate cryoprotectants include mannitol, trehalose and lactose. The lyophilized dosage form may contain, a filler, mainly 1-10% (optimally 2-4%) of mannitol. For both of the liquid and lyophilized dosage forms, a stabilizer, mainly 1-50 mM (optimally 5-10 mM) of L-methionine, can be used. Other appropriate stabilizers include glycine, arginine and polysorbate 80 and the like. In the case of polysorbate 80, it may be contained for 0-0.05% (optimally 0.005-0.01%). Other surfactants include, but not limited to, polysorbate 20 and BRIJ surfactant.

This pharmaceutical composition should generally be sterile and stable under the production and storage conditions. This composition may be formulated into other ordered structure that is appropriate for a solution, a microemulsion, a dispersion, a liposome or a high drug concentration. A sterile injectable solution can be prepared by mixing a requisite amount of active compound (that is, the antibody or the antibody moiety) with an appropriate solvent, and if necessary, with any one of or in combination with the above-described components, and then subjecting the resultant to filtration sterilization. In general, a dispersion is prepared by mixing the active compound with a basic dispersion medium and a sterile vehicle containing other necessary components selected among the above-listed components. A preferable method for preparing a sterile powder formulation used for preparing a sterile injectable solution comprises subjecting the above-described sterile filtrated solution to vacuum-freeze drying and spray drying, thereby obtaining a composition containing any other desired component as well as the active component powder. An appropriate fluidity of the solution can be maintained by using, for example, a coating agent such as lecithin, by maintaining the requisite particle size in the case of the dispersion, or by using a surfactant. Long lasting absorption of the injectable composition can be realized by adding an agent that can delay the absorption, for example, monostearate or gelatin to the composition.

The pharmaceutical composition of the invention may also contain a supplementary active compound. According to one embodiment, an antibody or an antibody moiety of the present invention is formulated together with one or more other therapeutic drugs that are useful for treating a disease caused by HCMV, or administered with such other therapeutic drug. For example, an anti-HCMV antibody or an antibody moiety of the present invention may be formulated together with one or more other antibodies that binds to other target (for example, an antibody that binds to other binding site of HCMV), or simultaneously administered with such other antibody. In addition, one or more antibodies of the present invention can be used by combining two or more types of the above-described therapeutic drugs. Such combined therapy can advantageously utilize lower doses of the administered therapeutic drugs and thus possible toxicity or complication associated with various single therapies can be avoided.

Here, the relationships between the nucleotides or the amino acid sequences with the sequence numbers mentioned in the present specification are as follows.

SEQ ID NO:1 represents a nucleotide sequence coding for an H-chain of an antibody against the AD1 region of HCMV glycoprotein gB (hereinafter, "anti-AD1 antibody") (EV2038) with a signal sequence.

SEQ ID NO:2 represents an amino acid sequence of an H-chain of an anti-AD1 antibody (EV2038) with a signal sequence.

SEQ ID NO:3 represents a nucleotide sequence coding for an L-chain of an anti-AD1 antibody (EV2038) with a signal sequence.

SEQ ID NO:4 represents an amino acid sequence of an L-chain of an anti-AD1 antibody (EV2038) with a signal sequence SEQ ID NO:5 represents a nucleotide sequence coding for an H-chain of an anti-AD1 antibody (EV2038) without a signal sequence.

SEQ ID NO:6 represents an amino acid sequence of an H-chain of an anti-AD1 antibody (EV2038) without a signal sequence.

SEQ ID NO:7 represents a nucleotide sequence coding for an L-chain of an anti-AD1 antibody (EV2038) without a signal sequence.

SEQ ID NO:8 represents an amino acid sequence of an L-chain of an anti-AD1 antibody (EV2038) without a signal sequence.

SEQ ID NO:9 represents a nucleotide sequence coding for an H-chain variable region of anti-AD1 antibody (EV2038).

SEQ ID NO:10 represents an amino acid sequence of an H-chain variable region of an anti-AD1 antibody (EV2038).

SEQ ID NO:11 represents a nucleotide sequence coding for an L-chain variable region of an anti-AD1 antibody (EV2038).

SEQ ID NO:12 represents an amino acid sequence of an L-chain variable region of an anti-AD1 antibody (EV2038).

SEQ ID NO:13 represents an amino acid sequence of an H-chain CDR1 of an anti-AD1 antibody (EV2038).

SEQ ID NO:14 represents an amino acid sequence of an H-chain CDR2 of an anti-AD1 antibody (EV2038).

SEQ ID NO:15 represents an amino acid sequence of an H-chain CDR3 of an anti-AD1 antibody (EV2038).

SEQ ID NO:16 represents an amino acid sequence of an L-chain CDR1 of an anti-AD1 antibody (EV2038).

SEQ ID NO:17 represents an amino acid sequence of an L-chain CDR2 of an anti-AD1 antibody (EV2038).

SEQ ID NO:18 represents an amino acid sequence of an L-chain CDR3 of an anti-AD1 antibody (EV2038).

SEQ ID NO:19 represents a nucleotide sequence of 38 Hind-S primer used for producing a CDR-H3 variant of EV2038 in a working example.

SEQ ID NO:20 represents a nucleotide sequence of 38 Not-A primer used for producing a CDR-H3 variant of EV2038 in a working example.

SEQ ID NO:21 represents a nucleotide sequence of a primer for verifying a nucleotide sequence used for producing CDR-H3 variant of EV2038 in a working example.

SEQ ID NO:22 represents a consensus amino acid sequence in the amino acid sequence of CDR-H3 of an anti-AD1 antibody.

SEQ ID NO:23 represents an amino acid sequence having amino acid residues at positions 549-580 of the AD1 region of HCMV glycoprotein gB, which has been identified as an epitope-existing region by a deletion mutation technique described in the example.

SEQ ID NO:24 represents an amino acid sequence having amino acid residues at positions 596-640 of the AD1 region of HCMV glycoprotein gB, which has been identified as an epitope-existing region by a deletion mutation technique described in the example.

SEQ ID NO:25 represents an amino acid sequence having amino acid residues at positions 549-560 of the AD1 region of HCMV glycoprotein gB, which has been identified as an epitope region by a peptide array technique described in the example.

SEQ ID NO:26 represents an amino acid sequence having amino acid residues at positions 569-576 of the AD1 region of HCMV glycoprotein gB, which has been identified as an epitope region by a peptide array technique described in the example.

SEQ ID NO:27 represents an amino acid sequence having amino acid residues at positions 625-632 of the AD1 region of HCMV glycoprotein gB, which has been identified as an epitope region by a peptide array technique described in the example.

SEQ ID NO:28 represents an amino acid sequence of a mutant where valine (V) has been substituted with lysine (K) at position 117 in the amino acid sequence of the H-chain of an anti-AD1 antibody (EV2038) of the present invention.

SEQ ID NO:29 represents an amino acid sequence of a mutant where threonine (T) has been substituted with tryptophan (W) at position 118 in the amino acid sequence of the H-chain of an anti-AD1 antibody (EV2038) of the present invention.

SEQ ID NO:30 represents an amino acid sequence of a mutant where arginine (R) has been substituted with valine (V) at position 119 in the amino acid sequence of the H-chain of an anti-AD1 antibody (EV2038) of the present invention.

SEQ ID NO:31 represents an amino acid sequence of a mutant where aspartic acid (D) has been substituted with isoleucine (I) at position 120 in the amino acid sequence of the H-chain of an anti-AD1 antibody (EV2038) of the present invention.

SEQ ID NO:32 represents an amino acid sequence of a mutant where leucine (L) has been substituted with glutamic acid (E) at position 121 in the amino acid sequence of the H-chain of an anti-AD1 antibody (EV2038) of the present invention.

SEQ ID NO:33 represents an amino acid sequence of a mutant where glutamic acid (E) has been substituted with leucine (L) at position 122 in the amino acid sequence of the H-chain of an anti-AD1 antibody (EV2038) of the present invention.

SEQ ID NO:34 represents an amino acid sequence of a mutant where tryptophan (W) has been substituted with threonine (T) at position 123 in the amino acid sequence of the H-chain of an anti-AD1 antibody (EV2038) of the present invention.

SEQ ID NO:35 represents an amino acid sequence of a mutant where isoleucine (I) has been substituted with aspartic acid (D) at position 124 in the amino acid sequence of the H-chain of an anti-AD1 antibody (EV2038) of the present invention.

SEQ ID NO:36 represents an amino acid sequence of a mutant where proline (P) has been substituted with arginine (R) at position 125 in the amino acid sequence of the H-chain of an anti-AD1 antibody (EV2038) of the present invention.

SEQ ID NO:37 represents an amino acid sequence of a mutant where glycine (G) has been substituted with phenylalanine (F) at position 126 in the amino acid sequence of the H-chain of an anti-AD1 antibody (EV2038) of the present invention.

SEQ ID NO:38 represents an amino acid sequence of a mutant where aspartic acid (D) has been substituted with isoleucine (I) at position 127 in the amino acid sequence of the H-chain of an anti-AD1 antibody (EV2038) of the present invention.

SEQ ID NO:39 represents an amino acid sequence of a mutant where tyrosine (Y) has been substituted with asparagine (N) at position 128 in the amino acid sequence of the H-chain of an anti-AD1 antibody (EV2038) of the present invention.

SEQ ID NO:40 represents an amino acid sequence of a mutant where tyrosine (Y) has been substituted with asparagine (N) at position 129 in the amino acid sequence of the H-chain of an anti-AD1 antibody (EV2038) of the present invention.

SEQ ID NO:41 represents an amino acid sequence of a mutant where methionine (M) has been substituted with glutamine (Q) at position 130 in the amino acid sequence of the H-chain of an anti-AD1 antibody (EV2038) of the present invention.

SEQ ID NO:42 represents an amino acid sequence of a mutant where aspartic acid (D) has been substituted with isoleucine (I) at position 131 in the amino acid sequence of the H-chain of an anti-AD1 antibody (EV2038) of the present invention.

SEQ ID NO:43 represents an amino acid sequence of a mutant where valine (V) has been substituted with lysine (K) at position 132 in the amino acid sequence of the H-chain of an anti-AD1 antibody (EV2038) of the present invention.

SEQ ID NO:44 represents an amino acid sequence of a mutant where leucine (L) has been substituted with isoleucine (I) at position 121 in the amino acid sequence of the H-chain of an anti-AD1 antibody (EV2038) of the present invention.

SEQ ID NO:45 represents an amino acid sequence of a mutant where leucine (L) has been substituted with valine (V) at position 121 in the amino acid sequence of the H-chain of an anti-AD1 antibody (EV2038) of the present invention.

SEQ ID NO:46 represents an amino acid sequence of a mutant where leucine (L) has been substituted with alanine (A) at position 121 in the amino acid sequence of the H-chain of an anti-AD1 antibody (EV2038) of the present invention.

SEQ ID NO:47 represents an amino acid sequence of a mutant where leucine (L) has been substituted with phenylalanine (F) at position 121 in the amino acid sequence of the H-chain of an anti-AD1 antibody (EV2038) of the present invention.

SEQ ID NO:48 represents an amino acid sequence of a mutant where leucine (L) has been substituted with proline (P) at position 121 in the amino acid sequence of the H-chain of an anti-AD1 antibody (EV2038) of the present invention.

SEQ ID NO:49 represents an amino acid sequence of a mutant where tryptophan (W) has been substituted with tyrosine (Y) at position 123 in the amino acid sequence of the H-chain of an anti-AD1 antibody (EV2038) of the present invention.

SEQ ID NO:50 represents an amino acid sequence of a mutant where tryptophan (W) has been substituted with phenylalanine (F) at position 123 in the amino acid sequence of the H-chain of an anti-AD1 antibody (EV2038) of the present invention.

SEQ ID NO:51 represents an amino acid sequence of a mutant where tryptophan (W) has been substituted with proline (P) at position 123 in the amino acid sequence of the H-chain of an anti-AD1 antibody (EV2038) of the present invention.

SEQ ID NO:52 represents an amino acid sequence of a mutant where tryptophan (W) has been substituted with leucine (L) at position 123 in the amino acid sequence of the H-chain of an anti-AD1 antibody (EV2038) of the present invention.

SEQ ID NO:53 represents an amino acid sequence of a mutant where tryptophan (W) has been substituted with isoleucine (I) at position 123 in the amino acid sequence of the H-chain of an anti-AD1 antibody (EV2038) of the present invention.

SEQ ID NO:54 represents an amino acid sequence of a mutant where isoleucine (I) has been substituted with leucine (L) at position 124 in the amino acid sequence of the H-chain of an anti-AD1 antibody (EV2038) of the present invention.

SEQ ID NO:55 represents an amino acid sequence of a mutant where isoleucine (I) has been substituted with methionine (M) at position 124 in the amino acid sequence of the H-chain of an anti-AD1 antibody (EV2038) of the present invention.

SEQ ID NO:56 represents an amino acid sequence of a mutant where isoleucine (I) has been substituted with proline (P) at position 124 in the amino acid sequence of the H-chain of an anti-AD1 antibody (EV2038) of the present invention.

SEQ ID NO:57 represents an amino acid sequence of a mutant where isoleucine (I) has been substituted with valine (V) at position 124 in the amino acid sequence of the H-chain of an anti-AD1 antibody (EV2038) of the present invention.

SEQ ID NO:58 represents an amino acid sequence of a mutant where isoleucine (I) has been substituted with alanine (A) at position 124 in the amino acid sequence of the H-chain of an anti-AD1 antibody (EV2038) of the present invention.

SEQ ID NO:59 represents an amino acid sequence of a mutant where glycine (G) has been substituted with proline (P) at position 126 in the amino acid sequence of the H-chain of an anti-AD1 antibody (EV2038) of the present invention.

SEQ ID NO:60 represents an amino acid sequence of a mutant where glycine (G) has been substituted with alanine (A) at position 126 in the amino acid sequence of the H-chain of an anti-AD1 antibody (EV2038) of the present invention.

SEQ ID NO:61 represents an amino acid sequence of a mutant where glycine (G) has been substituted with serine (S) at position 126 in the amino acid sequence of the H-chain of an anti-AD1 antibody (EV2038) of the present invention.

SEQ ID NO:62 represents an amino acid sequence of a mutant where glycine (G) has been substituted with asparagine (N) at position 126 in the amino acid sequence of the H-chain of an anti-AD1 antibody (EV2038) of the present invention.

SEQ ID NO:63 represents an amino acid sequence of a mutant where glycine (G) has been substituted with threonine (T) at position 126 in the amino acid sequence of the H-chain of an anti-AD1 antibody (EV2038) of the present invention.

SEQ ID NO:64 represents an amino acid sequence of a mutant where proline (P) has been substituted with glycine (G) at position 125 in the amino acid sequence of the H-chain of an anti-AD1 antibody (EV2038) of the present invention.

SEQ ID NO:65 represents an amino acid sequence of a mutant where proline (P) has been substituted with isoleucine (I) at position 125 in the amino acid sequence of the H-chain of an anti-AD1 antibody (EV2038) of the present invention.

SEQ ID NO:66 represents an amino acid sequence of a mutant where proline (P) has been substituted with alanine (A) at position 125 in the amino acid sequence of the H-chain of an anti-AD1 antibody (EV2038) of the present invention.

SEQ ID NO:67 represents an amino acid sequence of a mutant where proline (P) has been substituted with leucine (L) at position 125 in the amino acid sequence of the H-chain of an anti-AD1 antibody (EV2038) of the present invention.

SEQ ID NO:68 represents an amino acid sequence of a mutant where proline (P) has been substituted with valine (V) at position 125 in the amino acid sequence of the H-chain of an anti-AD1 antibody (EV2038) of the present invention.

SEQ ID NO:69 represents an amino acid sequence of a mutant where proline (P) has been substituted with serine (S) at position 125 in the amino acid sequence of the H-chain of an anti-AD1 antibody (EV2038) of the present invention.

SEQ ID NO:70 represents an amino acid sequence of a mutant where proline (P) has been substituted with threonine (T) at position 125 in the amino acid sequence of the H-chain of an anti-AD1 antibody (EV2038) of the present invention.

SEQ ID NO:71 represents an amino acid sequence of a mutant where proline (P) has been substituted with asparagine (N) at position 125 in the amino acid sequence of the H-chain of an anti-AD1 antibody (EV2038) of the present invention.

SEQ ID NO:72 represents an amino acid sequence of a mutant where proline (P) has been substituted with glutamine (Q) at position 125 in the amino acid sequence of the H-chain of an anti-AD1 antibody (EV2038) of the present invention.

SEQ ID NO:73 represents an amino acid sequence of a mutant where proline (P) has been substituted with aspartic acid (D) at position 125 in the amino acid sequence of the H-chain of an anti-AD1 antibody (EV2038) of the present invention.

SEQ ID NO:74 represents an amino acid sequence of a mutant where proline (P) has been substituted with glutamic acid (E) at position 125 in the amino acid sequence of the H-chain of an anti-AD1 antibody (EV2038) of the present invention.

SEQ ID NO:75 represents an amino acid sequence of a mutant where proline (P) has been substituted with lysine (K) at position 125 in the amino acid sequence of the H-chain of an anti-AD1 antibody (EV2038) of the present invention.

SEQ ID NO:76 represents an amino acid sequence of a mutant where proline (P) has been substituted with histidine (H) at position 125 in the amino acid sequence of the H-chain of an anti-AD1 antibody (EV2038) of the present invention.

SEQ ID NO:77 represents an amino acid sequence of a mutant where proline (P) has been substituted with cysteine (C) at position at position 125 in the amino acid sequence of the H-chain of an anti-AD1 antibody (EV2038) of the present invention.

SEQ ID NO:78 represents an amino acid sequence of a mutant where proline (P) has been substituted with methionine (M) at position 125 in the amino acid sequence of the H-chain of an anti-AD1 antibody (EV2038) of the present invention.

SEQ ID NO:79 represents an amino acid sequence of a mutant where proline (P) has been substituted with tyrosine (Y) at position 125 in the amino acid sequence of the H-chain of an anti-AD1 antibody (EV2038) of the present invention.

SEQ ID NO:80 represents an amino acid sequence of a mutant where proline (P) has been substituted with tryptophan (W) at position 125 in the amino acid sequence of the H-chain of an anti-AD1 antibody (EV2038) of the present invention.

SEQ ID NO:81 represents an amino acid sequence of a mutant where proline (P) has been substituted with phenylalanine (F) at position 125 in the amino acid sequence of the H-chain of an anti-AD1 antibody (EV2038) of the present invention.

SEQ ID NO:82 represents an amino acid sequence of a mutant where valine (V) has been substituted with leucine (L) at position 117 in the amino acid sequence of the H-chain of an anti-AD1 antibody (EV2038) of the present invention.

SEQ ID NO:83 represents an amino acid sequence of a mutant where valine (V) has been substituted with isoleucine (I) at position 117 in the amino acid sequence of the H-chain of an anti-AD1 antibody (EV2038) of the present invention.

SEQ ID NO:84 represents an amino acid sequence of a mutant where threonine (T) has been substituted with serine (S) at position 118 in the amino acid sequence of the H-chain of an anti-AD1 antibody (EV2038) of the present invention.

SEQ ID NO:85 represents an amino acid sequence of a mutant where threonine (T) has been substituted with lysine (K) at position 118 in the amino acid sequence of the H-chain of an anti-AD1 antibody (EV2038) of the present invention.

SEQ ID NO:86 represents an amino acid sequence of a mutant where arginine (R) has been substituted with lysine (K) at position 119 in the amino acid sequence of the H-chain of an anti-AD1 antibody (EV2038) of the present invention.

SEQ ID NO:87 represents an amino acid sequence of a mutant where arginine (R) has been substituted with threonine (T) at position 119 in the amino acid sequence of the H-chain of an anti-AD1 antibody (EV2038) of the present invention.

SEQ ID NO:88 represents an amino acid sequence of a mutant where aspartic acid (D) has been substituted with glutamic acid (E) at position 120 in the amino acid sequence of the H-chain of an anti-AD1 antibody (EV2038) of the present invention.

SEQ ID NO:89 represents an amino acid sequence of a mutant where aspartic acid (D) has been substituted with alanine (A) at position 120 in the amino acid sequence of the H-chain of an anti-AD1 antibody (EV2038) of the present invention.

SEQ ID NO:90 represents an amino acid sequence of a mutant where glutamic acid (E) has been substituted with aspartic acid (D) at position 122 in the amino acid sequence of the H-chain of an anti-AD1 antibody (EV2038) of the present invention.

SEQ ID NO:91 represents an amino acid sequence of a mutant where glutamic acid (E) has been substituted with alanine (A) at position 122 in the amino acid sequence of the H-chain of an anti-AD1 antibody (EV2038) of the present invention.

SEQ ID NO:92 represents an amino acid sequence of a mutant where aspartic acid (D) has been substituted with glutamic acid (E) at position 127 in the amino acid sequence of the H-chain of an anti-AD1 antibody (EV2038) of the present invention.

SEQ ID NO:93 represents an amino acid sequence of a mutant where aspartic acid (D) has been substituted with alanine (A) at position 127 in the amino acid sequence of the H-chain of an anti-AD1 antibody (EV2038) of the present invention.

SEQ ID NO:94 represents an amino acid sequence of a mutant where tyrosine (Y) has been substituted with phenylalanine (F) at position 128 in the amino acid sequence of the H-chain of an anti-AD1 antibody (EV2038) of the present invention.

SEQ ID NO:95 represents an amino acid sequence of a mutant where tyrosine (Y) has been substituted with tryptophan (W) at position 128 in the amino acid sequence of the H-chain of an anti-AD1 antibody (EV2038) of the present invention.

SEQ ID NO:96 represents an amino acid sequence of a mutant where tyrosine (Y) has been substituted with phenylalanine (F) at position 129 in the amino acid sequence of the H-chain of an anti-AD1 antibody (EV2038) of the present invention.

SEQ ID NO:97 represents an amino acid sequence of a mutant where tyrosine (Y) has been substituted with tryptophan (W) at position 129 in the amino acid sequence of the H-chain of an anti-AD1 antibody (EV2038) of the present invention.

SEQ ID NO:98 represents an amino acid sequence of a mutant where methionine (M) has been substituted with phenylalanine (F) at position 130 in the amino acid sequence of the H-chain of an anti-AD1 antibody (EV2038) of the present invention.

SEQ ID NO:99 represents an amino acid sequence of a mutant where methionine (M) has been substituted with isoleucine (I) at position 130 in the amino acid sequence of the H-chain of an anti-AD1 antibody (EV2038) of the present invention.

SEQ ID NO:100 represents an amino acid sequence of a mutant where aspartic acid (D) has been substituted with glutamic acid (E) at position 131 in the amino acid sequence of the H-chain of an anti-AD1 antibody (EV2038) of the present invention.

SEQ ID NO:101 represents an amino acid sequence of a mutant where aspartic acid (D) has been substituted with alanine (A) at position 131 in the amino acid sequence of the H-chain of an anti-AD1 antibody (EV2038) of the present invention.

SEQ ID NO:102 represents an amino acid sequence of a mutant where valine (V) has been substituted with tyrosine (Y) at position 132 in the amino acid sequence of the H-chain of an anti-AD1 antibody (EV2038) of the present invention.

SEQ ID NO:103 represents an amino acid sequence of a mutant where valine (V) has been substituted with serine (S) at position 132 in the amino acid sequence of the H-chain of an anti-AD1 antibody (EV2038) of the present invention.

SEQ ID NO:104 represents an amino acid sequence of a mutant where isoleucine (I) has been substituted with valine (V) at position 124 and glycine (G) has been substituted with alanine (A) at position 126 in the amino acid sequence of the H-chain of an anti-AD1 antibody (EV2038) of the present invention.

SEQ ID NO:105 represents an amino acid sequence of a mutant where isoleucine (I) has been substituted with valine (V) at position 124 and glycine (G) has been substituted with serine (S) at position 126 in the amino acid sequence of the H-chain of an anti-AD1 antibody (EV2038) of the present invention.

SEQ ID NO:106 represents an amino acid sequence of a mutant where leucine (L) has been substituted with isoleucine (I) at position 121, tryptophan (W) has been substituted with tyrosine (Y) at position 123, isoleucine (I) has been substituted with valine (V) at position 124, and glycine (G) has been substituted with alanine (A) at position 126 in the amino acid sequence of the H-chain of an anti-AD1 antibody (EV2038) of the present invention.

SEQ ID NO:107 represents an amino acid sequence of a mutant where leucine (L) has been substituted with isoleucine (I) at position 121, tryptophan (W) has been substituted with tyrosine (Y) at position 123, isoleucine (I) has been substituted with valine (V) at position 124, and glycine (G) has been substituted with serine (S) at position 126 in the amino acid sequence of the H-chain of an anti-AD1 antibody (EV2038) of the present invention.

SEQ ID NO:108 represents an amino acid sequence of a mutant where glutamic acid (E) at position of 122 has been deleted from the amino acid sequence of the H-chain of an anti-AD1 antibody (EV2038) of the present invention.

SEQ ID NO:109 represents an amino acid sequence of a mutant where glutamic acid (E) has been inserted between glycine (G) at position 126 and aspartic acid (D) at position 127 in the amino acid sequence of the H-chain of an anti-AD1 antibody (EV2038) of the present invention.

SEQ ID NO:110 represents an amino acid sequence of a mutant where asparagine (N) at position 79 has been substituted with glutamine (Q) in the amino acid sequence of the H-chain of an anti-AD1 antibody (EV2038) of the present invention.

SEQ ID NO:111 represents an amino acid sequence of a synthetic peptide (Peptide 1 in Table 5) prepared and used in Example 8.

SEQ ID NO:112 represents an amino acid sequence of a synthetic peptide (Peptide 2 in Table 5) prepared and used in Example 8.

SEQ ID NO:113 represents an amino acid sequence of a synthetic peptide (Peptide 3 in Table 5) prepared and used in Example 8.

SEQ ID NO:114 represents an amino acid sequence of a synthetic peptide (Peptide 4 in Table 5) prepared and used in Example 8.

SEQ ID NO:115 represents an amino acid sequence of a synthetic peptide (Peptide 5 in Table 5) prepared and used in Example 8.

SEQ ID NO:116 represents an amino acid sequence of a synthetic peptide (Peptide 6 in Table 5) prepared and used in Example 8.

SEQ ID NO:117 represents an amino acid sequence of a synthetic peptide (Peptide 7 in Table 5) prepared and used in Example 8.

SEQ ID NO:118 represents an amino acid sequence of a synthetic peptide (Peptide 8 in Table 5) prepared and used in Example 8.

SEQ ID NO:119 represents an amino acid sequence of a synthetic peptide (Peptide 9 in Table 5) prepared and used in Example 8.

SEQ ID NO:120 represents an amino acid sequence of a synthetic peptide (Peptide 10 in Table 5) prepared and used in Example 8.

SEQ ID NO:121 represents an amino acid sequence of a synthetic peptide (Peptide 11 in Table 5) prepared and used in Example 8.

SEQ ID NO:122 represents an amino acid sequence of a synthetic peptide (Peptide 12 in Table 5) prepared and used in Example 8.

SEQ ID NO:123 represents an amino acid sequence of a synthetic peptide (Peptide 13 in Table 5) prepared and used in Example 8.

SEQ ID NO:124 represents an amino acid sequence of a synthetic peptide (Peptide 14 in Table 5) prepared and used in Example 8.

SEQ ID NO:125 represents an amino acid sequence of a synthetic peptide (Peptide 15 in Table 5) prepared and used in Example 8.

SEQ ID NO:126 represents an amino acid sequence of a synthetic peptide (Peptide 16 in Table 5) prepared and used in Example 8.

SEQ ID NO:127 represents an amino acid sequence of a synthetic peptide (Peptide 17 in Table 5) prepared and used in Example 8.

SEQ ID NO:128 represents an amino acid sequence of a synthetic peptide (Peptide 18 in Table 5) prepared and used in Example 8.

SEQ ID NO:129 represents an amino acid sequence of a synthetic peptide (Peptide 19 in Table 5) prepared and used in Example 8.

SEQ ID NO:130 represents an amino acid sequence of a synthetic peptide (Peptide 20 in Table 5) prepared and used in Example 8.

SEQ ID NO:131 represents an amino acid sequence of a synthetic peptide (Peptide 21 in Table 5) prepared and used in Example 8.

SEQ ID NO:132 represents an amino acid sequence of a synthetic peptide (Peptide 22 in Table 5) prepared and used in Example 8.

SEQ ID NO:133 represents an amino acid sequence of a synthetic peptide (Peptide 23 in Table 5) prepared and used in Example 8.

SEQ ID NO:134 represents an amino acid sequence of a synthetic peptide (Peptide 24 in Table 5) prepared and used in Example 8.

SEQ ID NO:135 represents an amino acid sequence of a synthetic peptide (Peptide 25 in Table 5) prepared and used in Example 8.

SEQ ID NO:136 represents an amino acid sequence of a synthetic peptide (Peptide 26 in Table 5) prepared and used in Example 8.

SEQ ID NO:137 represents an amino acid sequence of glycoprotein gB of human cytomegalovirus (HCMV) (Swiss-Prot: P06473).

Here, the relationships between the nucleotide sequences or the amino acid sequences that appear in Examples 1-6 of the present application and the sequence numbers are as shown in Table 1 below.

TABLE 1

| | | With signal sequence | Without signal sequence | Variable region | CDR1 | CDR2 | CDR3 |
|---|---|---|---|---|---|---|---|
| H-chain | NO. of nucleotide sequence | 1 | 5 | 9 | — | — | — |
| | NO. of amino acid sequence | 2 | 6 | 10 | 13 | 14 | 15 |
| L-chain | NO. of nucleotide sequence | 3 | 7 | 11 | — | — | — |
| | NO. of amino acid sequence | 4 | 8 | 12 | 16 | 17 | 18 |

Hereinafter, the present invention will be described more specifically by means of examples, although the present invention should not in any way be limited to these examples.

Unless otherwise stated, procedures used in the examples can be referred to in Molecular Cloning: A Laboratory Manual (Third Edition) (Sambrook et al., Cold Spring Harbour Laboratory Press, 2001).

EXAMPLES

Example 1

Separation of Cell Clone that Produces Complete Human Antibody Against HCMV

A flowchart of steps to the separation of an antibody-producing cell clone is shown in FIG. 1.

B-lymphocyte was separated from human peripheral blood whose anti-HCMV antibody level in the serum is high, and was infected with EBV. The infected cell was seeded into a 96-well plate. After approximately 3 weeks of cultivation, screening was conducted for an anti-HCMV antibody in the culture supernatant (primary screening). The screening was conducted by ELISA method using a 96-well plate coated with GST-fused HCMV-AD1 or GST-fused HCMV-AD2, targeting antibodies for the major neutralizing epitopes AD1 and AD2 of HCMV (J. Virol., 65, 138-146 (1991), J. Gen. Virol., 73, 2375-2383 (1992), J. Virol., 66, 5290-5297 (1992), J. Virol., 67, 703-710 (1993)). Cells in each well that had been confirmed of anti-HCMV antibody production were diluted, and seeded into a new 96-well plate. After approximately 3 weeks of cultivation, secondary screening for anti-HCMV antibody production was conducted. Cells in the resulting antibody positive wells were seeded into a new 96-well plate at 1-30 cells/well. As a result of this cloning manipulation by limiting dilution cultivation, a cell clone producing an antibody of interest was obtained.

Example 2

Identification of Isotype and Subclass of Antibody

The culture supernatant of the separated antibody-producing cell clone was used to identify the isotype of the produced antibody by ELISA method (literature reference: see Curr Protoc Immunol. 2001 May; Chapter 2: Unit 2.2). For ELISA, a 96-well plate coated with GST-fused HCMV-AD1 or AD2 and an antibody specific for each of the isotypes and subclasses as a secondary antibody were used. The results of the isotype and subclass of the resulting anti-HCMV antibody are shown in Table 2.

TABLE 2

| Antibody number | Target antigen | Subclass |
|---|---|---|
| EV2038 | AD1 | IgG1λ |

Example 3

Cloning of DNA Coding for Anti-HCMV Antibody cDNA was obtained from total-RNA of the antibody-producing cell by reverse transcription using Oligo-dT primers and was used as a template in a PCR method to amplify the antibody gene. The primers used for PCR were designed based on database of cDNAs coding for human IgG antibody H- and L-chains. In order to amplify full-length H-chain cDNA and L-chain cDNA, 5'- and 3'-terminal primers had a translation initiation site and a translation termination site, respectively.

Example 4

Determination of Amino Acid Sequence of Antibody Based on Nucleotide Sequence cDNAs of the antibody H- and L-chains amplified by PCR method were inserted into a plasmid vector to identify each of the nucleotide sequence with ABI sequencer. From the resulting nucleotide sequences, the signal sequence and the amino acid sequences of the H- and L-chains of the antibody were determined.

In addition, the complemetarity determining region (CDR) of the antibody was analyzed according to the method of Kabat. The CDR sequences of the resulting anti-HCMV antibody (EV2038) are of SEQ ID NOS: 13-18. Specifically, amino acid sequences of H-chain CDR1, H-chain CDR2, H-chain CDR3, L-chain CDR1, L-chain CDR2 and L-chain CDR3 of EV2038 are of SEQ ID NOS:13, 14, 15, 16, 17 and 18, respectively.

In order to examine similarity to a monoclonal antibodies that had previously been reported as AD1 antibodies, the CDR sequences of EV2038 were compared with antibodies whose amino acid sequences of the variable regions had been registered with GenBank or the like. Each type of CDR sequences of known human or mouse-derived AD1 antibodies was identified by Kabat method, and compared to the similarly-identified CDR sequence of EV2038. In Table 3, the homology (%) of individual CDR was determined based on the number of amino acid residues of the target for comparison (denominator) and the number of amino acid residues whose positions and the types that correspond to those of EV2038 in the CRD moiety (numerator). The total (%) was determined by summing the numbers of amino acid residues as the denominator and the numbers of amino acid residues as the numerator obtained by the comparison of individual CDR, that is, obtaining total homology (%) from the resulting total number of amino acid residues of the denominator and the numerator. As can be appreciated from Table 3, EV2038 has no high-homology with known AD1 antibodies, showing that there is a great difference in the CDR sequences from the previously reported AD1 antibodies.

tion conditions were those recommended by the column manufacturer. After the purification, HCMV-AD1- or HCMV-AD2-binding property of the antibody was verified by ELISA. In addition, the antibody H-chain of approximately 50 kDa and the antibody L-chain of approximately 25 kDa were verified by SDS-PAGE.

Example 7

Preparation of Variants and Binding Activities thereof

In order to study amino acid sequences that influence the property of the antibody of the present invention or the binding fragment thereof, CDR-H3 region (amino acids 117-132) was particularly studied. Here, the numbers of the amino acid

TABLE 3

| Antibody | Accession No. (HCVR/LCVR) | Source | Homology of H-chain CDR (%) | | | Homology of L-chain CDR (%) | | | Total (%) |
|---|---|---|---|---|---|---|---|---|---|
| | | | CDR1 | CDR2 | CDR3 | CDR1 | CDR2 | CDR3 | |
| ITC63B | L26539/L26540 | Human | 20 | 24 | 32 | 31 | 57 | 27 | 31 |
| ITC52 | L26537/L26538 | Human | 40 | 24 | 39 | 23 | 14 | 9 | 25 |
| ITC48 | L26535/L26536 | Human | 80 | 56 | 6 | 24 | 29 | 9 | 29 |
| ITC39 | L26533/L26534 | Human | 20 | 24 | 25 | 38 | 43 | 36 | 30 |
| ITC33 | L26531/L26532 | Human | 20 | 24 | 25 | 50 | 43 | 18 | 30 |
| 7-17 | U39898/U39901 | Mouse | 20 | 35 | 25 | 25 | 29 | 18 | 26 |
| 27-156 | U39899/U39902 | Mouse | 40 | 24 | 25 | 35 | 29 | 9 | 26 |
| 27-287 | U39900/U39903 | Mouse | 20 | 24 | 19 | 27 | 14 | 9 | 20 |
| EV2001 | * | Human | 20 | 24 | 19 | 25 | 43 | 9 | 22 |

*Reference: WO2007/094423

Example 5

Assessment of whether or not the Resulting Antibody Gene Codes for Anti-HCMV Antibody The resulting cDNAs of H-chain and L-chain were each inserted into expression vectors and then simultaneously introduced into a 293T cell. Gene transfer was conducted with Lipofectamine (Invitrogen) and PLUS reagent (Invitrogen) under the conditions recommended by the manufacturer (Invitrogen Catalogue: Cat. No. 18324-111, Cat. No. 18324-012 or Cat. No. 18324-020). Two days later, the culture supernatant was collected, and subjected to ELISA method using a 96-well plate coated with anti-human IgG antibody and GST-fused HCMV-AD1 to assess if the antibody in the culture supernatant is a human IgG antibody and whether it binds to HCMV-AD1.

Example 6

Production of Antibody Protein

The resulting anti-HCMV antibody-expressing plasmid was introduced into a CHO cell. Gene transfer was conducted by employing the same method as the above-described 293T cells. Cultivation was performed in the presence of a selection marker to obtain a CHO cell clone that constantly produced the antibody.

The same CHO cell that stably produced the antibody was cultured in a serum-free medium, and the culture supernatant was collected. This culture supernatant was added to a Protein A column and subjected to affinity purification to obtain a purified antibody. The column used was a prepacked column of HiTrap rProtein A FF (GE Healthcare), while the purificaresidues of CDR-H3 are numbered sequentially starting from the N-terminus (methionine) of the amino acid sequence of the heavy chain including the signal sequence of SEQ ID NO:2.

Meanwhile, amino acids that constitute proteins in nature can be grouped according to the properties of their side chains. Examples of amino acid groups having the same property include aromatic amino acids (tyrosine, phenylalanine, tryptophan), basic amino acids (lysine, arginine, histidine), acidic amino acids (aspartic acid, glutamic acid), neutral amino acids (serine, threonine, asparagine, glutamine), amino acids having a hydrocarbon chain (alanine, valine, leucine, isoleucine, proline) and else (glycine, methionine, cysteine).

In this section, the term "conservative amino acid substitution" refers to substitution between amino acids with similar properties, that is, amino acid substitution mainly between the amino acids belonging to the same group mentioned above. Such substitution is thought to have no significant influence or change on the property of the original protein. On the other hand, the term "nonconservative amino acid substitution" differs from the above substitution in that it refers to substitution with an amino acid whose property greatly differs from that of the original amino acid.

(1) Preparation of CDR-H3 Variants of EV2038

For the 16 amino acid residues constituting CDR-H3 of EV2038, each of them was subjected to nonconservative amino acid substitution by 2-step PCR method to prepare variants (V117K, T118W, R119V, D120I, L121E, E122L, W123T, I124D, P125R, G126F, D127I, Y128N, Y129N, M130Q, D131I and V132K). First, the first half of the gene fragment was obtained with a pair of 38Hind-S (CAC-CAAGCTTTGTGCAAGAACATGAAGCATC: SEQ ID NO:19) and a reverse primer for the substitution site and the latter half of the gene fragment was obtained with a pair of a forward primer for the substitution site and 38Not-A (ATAA-GAATGCGGCCGCGCCGTCGCACTCATTTACC: SEQ ID NO:20). Second PCR was performed using these as templates to obtain a full-length variant antibody gene. Subsequently, the antibody gene was processed with restriction enzyme NotI to produce sticky ends and then inserted into an antibody-producing plasmid. The nucleotide sequence of each variant was verified using a primer for verifying a nucleotide sequence (ACCAGACATAATAGCTGACAG: SEQ ID NO:21) with 3130 Genetic Analyzer (ABI) according to a suggested protocol.

2) Demonstration of Antibody Expression of CDR-H3 Variants of EV2038

The resulting variant plasmid (H-chain) and the original plasmid of the L-chain were cotransfered into CHO cell according to the suggested protocol of Lipofectamine LTX (Invitrogen). Forty-eight hours later, the culture supernatant was collected. The serially-diluted culture supernatants were allowed to react with solid-phased anti-human IgG antibodies (0.25 µg/well) in Immuno Plate (Maxi sorp, Nunc) at room temperature for an hour. As a secondary antibody, anti-human immunoglobulin G gamma and anti-human immunoglobulin G lambda (MBL) were allowed to react at room temperature for 11 hours. Fifty µL/mL of Sure Blue (MPL) containing TMB substrate as a color-producing agent was added, left to stand at room temperature for 30 minutes, and then added with an equal amount of 1.5M phosphoric acid to determine absorption at a wavelength of 450 nm using a microplate reader (680XR, BIO-RAD). The verification of the presence or absence and quantitation of the antibody were conducted based on the absorbance of the gamma- and lambda-chains.

3) Evaluation of Binding Capacity of EV2038 CDR-H3 Variants to AD1 by ELISA

An antibody adjusted to a concentration of 1 µg/mL based on the lambda-chain was allowed to react in dilution series with 5 µg/mL of solid-phased AD1 in Immuno Plate (Poly sorp, Nunc). Subsequently, ELISA was carried out as described above. The binding capacities of the variants to AD1 antigen were evaluated by the absorbances at 450 nm of the resulting variants and EV2038 (original). As a result, nonconservative amino acid substitution of the residues 121-126 of EV2038 CDR-H3 except residue 122 significantly reduced the binding capacity to AD1, and thus these residues were suggested to be important as paratopes of AD1 (FIG. 2).

(4) Preparation of EV2038 CDR-H3 Variants (2)

Among the five amino acid residues whose binding capacities to AD1 decreased upon nonconservative amino acid substitution, the four amino acid residues 121, 123, 124 and 126 were substituted with amino acids with similar properties. Five types of amino acids were used for each residue. Specifically, variants shown in FIG. 3 were prepared. Proline at position 125 was substituted with all of the natural amino acids other than the original amino acid (FIG. 4). The variants were prepared as described above.

(5) Evaluation of Binding Capacities of CDR-H3 Variants of EV2038 to AD1 by ELISA An antibody adjusted to a concentration of 1 µg/mL based on the lambda-chain was allowed to react in dilution series with 5 µg/mL of solid-phased AD1 in Immuno Plate (Poly sorp, Nunc). Subsequently, ELISA was carried out as described above to evaluate the binding capacities of the variants to AD1. As to amino acids at positions 121, 123, 124 and 126, most of the amino acid substitutions for conservative amino acids maintained binding capacities to AD1 (FIG. 3). However, proline at position 125 had no binding capacity to AD1 upon substitution with any other natural amino acids (19 types) (FIG. 4). Hence, in CDR-H3 of EV2038 according to the present invention, proline at position 125 was shown to be a requisite amino acid for AD1 binding property of the antibody.

(6) Preparation of CDR-H3 Variants of EV2038 (3)

Conservative amino-acid substitution was also carried out for the amino acid residues whose binding capacities to AD1 did not reduce upon nonconservative amino acid substitution (total of 11 residues at positions 117-120, 122 and 127-132) according to the same method to conduct evaluation of the binding capacities to AD1. As a result, variants with conservative amino acid substitution in this region (V117L, V117I, T118S, T118K, R119K, R119T, D120E, D120A, E122D, E122A, D127E, D127A, Y128F, Y128W, Y129F, Y129W, M130F, M130I, D131E, D131A, V132Y and V132S) were found to retain binding capacities to AD1, like nonconservative amino acid substitution (FIG. 5).

(7) Preparation of CDR-H3 Variants of EV2038 (4)

Total of four types of variants were prepared by simultaneously substituting two or four amino acid residues among the amino acid residues whose binding capacities to AD1 decreased upon nonconservative amino acid substitution other than proline at position 125 (total of four residues at positions 121, 123, 124 and 126) (two-amino-acid-substituted products: I124V/G126A and I124V/G126S, 4-amino-acid-substituted products: L121I/W123Y/I124V/G126A and L121I/W123Y/I124V/G126S) to evaluate their binding capacities to AD1. As a result, all of these multi-substituted variants were found to retain binding capacities to AD1 (FIG. 6).

(8) Preparation of CDR-H3 Variants of EV2038 (5)

One each of deleted and inserted variants (E122del, and G126_D127insE) were prepared targeting the amino acid residues whose binding capacities to AD1 decreased upon nonconservative amino acid substitution other than proline at position 125 (total of four residues at positions 121, 123, 124 and 126) to evaluate their binding capacities to AD1. As a result, the binding capacities to AD1 were completely eliminated for both E122del and G126_D127insE. Hence, the number of amino acid residues at this site (positions 121-126) (6 residues) was suggested to be important for binding to AD1 (FIG. 7).

In summary, an amino acid sequence of EV2038 CDR-H3 may be a following consensus sequence.

(SEQ ID NO: 22)
$X_n X_n X_n X_n X_1 X_n X_2 X_3 P X_4 X_n X_n X_n X_n X_n$ wherein, $X_n$=any natural amino acid
$X_1$=L, I, V, F or A
$X_2$=W, Y or F
$X_3$=I, V, L or M
$X_4$=G, S, A or T (9) Preparation of CDR-H2 Variants of EV2038

In order to study whether conservative substitution other than CDR-H3 has influence on the binding capacity to AD1, a variant in which N79 positioned in CDR-H2 of EV2038 was altered to N79Q was prepared according to the same method for preparing other variants to evaluate the binding capacity to AD1. From the results, binding capacity to AD1 was also proven not to be eliminated in the variant having N79 in CDR-H2 altered to N79Q (FIG. 8).

Sequence numbers of the amino acid sequences of H-chains (including signal sequence) of the variants prepared in this section are listed in Table 4.

TABLE 4

| Name of variant | SEQ ID NO |
|---|---|
| V117K | 28 |
| T118W | 29 |
| R119V | 30 |
| D120I | 31 |
| L121E | 32 |
| E122L | 33 |
| W123T | 34 |
| I124D | 35 |
| P125R | 36 |
| G126F | 37 |
| D127I | 38 |
| Y128N | 39 |
| Y129N | 40 |
| M130Q | 41 |
| D131I | 42 |
| V132K | 43 |
| L121I | 44 |
| L121V | 45 |
| L121A | 46 |
| L121F | 47 |
| L121P | 48 |
| W123Y | 49 |
| W123F | 50 |
| W123P | 51 |
| W123L | 52 |
| W123I | 53 |
| I124L | 54 |
| I124M | 55 |
| I124P | 56 |
| I124V | 57 |
| I124A | 58 |
| G126P | 59 |
| G126A | 60 |
| G126S | 61 |
| G126N | 62 |
| G126T | 63 |
| P125G | 64 |
| P125I | 65 |
| P125A | 66 |
| P125L | 67 |
| P125V | 68 |
| P125S | 69 |
| P125T | 70 |
| P125N | 71 |
| P125Q | 72 |
| P125D | 73 |
| P125E | 74 |
| P125K | 75 |
| P125H | 76 |
| P125C | 77 |
| P125M | 78 |
| P125Y | 79 |
| P125W | 80 |
| P125F | 81 |
| V117L | 82 |
| V117I | 83 |
| T118S | 84 |
| T118K | 85 |
| R119K | 86 |
| R119T | 87 |
| D120E | 88 |
| D120A | 89 |
| E122D | 90 |
| E122A | 91 |
| D127E | 92 |
| D127A | 93 |
| Y128F | 94 |
| Y128W | 95 |
| Y129F | 96 |
| Y129W | 97 |
| M130F | 98 |
| M130I | 99 |
| D131E | 100 |
| D131A | 101 |
| V132Y | 102 |
| V132S | 103 |
| I124V/G126A | 104 |
| I124V/G126S | 105 |
| L121I/W123Y/I124V/G126A | 106 |
| L121I/W123Y/I124V/G126S | 107 |
| E122del | 108 |
| G126_D127insE | 109 |
| N79Q | 110 |

Example 8

Epitope Mapping of Anti-HCMV AD1 Antibody

In order to determine the site on the glycoprotein gB bound by these AD1 antibodies, an expression vector cloned with AD1 of HCMV gB was introduced with deletion mutation by PCR method to prepare *E. coli* mutant series that express proteins having various deleted sites in AD1. These *E. coli* mutants were cultured and induced for expression. Thereafter, standard Western blot analysis was carried out using the cell lysate as an antigen. EV2038 and two types of variants with different substitution sites that have binding capacities to AD1 were selected as controls. One of the selected variants was a conservative amino-acid substituted form I124V that went through substitution of the isoleucine moiety at position 124 (one of the sites whose AD1-binding activity was not recognized upon nonconservative amino acid substitution) upstream to the loop structure of CDR-H3 (Shirai, H., et al., FEBS Letters, 1996; 399: p 1-8). The other was a nonconservative amino-acid substituted form V132K that went through substitution of valine at position 132 at the root of the loop structure of CDR-H3.

Figure 9:
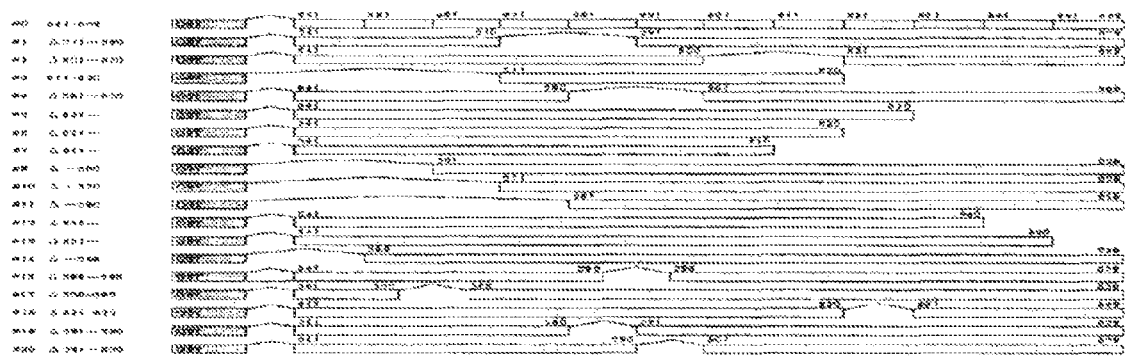
Figure 9:
Figure 10:
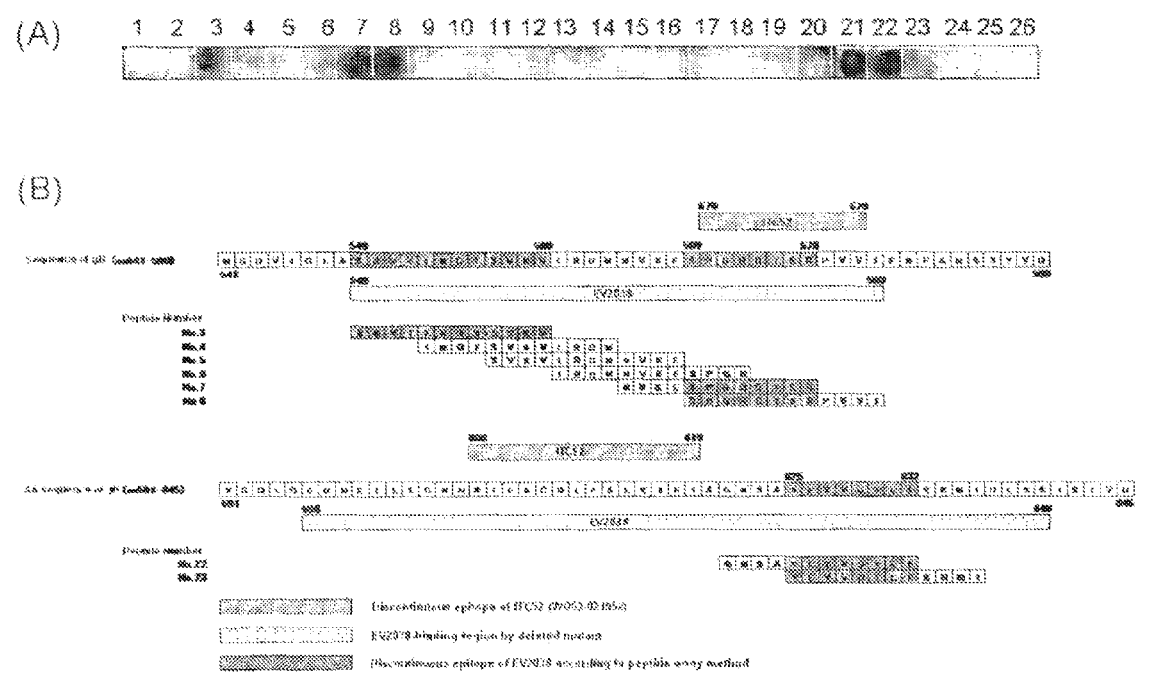

EV2038, I124V and V132K all bind to clone numbers #0, #12, #13, #14, #15 and #19, while EV2038 and the variants thereof were all found to have epitopes between the amino acid residues 549-580 (SCVTINQTSVKVLRDMN-VKESPGRCYSRPVVI: SEQ ID NO:23) and 596-640 (ED-NEILLGNHRTEECQLPSLKI-FIAGNSAYEYVDYLFKRMIDLSS: SEQ ID NO:24) (FIGS. 9 and 10). Here, the amino acid sequence of gB of HCMV AD169 strain as the antigen is numbered starting from the initiation codon, i.e., methionine, with reference to the sequence of Accession number P06473.

Furthermore, the epitope was determined more specifically for EV2038 with a peptide array. Twenty-six types of peptides were synthesized by shifting four residues at a time in a peptide of 12 residues within a range of the amino acid residues 548-641 (Table 5). Each peptide has its C-terminus bound to the surface of the derivatized cellulose membrane for solid phase synthesis as an individual spot of 3.7 mm×3.7 mm (SPOTs method, Sigma Genosys). The peptide bound by EV2038 was determined by standard dot blot synthesis. EV2038 bound to peptide numbers 3, 7, 8, 21 and 22 (FIG. 10) and the epitopes were determined to be amino acid residues 549-560 (SCVTINQTSVKV: SEQ ID NO:25), amino acid residues 569-576 (SPGRCYSR: SEQ ID NO:26) and amino acid residues 625-632 (YEYVDYLF: SEQ ID NO:27).

As for antibodies that recognize the AD1 region, ITC52 and the like that recognize a discontinuous epitope of amino acid residues 570-579 and 606-619 (WO93/21952 and J. Virol, 67; p 703-710 (1993)) have been reported. However, other than the amino acid residues 569-576 (SPGRCYSR: SEQ ID NO:26), at least two of the epitope-sequence moieties have previously been unreported, showing that EV2038 is an antibody that recognizes a discontinuous sequence that differs from those previously reported for AD1 antibodies (FIG. 10).

TABLE 5

| Peptide number | Amino acid sequence | SEQ ID NO |
|---|---|---|
| 1 | MGDVLGLASCVT | 111 |
| 2 | LGLASCVTINQT | 112 |
| 3 | SCVTINQTSVKV | 113 |
| 4 | INQTSVKVLRDM | 114 |
| 5 | SVKVLRDMNVKE | 115 |
| 6 | LRDMNVKESPGR | 116 |
| 7 | NVKESPGRCYSR | 117 |
| 8 | SPGRCYSRPVVI | 118 |
| 9 | CYSRPVVIFNFA | 119 |
| 10 | PVVIFNFANSSY | 120 |
| 11 | FNFANSSYVQYG | 121 |
| 12 | NSSYVQYGQLGE | 122 |
| 13 | VQYGQLGEDNEI | 123 |
| 14 | QLGEDNEILLGN | 124 |
| 15 | DNEILLGNHRTE | 125 |
| 16 | LLGNHRTEECQL | 126 |
| 17 | HRTEECQLPSLK | 127 |
| 18 | ECQLPSLKIFIA | 128 |
| 19 | PSLKIFIAGNSA | 129 |
| 20 | IFIAGNSAYEYV | 130 |
| 21 | GNSAYEYVDYLF | 131 |
| 22 | YEYVDYLFKRMI | 132 |
| 23 | DYLFKRMIDLSS | 133 |
| 24 | KRMIDLSSISTV | 134 |
| 25 | DLSSISTVDSMI | 135 |
| 26 | ISTVDSMIALDI | 136 |

Example 9

Evaluation of Neutralizing Activity (1) Immunostaining

In order to evaluate the effectivity of the anti-HCMV antibody (EV2038), neutralizing activity was determined. The neutralizing activity was evaluated as a rate of blockage, by the antibody, of HCMV (AD169 strain) infection in a human fetus lung-derived normal fibroblast cell (MRC-5: Riken BRC No. RCB0211). The procedure followed the method of Abai et al. (Journal of Immunological Methods 322 2007 82-93). Briefly, the procedure was as follows. Complement (5%) was added to the virus solution and the purified antibody and left for an hour. Then, the resultant was used to inoculate MRC-5 cell (37° C., 1 hour). The cell was washed twice, cultured for 20 hours, and then IE1, i.e., immediate-early protein of HCMV, was detected by immunofluorescent staining. HCMV-infected cells were counted with image analysis software Image J.

Figure 11:
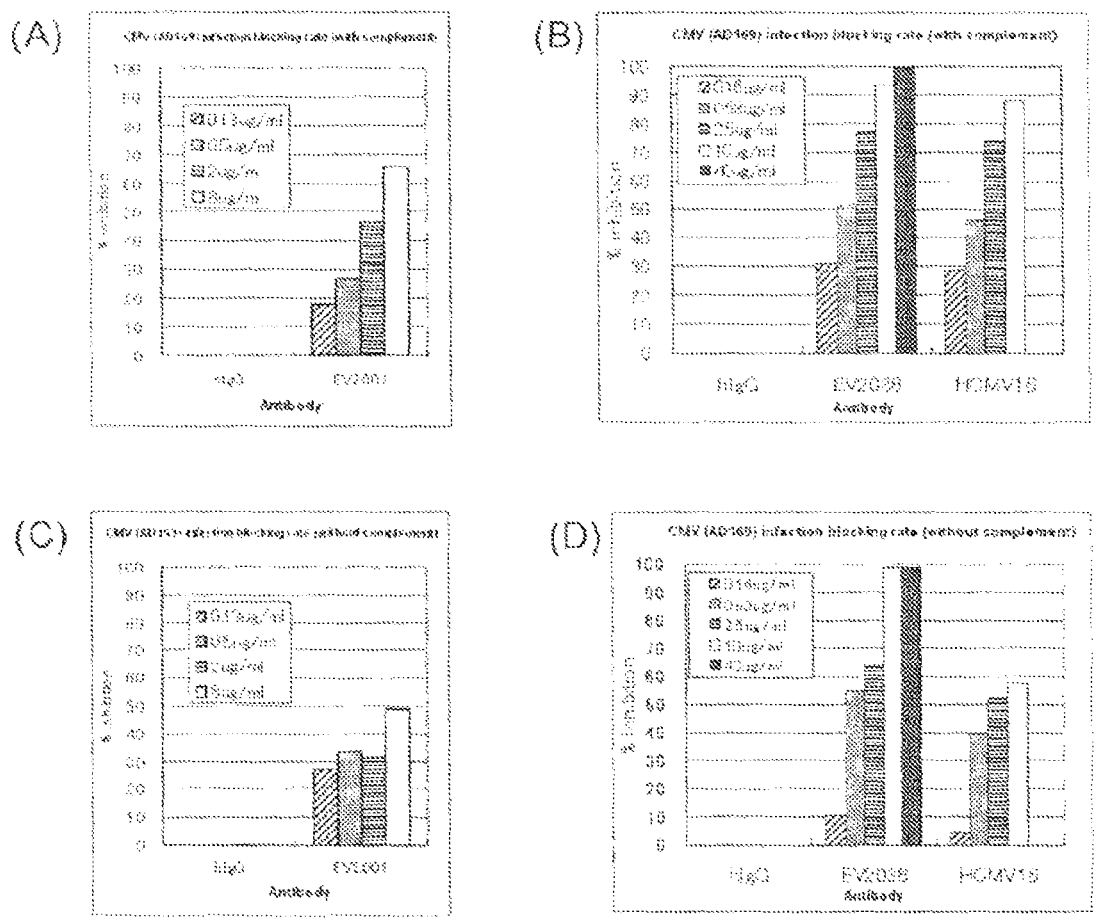
FIG. 11 is a graph showing results from evaluating the neutralizing activity of an anti-HCMV antibody of the present invention.

FIG. 11 shows the results of evaluating the neutralizing activity of the anti-HCMV antibody. A human monoclonal antibody (hIgG) that has no specificity to HCMV was used as a negative control while a mouse monoclonal antibody (clone name HCMV16, AbD serotec: 2470-5437) that binds to glycoprotein H (gH), i.e., one of the neutralizing epitopes of HCMV, was used as a positive control. The HCMV infection blocking rate of each antibody was indicated in percentage with respect to the infection blocking rate obtained upon addition of an equal concentration of hIgG. The 50% inhibition concentration ($IC_{50}$) upon addition of the complement was 0.58 μg/mL for EV2038, demonstrating that it has an effective neutralizing activity at a lower concentration than EV2001. In the absence of the complement, effective neutralizing activity was not obtained for EV2001 whereas $IC_{50}$ of EV2038 was 0.57 μg/mL, demonstrating that it has equal neutralizing activity to the case in the presence of the complement (Table 6).

TABLE 6

| Antibody name | Target antigen | IC50 (μg/mL) Cp+ | IC50 (μg/mL) Cp− |
|---|---|---|---|
| hIgG | — | n.d. | n.d. |
| EV2001 | AD1 | 3.08 | n.d. |
| EV2038 | AD1 | 0.58 | 0.57 |
| HCMV16 | gH | 0.87 | 2.15 | n.d.: not determined (2) Plaque Method

EV2038 that showed high neutralizing activity upon the above-described evaluation was further evaluated for its infection blocking activity by a plaque method (Masuho, Y. et al., J. Gen. Virol., 1987; 68: p 1457-1461). As virus strains, typical HCMV laboratory strains AD169, Towne, Davis and Merlin strains as well as clinically isolated HCMV strains T-137 and MDU-1 were used. The method was carried out briefly as follows. A virus solution of 50-100 PFU and a serially diluted purified antibody at a predetermined concentration were mixed, incubated at 37° C. for an hour, and used to inoculate a fibroblast cell (MRC-5) or a retinal pigment epithelial cell (ARPE-19) that had been unilaminated on 48-well microplates. Following inoculation, the resultant was incubated at 37° C. for 2 hours and then the culture supernatant was removed. After washing twice, the resultant was cultured at 37° C. in a standard medium containing 2% FCS. The cultivation was continued with a laboratory strain for 5-6 days or with a clinically isolated strain for 10-12 days until plaque formation was clearly confirmed by death of the virus-infected cells. Subsequently, 5% formalin was added to immobilize the cells, and staining was performed with 0.025% crystal violet. Following staining, the number of plaques per well was counted to calculate the infection blocking rate of the anti-HCMV antibody.

Table 7 are the results from the evaluation of the neutralizing activity of EV2038 by the plaque method. A human monoclonal antibody (hIgG) that has no specificity to HCMV was used as a negative control, while anti-CMV high-titer immunoglobulin formulation CytoGam (CSL Behring, Cyto-Gam Cytomegalovirus immune globulin intravenous, Prescribing information. (Revised July 2008)) approved in the United State to be applied for preventing development of HCMV infection associated with kidney transplantation was used as a positive control.

HCMV has been reported to have different entry mechanism between the infection mode to a fibroblast cell and the infection modes to epithelial and endothelial cells (Sinzger, C. et al., Curr Top Microbiol Immunol., 2008; 325: p 63-83). In many of the laboratory strains as typified by AD169 and Towne strains, infectivity to epithelial and endothelial cells is thought to be eliminated through several times of passage with fibroblast cells (Dai Wang, et al., J. Virol., 2005; 79: p 10330-10338). On the other hand, HCMV intrinsically has infectivity to broad tissues and cell types in vivo (Sinzger, C. et al., Curr Top Microbiol Immunol., 2008; 325: p 63-83). Hence, for an anti-HCMV antibody to exhibit a clinical effect, it may be important that the antibody has an effective neutralizing activity for both fibroblast cell type and epithelial cell/endothelial cell type that are used as the infected host cells.

It was demonstrated that anti-HCMV antibodies (EV2038) of the present invention had $IC_{50}$ of 0.012-0.037 μg/mL for infection of a fibroblast cell with the laboratory strain. With the clinically isolated strain (MDU-1) which retains infectivity to epithelial/endothelial cells, $IC_{50}$ was 0.044 μg/mL for infection of a fibroblast cell and 0.040 μg/mL for infection of fibroblast and epithelial cells, confirming that it has excellent neutralizing activity equally to both fibroblast cell type and epithelial/endothelial cell types. Moreover, EV2038 was highly active against AD169 strain by approximately 2000 times as compared to a commercially available anti-CMV high-titer immunoglobulin formulation CytoGam, and highly active by approximately 20 times as compared to the reported values of clinically developed and proven C23 (Masuho, Y. et al., J. Gen. Virol., 1987; 68: p 1457-1461).

conservative amino acid substitution. The procedure followed the above-described method of Abai et al. (Journal of Immunological Methods 322 2007 82-93). A human monoclonal antibody (hIgG) that has no specificity to HCMV was used as a negative control while a mouse monoclonal antibody (clone name HCMV16, AbD serotec: 2470-5437) that binds to glycoprotein H (gH), i.e., one of the neutralizing epitopes of CMV, was used as a positive control. The HCMV infection blocking rate of each antibody was indicated in percentage with respect to the infection blocking rate obtained upon addition of an equal concentration of hIgG. The 50% inhibition concentration ($IC_{50}$) was 0.45 μg/mL for I124V and 1.20 μg/mL for V132K, and both were shown to have almost equal activity to that of EV2038.

Example 11

Evaluation of Cell-to-Cell Infection Blocking Capacity

Furthermore, as one evaluation of the effectivity of EV2038, an HCMV-infected human fetus lung-derived normal fibroblast cell (MRC-5) was used to evaluate the cell-to-cell infection blocking activity of EV2038. The evaluation method was based on the method of Navarro et al. (Virology. 1993; 197: p 143-158). Specifically, MRC-5 that had been infected with HCMV (AD169) for 24 hours was used, to which the antibody was added in 4-fold dilution series starting from 10 mg/mL (approximately 67 nM). The cell was immobilized 6 days after the infection, and early infection expression protein IE1 was detected by immunostaining HCMV-infected cells were counted with image analysis soft-

TABLE 7

| Name of antibody | IC50 (μg/mL) | | | | | | |
|---|---|---|---|---|---|---|---|
| | HCMV laboratory strain | | | | HCVM clinically isolated strain | | |
| | AD169 | Towne | Merlin | Davis | T-137 | MDU-1 | |
| | Fibroblast cell | | | | Fibroblast cell | Fibroblast cell | Epithelial cell |
| hIgG | >10 | >10 | >10 | >10 | >10 | >10 | >10 |
| EV2038 | 0.027 | 0.025 | 0.012 | 0.037 | 0.07 | 0.044 | 0.04 |
| | (0.18) | (0.17) | (0.08) | (0.25) | (0.47) | (0.29) | (0.27) |
| CytoGam | 57.6 | N.D. | N.D. | N.D. | 33 | 51 | 3.8 |

N.D.: not determined
(In the table, values in parentheses are mol concentrations (nM) calculated provided that the molecular weight of the antibody is 150 kDa)

Example 10

Evaluation of Neutralizing Activity of EV2038 Variant Antibody

Two types of variants with different substitution sites were selected among the EV2038 variants to evaluate the neutralizing activities thereof. One was a conservative amino-acid substituted form I124V that went through substitution of the isoleucine moiety at position 124 (upstream to the loop structure of CDR-H3) whose AD1-binding activity was not recognized upon nonconservative amino acid substitution. The other was a nonconservative amino-acid substituted form V132K that went through substitution of valine at position 132 (at the root of the loop structure of CDR-H3) which had equal AD1-binding activity to the original form upon nonware Image J. As a result, it was found that addition of anti-AD1 antibody EV2038 to the infected cell can significantly inhibit cell-to-cell infection of the virus (Table 8).

In the table, (1) +++, (2) ++, (3) +, (4) ± and (5) − represent 100-75% inhibition, 75-50% inhibition, 50-25% inhibition, 25-0% inhibition and no inhibitory effect against spread of infection, respectively.

The report by Navarro et al. (Virology. 1993; 197: p 143-158) showed an exemplary case where antibodies with the highest activity (CH177-3, CH244-4, etc.) exhibited 100-75% inhibition at a concentration of 10 mg/mL. With EV2038, however, 100-75% cell infection inhibition can be seen at a concentration range of 10-0.63 μg/mL, and further 75-50% cell-to-cell infection inhibitory effect at 0.16 μg/mL (1.07 nM).

TABLE 8

| | Concentration upon addition (μg/mL) | | | | | | Without addition |
|---|---|---|---|---|---|---|---|
| | 10 | 2.5 | 0.63 | 0.18 | 0.04 | 0.01 | |
| EV2038 | +++ | +++ | +++ | ++ | + | − | − |

From the above-described properties, an anti-HCMV antibody or an antigen-binding fragment thereof according to the present invention appears to provide a new dimension as a prophylactic or therapeutic drug for various diseases caused by HCMV, for example, diseases such as interstitial pneumonia, retinitis, gastroenteritis or encephalitis in an immunodeficiency patient, or abnormality of hepatic function, interstitial pneumonia or mononucleosis that develops due to HCMV infection during newborn period or infancy.

Up to here, the present invention have been specifically described according to specific embodiments. These embodiments, however, are solely provided for description and are not restrictive. The scope of the present invention may be altered or modified in any way within the requirements of the scope of the claims, which fall within the technical scope of the present invention.

Industrial Applicability

An anti-HCMV antibody of the present invention and a pharmaceutical composition containing the antibody are expected to be used as a prophylactic or therapeutic drug for various diseases caused by HCMV, for example: (a) diseases such as interstitial pneumonia, retinitis, gastroenteritis, encephalitis and the like caused by HCMV reactivation in immunodeficiency states such as AIDS, cancer, after organ transplantation, after bone-marrow transplantation and after hemodialysis; (b) congenital CMV infection due to transmission of HCMV infection from a pregnant woman to a fetus; (c) miscarriage, stillbirth and death shortly after birth caused by the above-described congenital CMV infection; (d) low birth weight, hepatosplenomegaly, jaundice, thrombocytopenic purpura, microcephaly, disorder of mental development, delay of intellectual development, chorioretinitis and hearing impairment in the case of survival through the above-described congenital CMV infection; and (e) abnormality of hepatic function, interstitial pneumonia and mononucleosis due to HCMV infection during newborn or infancy.

The invention claimed is:

1. A monoclonal antibody or an antigen-binding fragment thereof that specifically binds to the AD1 region of human cytomegalovirus (HCMV) glycoprotein gB, comprising:
   (i)
   (a) a heavy chain CDR1 comprising the amino acid sequence of SEQ ID NO: 13;
   (b) a heavy chain CDR2 comprising the amino acid sequence of SEQ ID NO: 14; and
   (c) a heavy chain CDR3 comprising the amino acid sequence of SEQ ID NO: 15, and
   (ii)
   (a) a light chain CDR I comprising the amino acid sequence of SEQ ID NO: 16;
   (b) a light chain CDR2 comprising the amino acid sequence of SEQ ID NO: 17; and
   (c) a light chain CDR3 comprising the amino acid sequence of SEQ ID NO: 18.

2. The antibody or an antigen-binding fragment thereof according to claim 1, comprising:
   (a) a heavy chain variable region (HCVR) comprising the amino acid sequence of SEQ ID NO: 10; and
   (b) a light chain variable region (LCVR) comprising the amino acid sequence of SEQ ID NO: 12.

3. The antibody or an antigen-binding fragment thereof according to claim 1, comprising:
   (a) a heavy chain (H-chain) comprising the amino acid sequence of SEQ ID NO: 6; and
   (b) a light chain (L-chain) comprising the amino acid sequence of SEQ ID NO: 8.

4. The antibody or the antigen-binding fragment according to claim 1, wherein the class/subclass of the antibody is IgG1/λ.

5. A pharmaceutical composition comprising the antibody or the antigen-binding fragment according to claim 1 and a pharmaceutically acceptable carrier.

6. A method of treating a human cytomegalovirus (HCMV) infection, comprising:
   administering a pharmaceutical composition to a subject in need thereof, the composition comprising the antibody or the antigen-binding fragment according to claim 1 and a pharmaceutically acceptable carrier.

7. The method of claim 6, wherein the HCMV infection is congenital cytomegalovirus (CMV) infection.

* * * * *